(12) United States Patent
Vanasse et al.

(10) Patent No.: US 10,085,842 B2
(45) Date of Patent: Oct. 2, 2018

(54) METHOD AND APPARATUS FOR WRIST ARTHROPLASTY

(71) Applicant: Biomet Manufacturing, LLC, Warsaw, IN (US)

(72) Inventors: Thomas M. Vanasse, South Bend, IN (US); Benjamin P. Heilman, Warsaw, IN (US); Andrew K. Palmer, Eastham, MA (US)

(73) Assignee: Biomet Manufacturing, LLC, Warsaw, IN (US)

( * ) Notice: Subject to any disclaimer, the term of this patent is extended or adjusted under 35 U.S.C. 154(b) by 150 days.

(21) Appl. No.: 14/563,064

(22) Filed: Dec. 8, 2014

(65) Prior Publication Data
US 2015/0100132 A1 Apr. 9, 2015

Related U.S. Application Data

(63) Continuation of application No. 13/243,171, filed on Sep. 23, 2011, now Pat. No. 8,940,055, which is a
(Continued)

(51) Int. Cl.
*A61F 2/42* (2006.01)
*A61F 2/46* (2006.01)
*A61F 2/30* (2006.01)

(52) U.S. Cl.
CPC .......... *A61F 2/4261* (2013.01); *A61F 2/4606* (2013.01); *A61F 2/4684* (2013.01);
(Continued)

(58) Field of Classification Search
CPC .............. A61F 2/4261; A61F 2002/305; A61F 2002/4264; A61F 2/583; A61F 2002/4266; A61F 2/4606
See application file for complete search history.

(56) References Cited

U.S. PATENT DOCUMENTS 3,805,302 A 4/1974 Mathys et al.
3,875,594 A 4/1975 Swanson
(Continued)

FOREIGN PATENT DOCUMENTS

DE 10043107 9/2002
DE 10237016 2/2004
(Continued)

OTHER PUBLICATIONS

European Search Report for EP 07 25 3509 dated Jan. 14, 2008.
(Continued)

*Primary Examiner* — Ann Schillinger
(74) *Attorney, Agent, or Firm* — Schwegman Lundberg & Woessner, P.A.

(57) ABSTRACT

A method of implanting a wrist prosthesis in a distal portion of an ulna for articulation at least near a radius and a carpal complex of a wrist joint is provided. The method can include forming an incision near a distal portion of the radius and ulna joint. The method can also include resecting a distal portion of the ulna and positioning a stage member in a fixed position relative to the ulna. The method can further include sliding a bearing member relative to the stage member to hold the bearing member relative to the stage member and the distal ulna. The method can also include fixing the bearing member to a bearing fixation member extending from the stage member, and attaching soft tissue to at least one of the bearing member and the stage member.

20 Claims, 55 Drawing Sheets

Related U.S. Application Data continuation of application No. 12/576,844, filed on Oct. 9, 2009, now Pat. No. 8,052,756, which is a continuation-in-part of application No. 12/562,692, filed on Sep. 18, 2009, now Pat. No. 8,105,390, which is a continuation-in-part of application No. 12/553,350, filed on Sep. 3, 2009, now Pat. No. 8,066,777, which is a continuation-in-part of application No. 12/389,919, filed on Feb. 20, 2009, now Pat. No. 8,105,389, which is a continuation-in-part of application No. 11/867,884, filed on Oct. 5, 2007, now Pat. No. 8,105,388, which is a continuation-in-part of application No. 11/517,537, filed on Sep. 7, 2006, now Pat. No. 8,821,581, which is a continuation-in-part of application No. 11/260,729, filed on Oct. 27, 2005, now Pat. No. 8,372,154, which is a continuation-in-part of application No. 10/862,821, filed on Jun. 7, 2004, now Pat. No. 7,776,970, which is a continuation-in-part of application No. 10/279,240, filed on Oct. 24, 2002, now Pat. No. 6,746,486.

(52) U.S. Cl.
CPC ............... *A61F 2002/30604* (2013.01); *A61F 2002/30614* (2013.01); *A61F 2002/30616* (2013.01); *A61F 2002/30736* (2013.01); *A61F 2002/4264* (2013.01); *A61F 2002/4266* (2013.01); *A61F 2310/00023* (2013.01); *A61F 2310/00029* (2013.01)

(56) References Cited

U.S. PATENT DOCUMENTS

| | | |
|---|---|---|
| 3,879,767 A | 4/1975 | Stubstad |
| 3,909,853 A | 10/1975 | Lennox |
| 4,003,096 A | 1/1977 | Frey |
| 4,100,626 A | 7/1978 | White |
| 4,106,128 A | 8/1978 | Greenwald et al. |
| 4,158,893 A | 6/1979 | Swanson |
| 4,164,793 A | 8/1979 | Swanson |
| 4,178,640 A | 12/1979 | Buechler et al. |
| 4,193,139 A | 3/1980 | Walker |
| 4,198,712 A | 4/1980 | Swanson |
| 4,198,713 A | 4/1980 | Swanson |
| 4,206,517 A | 6/1980 | Pappas et al. |
| 4,307,473 A | 12/1981 | Weber |
| 4,645,505 A | 2/1987 | Swanson |
| 4,714,476 A | 12/1987 | Ranawat et al. |
| 4,784,661 A | 11/1988 | Beckenbaugh et al. |
| 4,936,854 A | 6/1990 | Swanson |
| 4,936,860 A | 6/1990 | Swanson |
| 4,944,757 A | 7/1990 | Martinez et al. |
| 5,133,762 A | 7/1992 | Branemark et al. |
| 5,197,966 A | 3/1993 | Sommerkamp |
| 5,314,485 A | 5/1994 | Judet et al. |
| 5,314,486 A | 5/1994 | Zang et al. |
| 5,326,364 A | 7/1994 | Clift, Jr. et al. |
| 5,405,401 A | 4/1995 | Lippincott, III et al. |
| 5,443,512 A | 8/1995 | Parr et al. |
| 5,458,646 A | 10/1995 | Giachino et al. |
| 5,507,821 A | 4/1996 | Sennwald et al. |
| 5,683,466 A | 11/1997 | Vitale |
| 5,702,470 A | 12/1997 | Menon |
| 5,702,482 A | 12/1997 | Thongpreda et al. |
| 5,766,258 A | 6/1998 | Simmen et al. |
| 5,772,663 A | 6/1998 | Whiteside et al. |
| 5,853,413 A | 12/1998 | Carter et al. |
| 5,951,604 A * | 9/1999 | Scheker ............... 623/21.11 |
| 6,059,832 A | 5/2000 | Menon |
| 6,099,571 A | 8/2000 | Knapp |
| 6,168,630 B1 | 1/2001 | Keller et al. |
| 6,183,519 B1 | 2/2001 | Bonnin et al. |
| 6,228,091 B1 | 5/2001 | Lombardo et al. |
| 6,284,000 B1 | 9/2001 | Ege et al. |
| 6,302,915 B1 * | 10/2001 | Cooney et al. ............ 623/21.12 |
| 6,436,146 B1 | 8/2002 | Hassler et al. |
| 6,485,520 B1 * | 11/2002 | Hubach et al. ............ 623/21.13 |
| 6,506,216 B1 | 1/2003 | McCue et al. |
| 6,508,819 B1 | 1/2003 | Orbay |
| 6,527,807 B1 | 3/2003 | O'Neil et al. |
| 6,746,486 B1 | 6/2004 | Shultz et al. |
| 6,811,568 B2 | 11/2004 | Minamikawa |
| 6,890,358 B2 | 5/2005 | Ball et al. |
| 6,969,407 B2 | 11/2005 | Klotz et al. |
| 7,291,175 B1 | 11/2007 | Gordon |
| 7,597,715 B2 | 10/2009 | Brown et al. |
| 7,766,970 B2 | 8/2010 | Shultz et al. |
| 8,052,756 B2 | 11/2011 | Vanasse et al. |
| 8,066,777 B2 | 11/2011 | Palmer et al. |
| 8,105,388 B2 | 1/2012 | Palmer et al. |
| 8,105,389 B2 | 1/2012 | Berelsman et al. |
| 8,105,390 B2 | 1/2012 | Shultz et al. |
| 8,372,154 B2 | 2/2013 | Shultz et al. |
| 8,551,180 B2 | 10/2013 | Shultz et al. |
| 8,821,581 B2 | 9/2014 | Berelsman et al. |
| 8,940,055 B2 | 1/2015 | Vanasse et al. |
| 2003/0216813 A1 | 11/2003 | Ball et al. |
| 2004/0064073 A1 * | 4/2004 | Heldreth ............... 600/595 |
| 2004/0073315 A1 | 4/2004 | Justin et al. |
| 2004/0230312 A1 | 11/2004 | Hanson et al. |
| 2005/0004675 A1 | 1/2005 | Shultz et al. |
| 2005/0085921 A1 | 4/2005 | Gupta et al. |
| 2006/0030946 A1 | 2/2006 | Ball et al. |
| 2006/0036330 A1 | 2/2006 | Shultz et al. |
| 2006/0161260 A1 | 7/2006 | Thomas et al. |
| 2007/0012809 A1 | 1/2007 | Fellinger |
| 2007/0055381 A1 | 3/2007 | Berelsman et al. |
| 2007/0185582 A1 * | 8/2007 | Palmer ............... A61F 2/4261 623/21.12 |
| 2007/0225820 A1 | 9/2007 | Thomas et al. |
| 2008/0027558 A1 | 1/2008 | Palmer et al. |
| 2008/0288079 A1 * | 11/2008 | Leibel ............... 623/20.11 |
| 2009/0204224 A1 | 8/2009 | Berelsman et al. |
| 2009/0254189 A1 * | 10/2009 | Scheker ............... A61F 2/4261 623/21.11 |
| 2009/0319050 A1 | 12/2009 | Palmer et al. |
| 2010/0010636 A1 | 1/2010 | Shultz et al. |
| 2010/0087879 A1 | 4/2010 | Vanasse et al. |
| 2010/0130981 A1 | 5/2010 | Richards |

FOREIGN PATENT DOCUMENTS

| | | |
|---|---|---|
| EP | 0034192 A1 | 8/1981 |
| EP | 0607748 A1 | 7/1994 |
| FR | 2660856 | 10/1991 |
| GB | 2269752 | 2/1994 |
| GB | 2269752 A | 2/1994 |
| WO | 9200709 | 1/1992 |
| WO | 9731593 A1 | 9/1997 |
| WO | 2006048520 | 5/2006 |
| WO | 2007047230 | 4/2007 |

OTHER PUBLICATIONS

Universal Total Wrist Implant System at www.visitkmi.com/totwrist.html, Sep. 4, 2001.

European Search Report dated Oct. 18, 2010 for EP08165873 filed Oct. 3, 2008, claiming benefit of U.S. Appl. No. 11/867,884, filed Oct. 5, 2007.

Universal Total Wrist Implant System at www.visitkmi.com/totwrist.html.

European Search Report EP 07 25 3509 dated Jan. 14, 2008.

"U.S. Appl. No. 10/862,821, Examiner Interview Summary dated Jun. 19, 2018", 2 pgs.

"U.S. Appl. No. 10/862,821, Final Office Action dated Jan. 29, 2009", 11 pgs.

"U.S. Appl. No. 10/862,821, Non Final Office Action dated Feb. 22, 2008", 11 pgs.

(56) References Cited

OTHER PUBLICATIONS

"U.S. Appl. No. 10/862,821, Non Final Office Action dated Jul. 10, 2009", 14 pgs.
"U.S. Appl. No. 10/862,821, Notice of Allowance dated Mar. 23, 2010", 11 pgs.
"U.S. Appl. No. 10/862,821, Notice of Non-Compliant Amendment dated Dec. 24, 2009", 5 pgs.
"U.S. Appl. No. 10/862,821, Preliminary Amendment filed May 24, 2005", 32 pgs.
"U.S. Appl. No. 10/862,821, Preliminary Amendment filed Aug. 9, 2005", 34 pgs.
"U.S. Appl. No. 10/862,821, Response filed Jan. 5, 2010 to Notice of Non-Compliant Amendment dated Dec. 24, 2009", 1 pg.
"U.S. Appl. No. 10/862,821, Response filed Apr. 29, 2009 to Final Office Action dated Jan. 29, 2009", 19 pgs.
"U.S. Appl. No. 10/862,821, Response filed Jun. 20, 2008 to Non Final Office Action dated Feb. 22, 2008", 18 pgs.
"U.S. Appl. No. 10/862,821, Response filed Aug. 24, 2007 to Restriction Requirement dated Jul. 27, 2007", 6 pgs.
"U.S. Appl. No. 10/862,821, Response filed Oct. 12, 2009 to Non Final Office Action dated Jul. 10, 2009", 17 pgs.
"U.S. Appl. No. 10/862,821, Response filed Oct. 27, 2008 to Restriction Requirement dated Sep. 28, 2008", 1 pg.
"U.S. Appl. No. 10/862,821, Response filed dec. 6, 2007 to Restriction Requirement dated Nov. 6, 2007", 5 pgs.
"U.S. Appl. No. 10/862,821, Restriction Requirement dated Jul. 27, 2007", 9 pgs.
"U.S. Appl. No. 10/862,821, Restriction Requirement dated Sep. 25, 2008", 5 pgs.
"U.S. Appl. No. 10/862,821, Restriction Requirement dated Nov. 6, 2007", 5 pgs.
"U.S. Appl. No. 11/260,729, Examiner Interview Summary dated Mar. 23, 2010", 3 pgs.
"U.S. Appl. No. 11/260,729, Examiner Interview Summary dated Sep. 1, 2009", 2 pgs.
"U.S. Appl. No. 11/260,729, Final Office Action dated Dec. 8, 2009", 9 pgs.
"U.S. Appl. No. 11/260,729, Non Final Office Action dated Mar. 1, 2012", 11 pgs.
"U.S. Appl. No. 11/260,729, Non Final Office Action dated May 27, 2009", 13 pgs.
"U.S. Appl. No. 11/260,729, Notice of Allowance dated Oct. 10, 2012", 7 pgs.
"U.S. Appl. No. 11/260,729, Response filed Feb. 26, 2009 to Restriction Requirement dated Jan. 26, 2009", 4 pgs.
"U.S. Appl. No. 11/260,729, Response filed Apr. 8, 2010 to Final Office Action dated Dec. 8, 2009", 23 pgs.
"U.S. Appl. No. 11/260,729, Response filed May 29, 2012 to Non Final Office Action dated Mar. 1, 2012", 26 pgs.
"U.S. Appl. No. 11/260,729, Response filed Aug. 27, 2009 to Non Final Office Action dated May 27, 2009", 24 pgs.
"U.S. Appl. No. 11/260,729, Restriction Requirement dated Jan. 26, 2009", 9 pgs.
"U.S. Appl. No. 11/867,884, Final Office Action dated Aug. 1, 2011", 9 pgs.
"U.S. Appl. No. 11/867,884, Non Final Office Action dated Mar. 2, 2011", 12 pgs.
"U.S. Appl. No. 11/867,884, Notice of Allowance dated Sep. 23, 2011", 5 pgs.
"U.S. Appl. No. 11/867,884, Notice of Non-Compliant Amendment dated Dec. 15, 2010", 3 pgs.
"U.S. Appl. No. 11/867,884, Response filed Jan. 18, 2011 to Notice of Non-Compliant Amendment dated Dec. 15, 2010", 9 pgs.
"U.S. Appl. No. 11/867,884, Response filed May 25, 2011 to Non Final Office Action dated Mar. 2, 2011", 13 pgs.
"U.S. Appl. No. 11/867,884, Response filed Aug. 18, 2011 to Final Office Action dated Aug. 1, 2011", 6 pgs.
"U.S. Appl. No. 11/867,884, Response filed Dec. 23, 2009 to Restriction Requirement dated Oct. 23, 2009", 10 pgs.
"U.S. Appl. No. 11/867,884, Restriction Requirement dated Oct. 23, 2009", 5 pgs.
"U.S. Appl. No. 12/389,919, Final Office Action dated Jun. 1, 2011", 7 pgs.
"U.S. Appl. No. 12/389,919, Non Final Office Action dated Feb. 14, 2011", 10 pgs.
"U.S. Appl. No. 12/389,919, Notice of Allowance dated Sep. 21, 2011", 8 pgs.
"U.S. Appl. No. 12/389,919, Notice of Non-Compliant Amendment dated Oct. 14, 2010", 2 pgs.
"U.S. Appl. No. 12/389,919, Preliminary Amendment filed Apr. 24, 2009", 3 pgs.
"U.S. Appl. No. 12/389,919, Response filed May 13, 2011 to Non Final Office Action dated Feb. 14, 2011", 11 pgs.
"U.S. Appl. No. 12/389,919, Response filed Jul. 11, 2011 to Final Office Action dated Jun. 1, 2011", 8 pgs.
"U.S. Appl. No. 12/389,919, Response filed Jul. 19, 2010 to Restriction Requirement dated Jun. 17, 2010", 8 pgs.
"U.S. Appl. No. 12/389,919, Response filed Nov. 15, 2010 to Notice of Non-Compliant Amendment dated Oct. 14, 2010", 8 pgs.
"U.S. Appl. No. 12/389,919, Restriction Requirement dated Jun. 17, 2010", 5 pgs.
"U.S. Appl. No. 12/553,350, Non Final Office Action dated Sep. 28, 2010", 10 pgs.
"U.S. Appl. No. 12/553,350, Notice of Allowance dated May 26, 2011", 8 pgs.
"U.S. Appl. No. 12/553,350, Notice of Allowance dated Aug. 12, 2011", 5 pgs.
"U.S. Appl. No. 12/553,350, Notice of Allowance dated Oct. 4, 2011", 2 pgs.
"U.S. Appl. No. 12/553,350, Response filed Jan. 28, 2011 to Non Final Office Action dated Sep. 28, 2010", 12 pgs.
"U.S. Appl. No. 12/553,350, Response filed Jul. 19, 2010 to Restriction Requirement dated Jun. 17, 2010", 10 pgs.
"U.S. Appl. No. 12/553,350, Restriction Requirement dated Jun. 17, 2010", 7 pgs.
"U.S. Appl. No. 12/562,692, Non Final Office Action dated Oct. 27, 2010", 9 pgs.
"U.S. Appl. No. 12/562,692, Notice of Allowance dated Mar. 21, 2011", 8 pgs.
"U.S. Appl. No. 12/562,692, Notice of Allowance dated Sep. 28, 2011", 5 pgs.
"U.S. Appl. No. 12/562,692, Response filed Jan. 19, 2011 to Non Final Office Action dated Oct. 27, 2010", 14 pgs.
"U.S. Appl. No. 12/562,692, Response filed Aug. 9, 2010 to Restriction Requirement dated Jul. 9, 2010", 8 pgs.
"U.S. Appl. No. 12/562,692, Restriction Requirement dated Jul. 9, 2010", 7 pgs.
"U.S. Appl. No. 12/576,844, Final Office Action dated May 10, 2011", 8 pgs.
"U.S. Appl. No. 12/576,844, Non Final Office Action dated Nov. 10, 2010", 8 pgs.
"U.S. Appl. No. 12/576,844, Notice of Allowance dated Jul. 22, 2011", 5 pgs.
"U.S. Appl. No. 12/576,844, Response filed Jan. 24, 2011 to Non Final Office Action dated Nov. 10, 2010", 12 pgs.
"U.S. Appl. No. 12/576,844, Response filed Jun. 7, 2011 to Final Office Action dated May 10, 2011", 10 pgs.
"U.S. Appl. No. 12/576,844, Response filed Sep. 27, 2010 to Restriction Requirement dated Aug. 25, 2010", 8 pgs.
"U.S. Appl. No. 12/576,844, Restriction Requirement dated Aug. 25, 2010", 5 pgs.
"U.S. Appl. No. 13/243,171, Advisory Action dated Dec. 12, 2013", 3 pgs.
"U.S. Appl. No. 13/243,171, Examiner Interview Summary dated Oct. 15, 2013", 3 pgs.
"U.S. Appl. No. 13/243,171, Final Office Action dated Jul. 29, 2013", 8 pgs.
"U.S. Appl. No. 13/243,171, Non Final Office Action dated Feb. 13, 2013", 9 pgs.
"U.S. Appl. No. 13/243,171, Notice of Allowance dated Sep. 12, 2014", 5 pgs.

(56) References Cited

OTHER PUBLICATIONS

"U.S. Appl. No. 13/243,171, Preliminary Amendment filed Dec. 12, 2011", 8 pgs.

"U.S. Appl. No. 13/243,171, Response filed Jan. 3, 2013 to Restriction Requirement dated Dec. 10, 2012", 1 pg.

"U.S. Appl. No. 13/243,171, Response filed May 13, 2013 to Non Final Office Action dated Feb. 13, 2013", 12 pgs.

"U.S. Appl. No. 13/243,171, Response filed Nov. 29, 2013 to Final Office Action dated Jul. 29, 2013", 12 pgs.

"U.S. Appl. No. 13/243,171, Restriction Requirement dated Dec. 10, 2012", 8 pgs.

"U.S. Appl. No. 13/338,623, 312 Amendment filed Aug. 29, 2013", 10 pgs.

"U.S. Appl. No. 13/338,623, Notice of Allowance dated May 30, 2013", 10 pgs.

"U.S. Appl. No. 13/338,623, Notice of Allowance daed Jul. 15, 2013", 5 pgs.

"U.S. Appl. No. 13/338,623, Notice of Allowance dated Sep. 4, 2013", 2 pgs.

"European Application Serial No. 07253509.9, Examination Notification Art. 94(3) dated Feb. 27, 2012", 6 pgs.

"European Application Serial No. 07253509.9, Examination Notification Art. 94(3) dated Oct. 10, 2008", 2 pgs.

"European Application Serial No. 07253509.9, Examination Notification Art. 94(3) dated Dec. 23, 2014", 4 pgs.

"European Application Serial No. 07253509.9, Response filed Feb. 16, 2009 to Examination Notification Art. 94(3) dated Oct. 10, 2008", 15 pgs.

"European Application Serial No. 07253509.9, Response filed Jul. 12, 2012 to Examination Notification Art. 94(3) dated Feb. 17, 2012", 17 pgs.

"European Application Serial No. 07253509.9, Response filed Oct. 8, 2015 to Examination Notification Art. 94(3) dated Dec. 23, 2014", 2 pgs.

"European Application Serial No. 08165873.4, Decision of Grant dated Feb. 26, 2015", 4 pgs.

"European Application Serial No. 08165873.4, Examination Notification Art. 94(3) dated Apr. 5, 2012", 3 pgs.

"European Application Serial No. 08165873.4, Examination Notification Art. 94(3) dated Nov. 15, 2013", 3 pgs.

"European Application Serial No. 08165873.4, Response filed Mar. 3, 2014 to Examination Notification Art. 94(3) dated Nov. 15, 2013", 215 pgs.

"European Application Serial No. 08165873.4, Response filed May 17, 2011 to Extended European Search Report dated Oct. 18, 2010", 13 pgs.

"European Application Serial No. 08165873.4, Response filed Sep. 6, 2012 to Examination Notification Art. 94(3) dated Apr. 5, 2012", 11 pgs.

\* cited by examiner

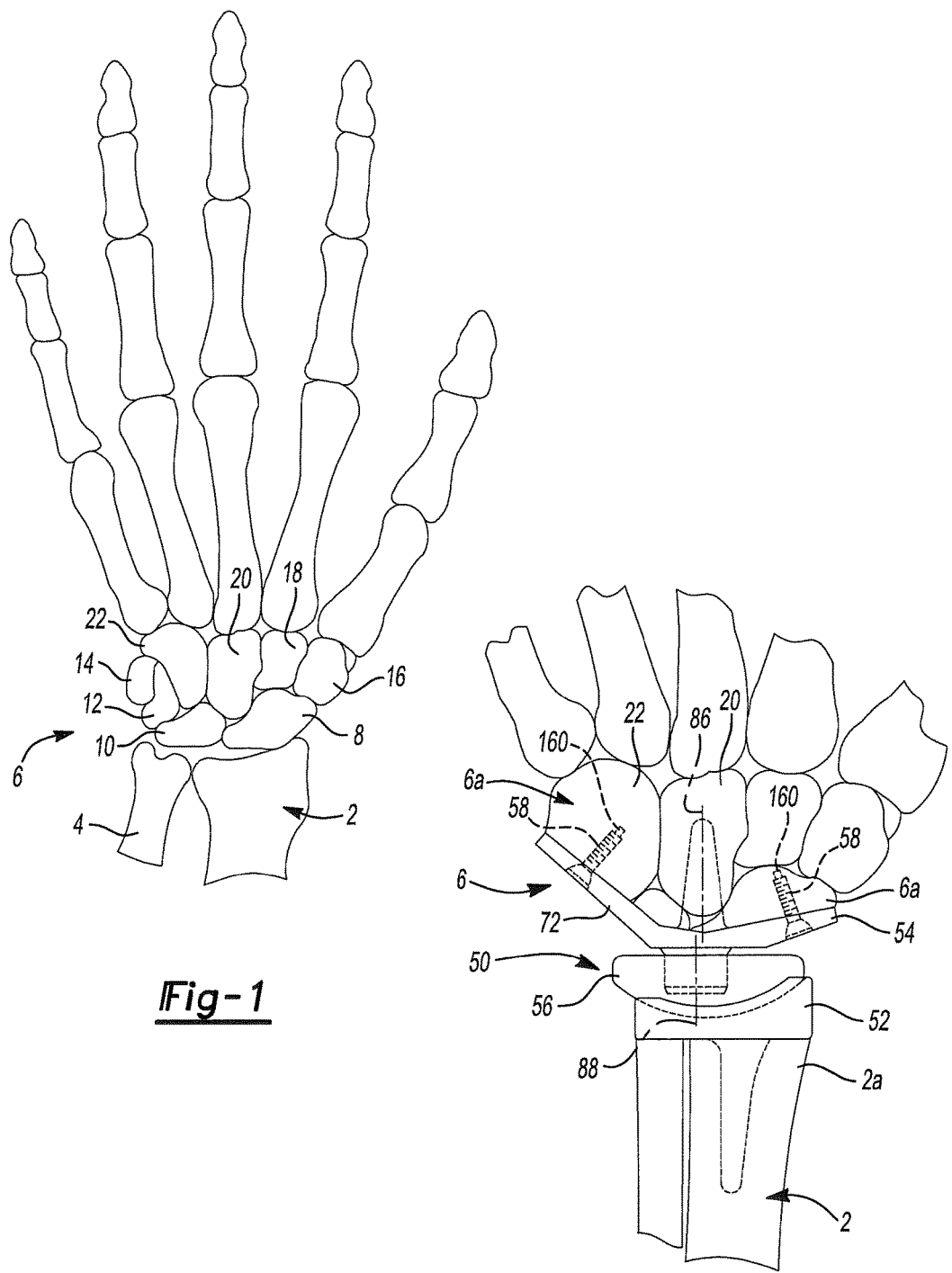

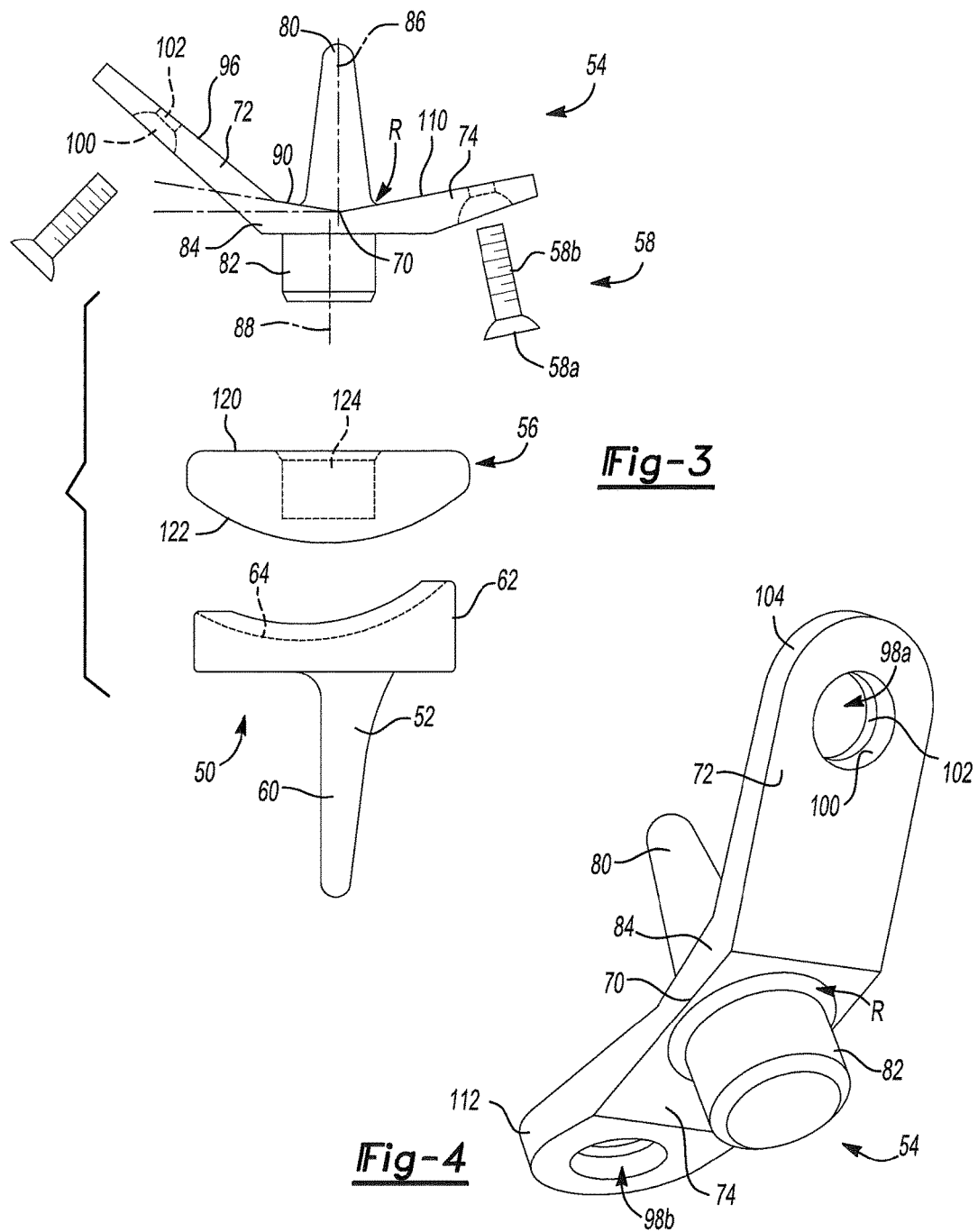

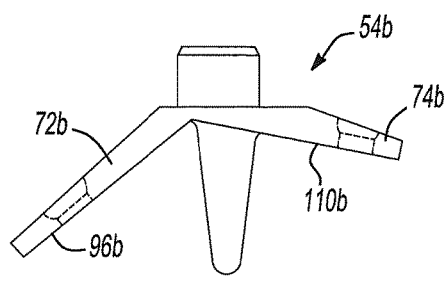
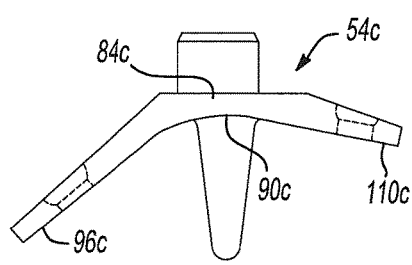
Fig-10
Fig-11
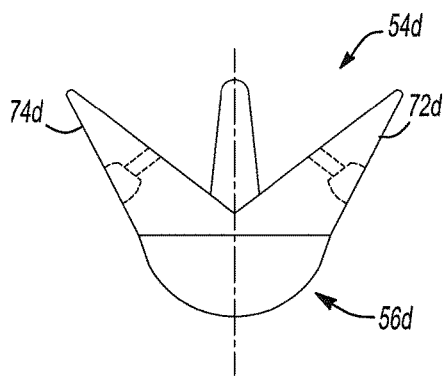
Fig-12
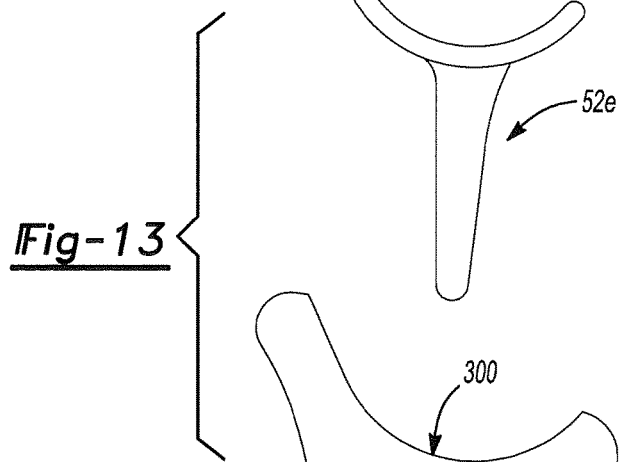
Fig-13
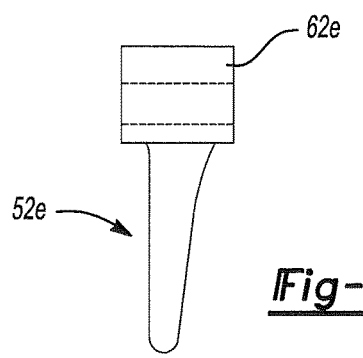
Fig-14

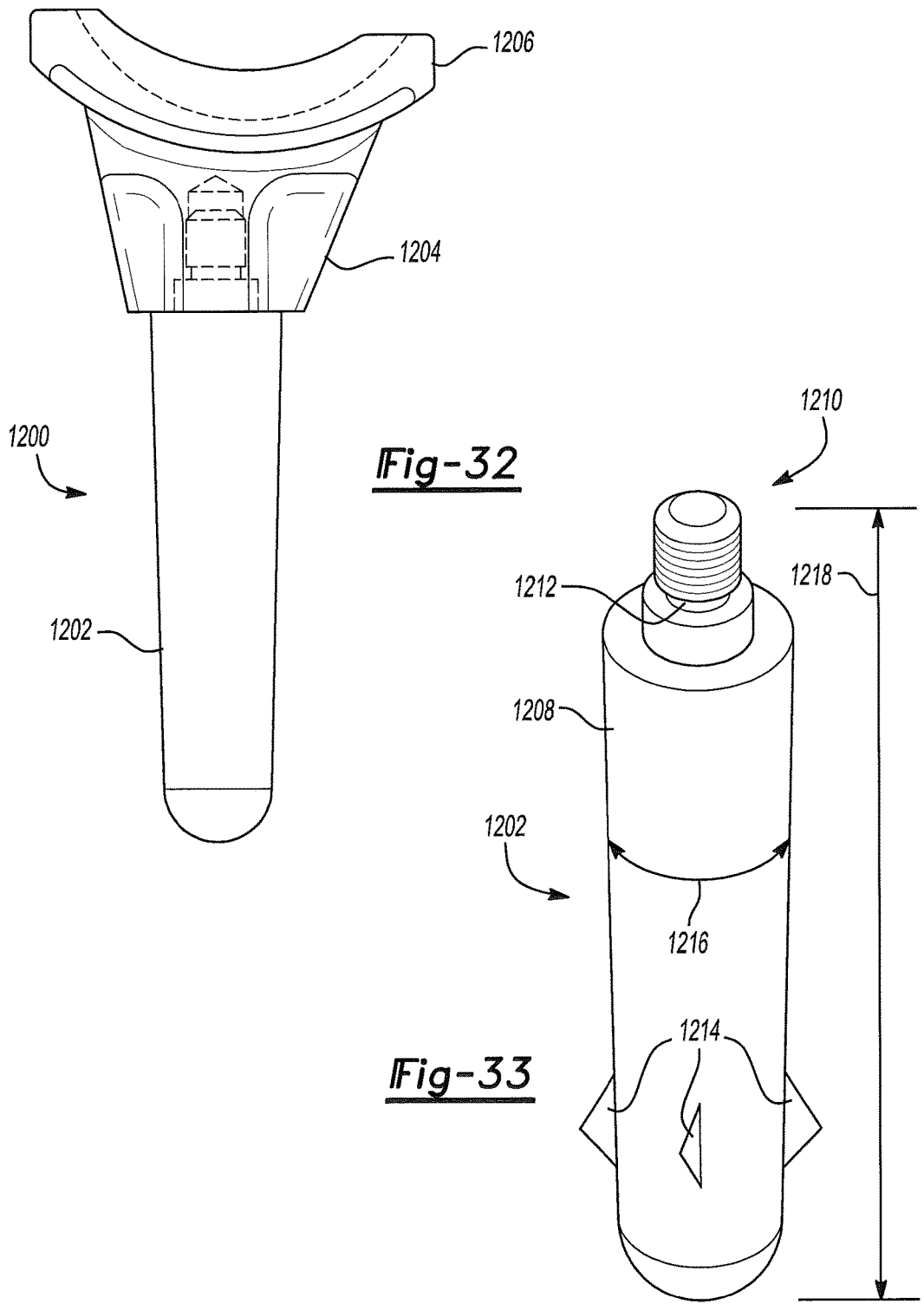

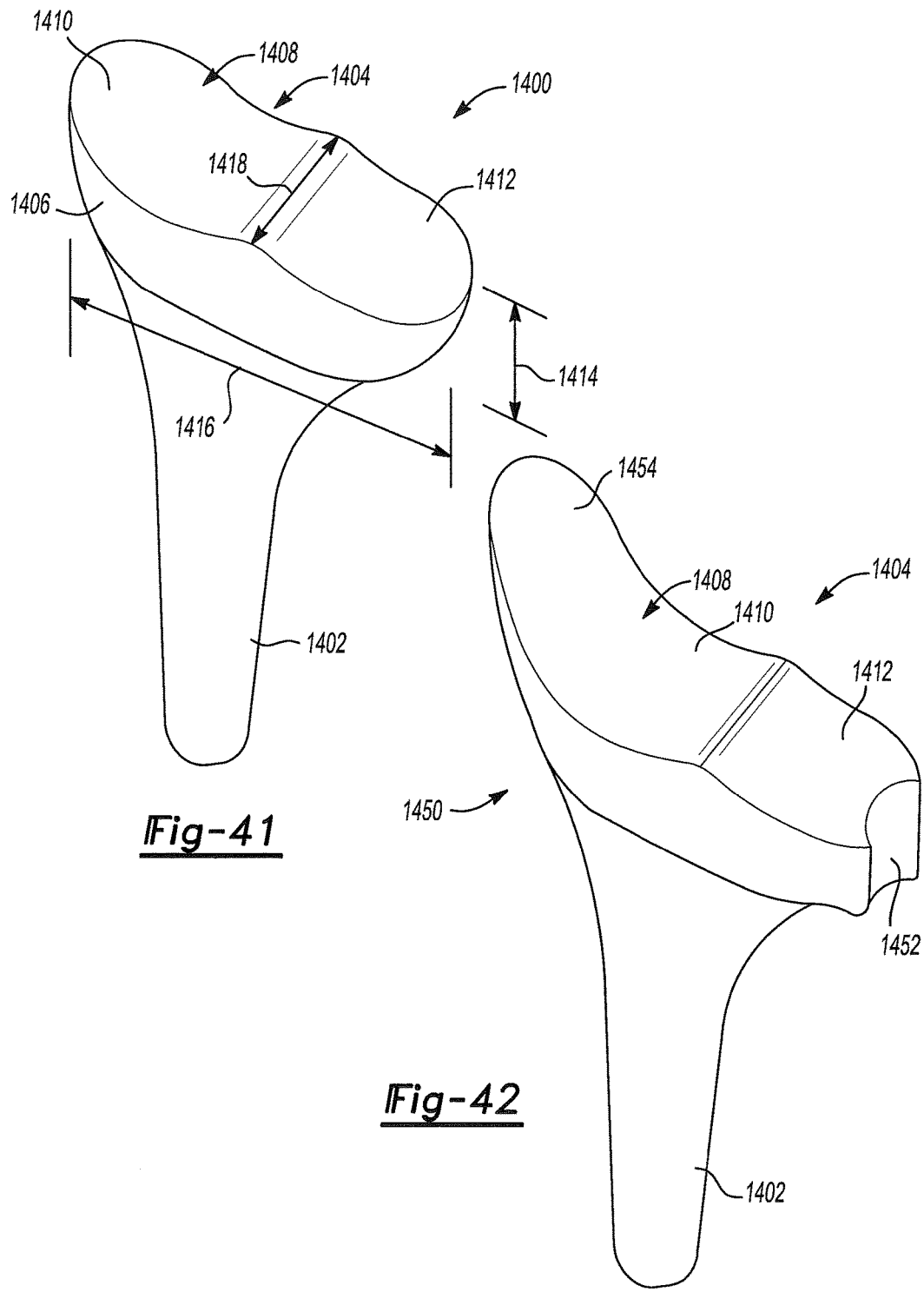

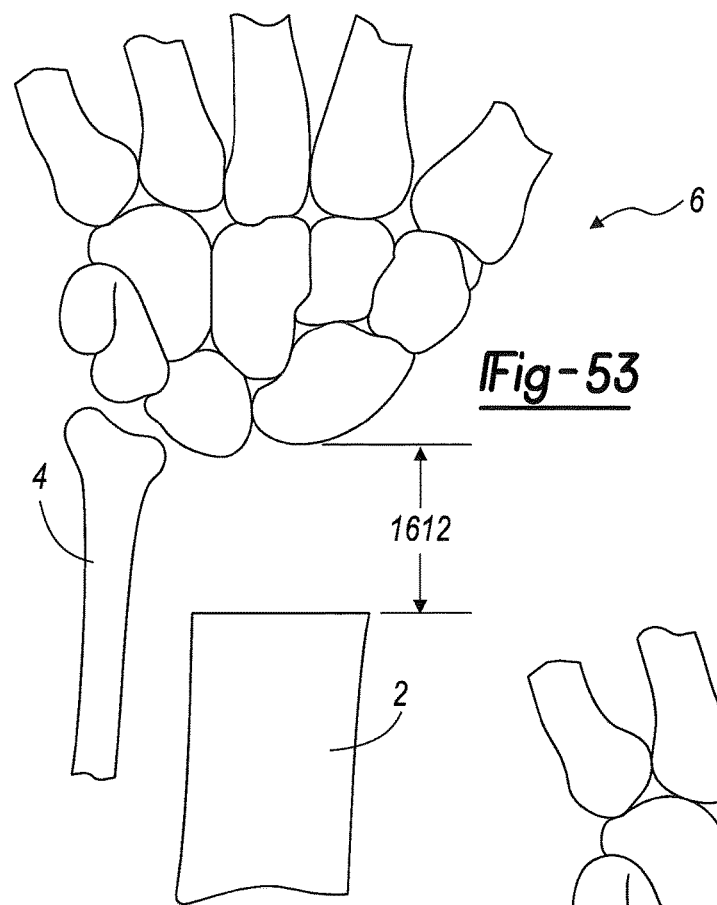
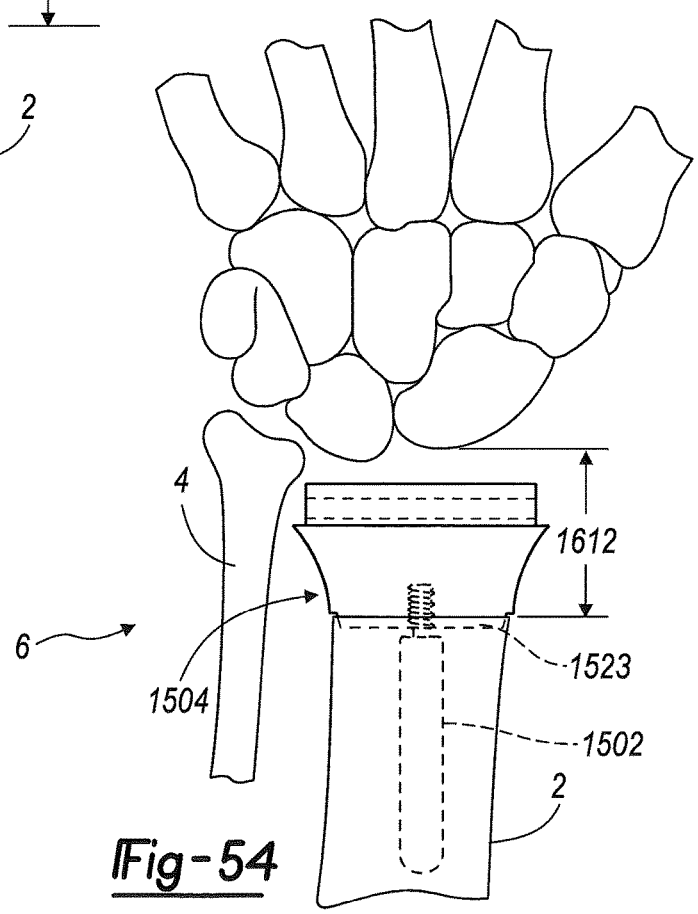

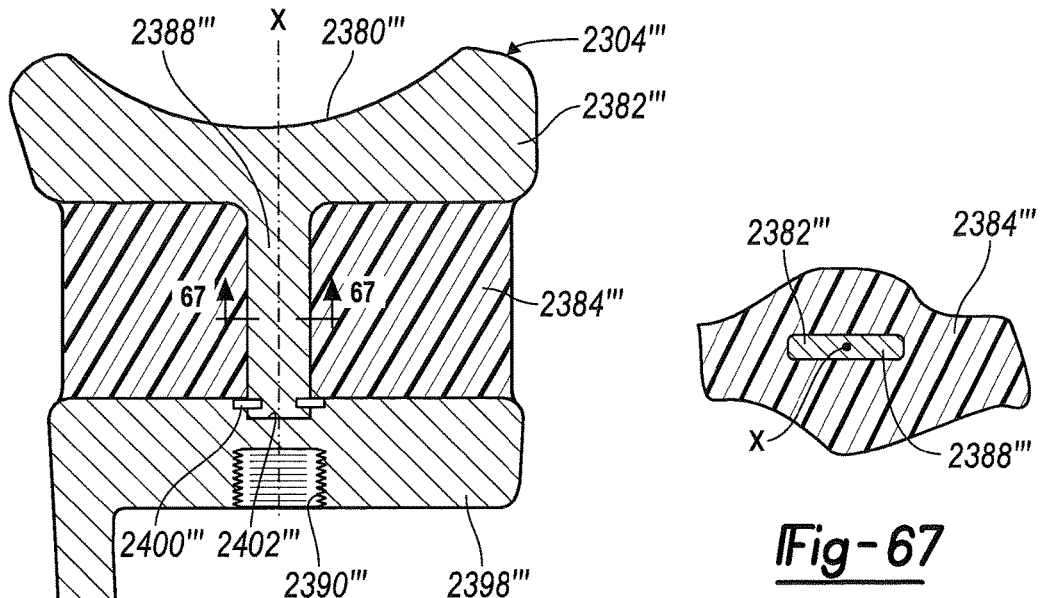
*Fig-66*
*Fig-67*
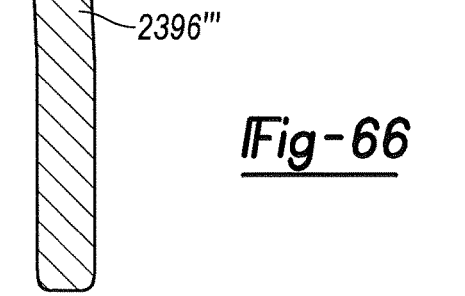
*Fig-68*
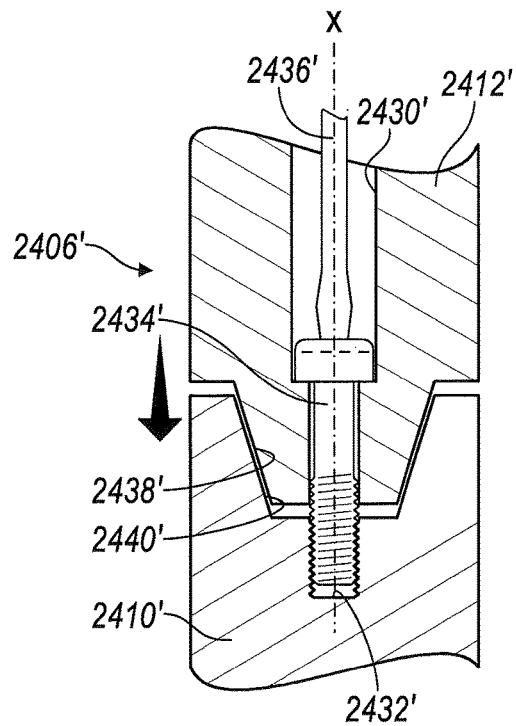
*Fig-69*

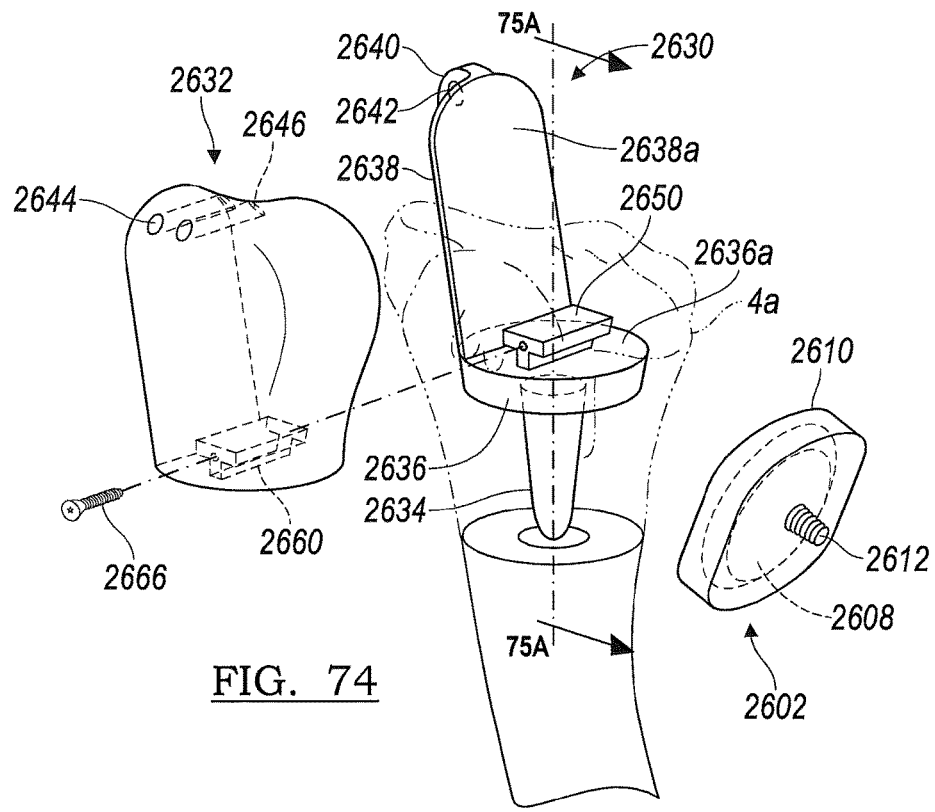
FIG. 74
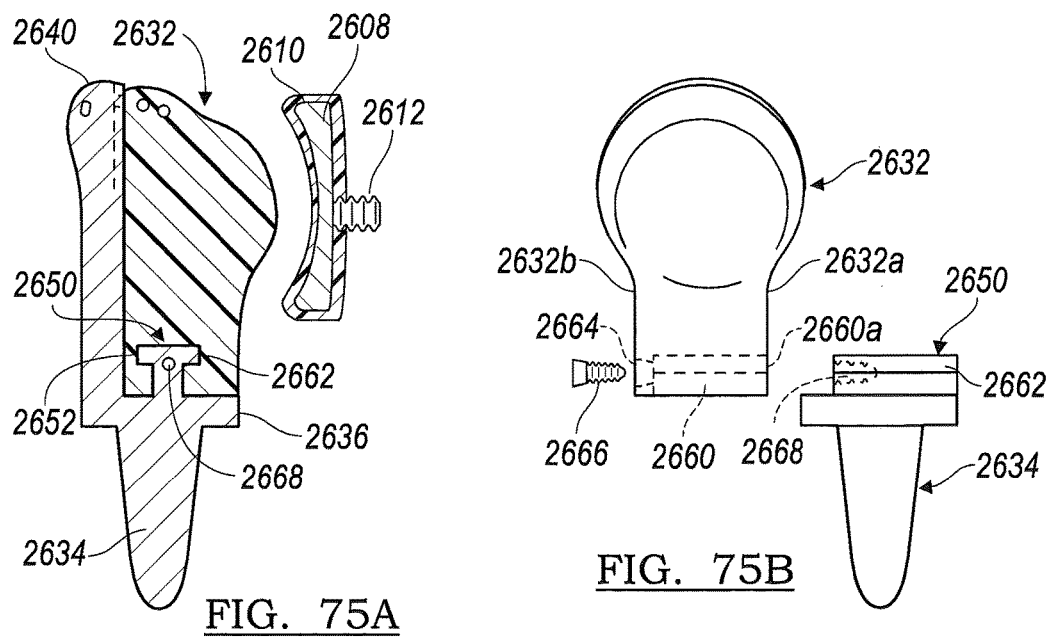
FIG. 75A
FIG. 75B

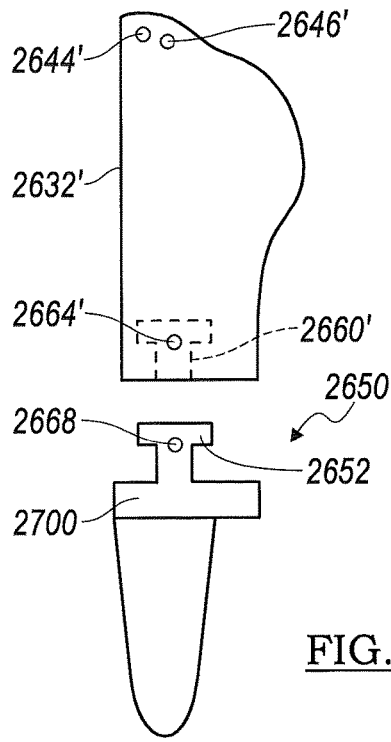
FIG. 78B
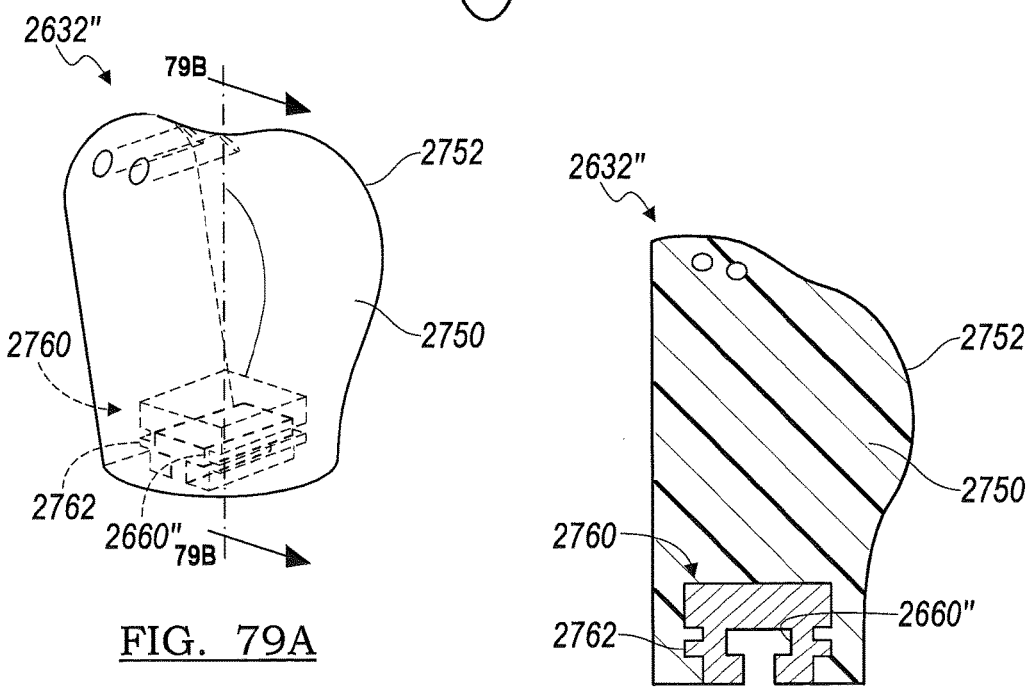
FIG. 79A
FIG. 79B

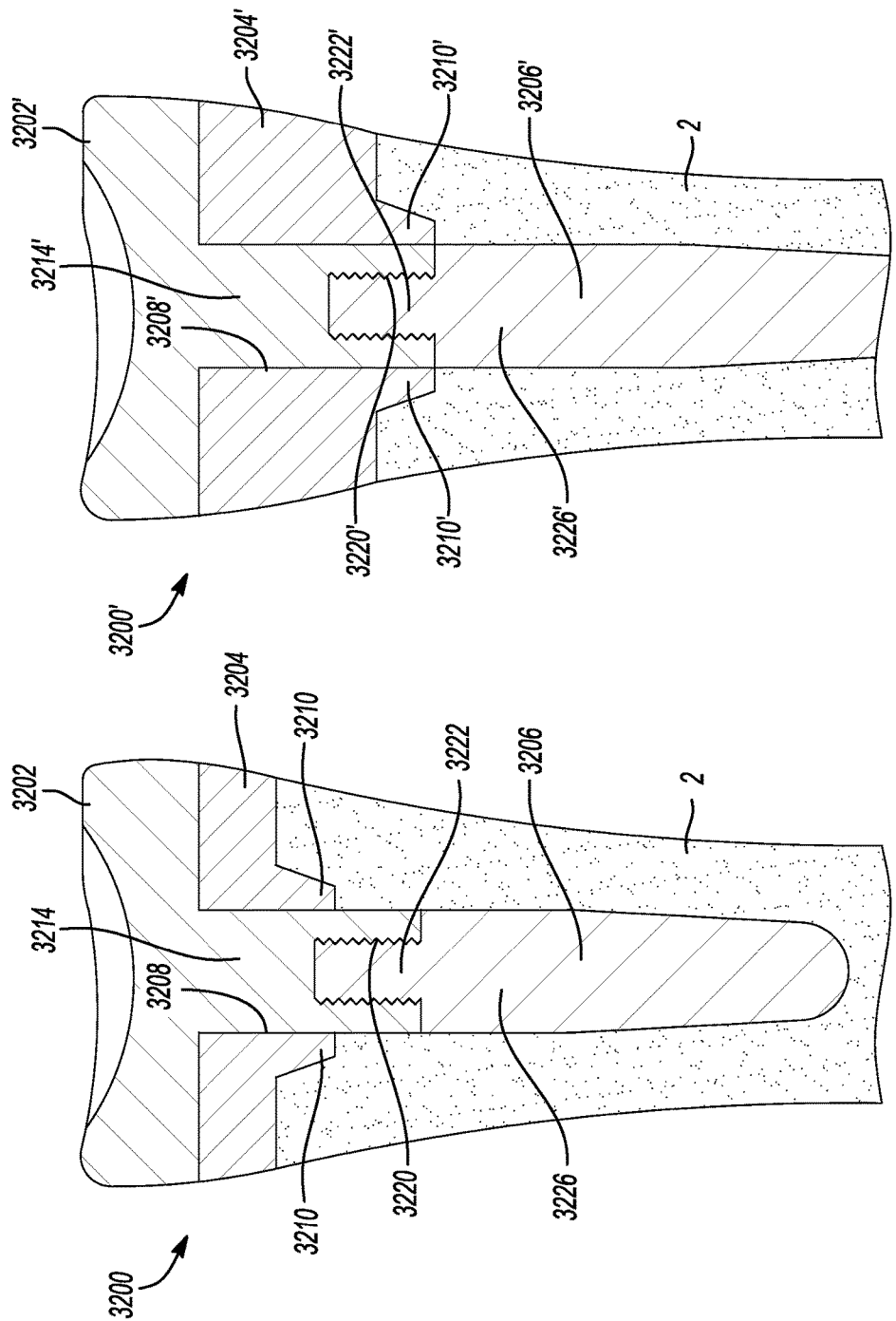

METHOD AND APPARATUS FOR WRIST ARTHROPLASTY

CROSS-REFERENCE TO RELATED APPLICATIONS

This application is a continuation of U.S. patent application Ser. No. 13/243,171, filed on Sep. 23, 2011; which is a continuation of U.S. patent application Ser. No. 12/576,844, filed on Oct. 9, 2009 (now U.S. Pat. No. 8,052,756); which is a continuation-in-part of U.S. patent application Ser. No. 12/562,692, filed on Sep. 18, 2009 (now U.S. Pat. No. 8,105,390); which is a continuation-in-part of U.S. patent application Ser. No. 12/553,350, filed on Sep. 3, 2009 (now U.S. Pat. No. 8,066,777); which is a continuation-in-part of U.S. patent application Ser. No. 12/389,919, filed on Feb. 20, 2009 (now U.S. Pat. No. 8,105,389); which is a continuation-in-part of U.S. patent application Ser. No. 11/867,884, filed on Oct. 5, 2007 (now U.S. Pat. No. 8,105,388); which is a continuation-in-part of U.S. patent application Ser. No. 11/517,537, filed on Sep. 7, 2006 (now U.S. Pat. No. 8,821,581); which is a continuation-in-part of U.S. patent application Ser. No. 11/260,729, filed on Oct. 27, 2005 (now U.S. Pat. No. 8,372,154); which is a continuation-in-part of U.S. patent application Ser. No. 10/862,821, filed on Jun. 7, 2004 (now U.S. Pat. No. 7,776,970); which is a continuation-in-part of U.S. patent application Ser. No. 10/279,240, filed on Oct. 24, 2002 (now U.S. Pat. No. 6,746,486). The disclosures of all of the above applications are incorporated herein by reference.

FIELD

The present teachings generally relate to prosthetic implants and more particularly to prosthetic wrist implants.

BACKGROUND

With reference to FIG. 1 of the drawings, the dorsal side of the bone structure of a patient's left hand and wrist is illustrated in conjunction with the radius 2 and the ulna 4. The bone structure includes a carpal bone complex 6 having a scaphoid 8, a lunate 10, a triquetrum 12, a pisiform 14, a trapezium 16, a trapezoid 18, a capitate 20 and a hamate 22. It will be appreciated that the scaphoid 8 and the lunate 10 bones articulate with the radius 2 during the movement of the wrist.

In a variety of wrist disorders, patients may experience discomfort, pain and difficulty in moving the wrist. Prior surgical treatment of this condition involved fusion to inhibit movement of the scaphoid 8 and the lunate 10 bones relative to the radius to thereby alleviate pain in the patient's wrist. This procedure, however, leaves the patient without motion in their wrist and thereby severely restricts the use of their wrist. Prosthetic wrist implants have been developed to provide a pair of artificial bearing surfaces for the wrist. Several of the prior wrist implants have suffered from drawbacks including limited range of motion and excessive bone resection. Others still provide proper motion only when aligned in an extremely precise manner relative to the carpal bone complex 6. While various jigs and fixtures may be employed to aid in the locating and forming of a hole in the distal portion of the carpal bone complex 6 for receiving a carpal implant, these devices typically do not completely eliminate the possibility of error in the alignment and forming of the hole.

Accordingly, there remains a need in the art for an improved prosthetic wrist implant that provides improved support and strength for the distal portion of the carpal bone complex 6 and which has a bearing surface whose orientation is changeable after implantation to provide the implanted prosthetic wrist with a range of motion that mimics the range of motion of a natural wrist.

SUMMARY

According to one particular aspect, the present disclosure provides a method of implanting a wrist prosthesis in a distal portion of an ulna for articulation at least near a radius and a carpal complex of a wrist joint. The method can include forming an incision near a distal portion of the radius and ulna joint. The method can also include resecting a distal portion of the ulna and positioning a stage member in a fixed position relative to the ulna. The method can further include sliding a bearing member relative to the stage member to hold the bearing member relative to the stage member and the distal ulna. The method can also include fixing the bearing member to a bearing fixation member extending from the stage member, and attaching soft tissue to at least one of the bearing member and the stage member.

According to another particular aspect, the present disclosure provides a method of implanting a wrist prosthesis in a distal portion of an ulna for articulation at least near a radius and a carpal complex of a wrist joint. The method can include forming an incision near the wrist joint and resecting a distal portion of the ulna. The method can also include positioning a stage member in a fixed position relative to the ulna, including passing a stem portion of the stage member in a first direction within an intramedullary canal of the ulna. The method can further include sliding a bearing member in a second direction, substantially perpendicular to the first direction, relative to the stage member to hold the bearing member relative to the stage member and the distal ulna. The method can also include attaching soft tissue to at least one of the bearing member and the stage member.

According to yet another particular aspect, the present disclosure provides a method of implanting a wrist prosthesis in a distal portion of an ulna for articulation at least near a radius and a carpal complex of a wrist joint. The method can include forming an incision near the wrist joint. The method can also include resecting a distal portion of the ulna and positioning a stage member in a fixed position relative to the ulna, including passing a stem portion of the stage member in a first direction within an intramedullary canal of the ulna. The method can further include sliding a bearing member in a second direction, substantially perpendicular to the first direction, relative to the stage member to hold the bearing member relative to the stage member and the distal ulna. The method can also include attaching soft tissue to at least one of the bearing member and the stage member.

Further areas of applicability of the present teachings will become apparent from the detailed description provided hereinafter. It should be understood that the detailed description and various examples, while indicating the various embodiments of the teachings, are intended for purposes of illustration only and are not intended to limit the scope of the teachings or the claims.

BRIEF DESCRIPTION OF THE DRAWINGS

Additional advantages and features of the present invention will become apparent from the subsequent description and the appended claims, taken in conjunction with the accompanying drawings, wherein:

FIG. 1 is a view of the dorsal side of a patient's left hand and wrist illustrating the bone structure of the hand and wrist in conjunction with the radius and the ulna;

FIG. 2 is a view of the dorsal side of a patient's left hand and wrist illustrating the implantation of a prosthetic wrist implant constructed in accordance with the teachings of the present invention;

FIG. 3 is an exploded view of a prosthetic wrist constructed in accordance with the teachings of the present invention;

FIG. 4 is a perspective view of a portion of the prosthetic wrist of FIG. 2 illustrating the carpal implant in greater detail;

FIG. 10 is a side elevation view of a carpal implant constructed in accordance with the teachings of a third embodiment of the present invention;

FIG. 11 is a side elevation view of a carpal implant constructed in accordance with the teachings of a fourth embodiment of the present invention;

FIG. 12 is a side elevation view of a carpal implant constructed in accordance with the teachings of a fifth embodiment of the present invention;

FIG. 13 is an exploded front elevation view of a portion of a prosthetic wrist constructed in accordance with the teachings of a sixth embodiment of the present invention;

FIG. 14 is a side elevation view of a portion of the prosthetic wrist of FIG. 13;

FIG. 32 is a distal radial implant according to various embodiments;

FIG. 33 is a stem portion of a distal radial implant according to various embodiments;

FIG. 41 is a perspective view of a distal radial implant according to various embodiments;

FIG. 42 is a perspective view of a distal radial implant according to various embodiments;

FIG. 53 is an environmental view of the portion of an anatomy resected for a bone replacement implant according to various embodiments;

FIG. 54 is an environmental view illustrating a positioning of a portion of an implant according to various embodiments;

FIG. 66 is a section view of another embodiment of the bone replacement member of the wrist prosthesis system of FIG. 62;

FIG. 67 is a section view of the bone replacement member taken along the line 67-67 of FIG. 66;

FIG. 68 is a section view of a stem of the wrist prosthesis system taken along the line 68-68 of FIG. 62;

FIG. 69 is a section view of another embodiment of the stem of the wrist prosthesis system;

FIG. 74 is an exploded perspective environmental view of a distal ulna and distal radial prosthesis;

FIG. 75A is a cross-sectional view of a distal ulna prosthesis;

FIG. 75B is a plan exploded view of a distal ulna prosthesis;

FIG. 78B is a plan exploded view of a distal ulna prosthesis;

FIG. 79A is a perspective view of a portion of a distal ulna prosthesis;

FIG. 79B is a cross-sectional view of a portion of a distal ulna prosthesis of FIG. 79A along line 79B-79B;

FIGS. 84 and 85 are anterior views of distal radial implants having articulation portions and body portions constructed with various dimensions;

DETAILED DESCRIPTION OF VARIOUS EMBODIMENTS

Figure 5:
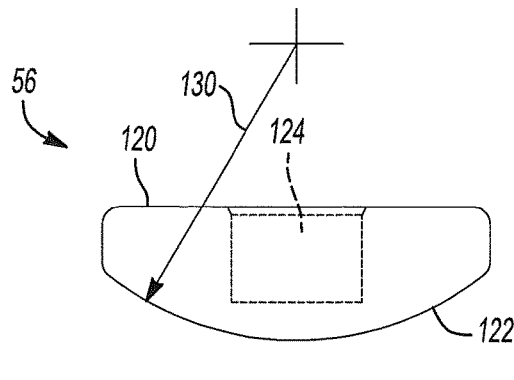
FIG. 5 is a side view of a portion of the prosthetic wrist of FIG. 2 illustrating the wrist bearing component in the coronal plane.

The following description of various embodiments is merely exemplary in nature and is not intended to limit the teachings, application, or uses of various embodiments.

With reference to FIGS. 2 and 3 of the drawings, a prosthetic wrist constructed in accordance with the teachings of the present invention is generally indicated by reference numeral 50. The prosthetic wrist 50 is illustrated in a post operative condition as implanted to a distal portion 2a of the radius 2 and a proximal portion 6a of the carpal bone complex 6. As those skilled in the art will appreciate, the distal portion 2a of the radius 2 and the proximal portion 6a of the carpal bone complex 6 are formed when the surgeon resects a portion of the radius 2 and the carpal bone complex 6 from the patient prior to implantation of the prosthetic wrist 50.

The prosthetic wrist is illustrated to include a radial implant 52, a carpal implant 54, a wrist bearing component 56 and a plurality of bone screws 58. The radial implant 52 includes a radial stem 60, which is configured to be implanted into a distal portion 2a of the radius 2, and a bearing guide 62, which is fixed to the distal end of the radial stem 60. The bearing guide 62 includes a bearing or concave guide surface 64 that is configured to engage in a mating manner the wrist bearing component 56. In the preferred embodiment, the radial implant 52 is unitarily formed from a titanium material, such as Ti-6Al-4V (F136), although those skilled in the art will understand that other materials having sufficient strength and biocompatibility may also be employed. Those skilled in the art will also understand that the radial implant 52 may be configured in a modular manner, wherein the radial stem 60 and the bearing guide 62 are discrete elements that are coupled together prior to or during the process of implantation. It will also be understood that the bearing guide 62 may be integrally formed or molded onto the radial implant 52 and formed of a selected material. For example, the bearing guide 62 may be formed of a polyethylene material or other polymer to be formed with the radial stem 60. Therefore the radial implant 52 may include a proximal radial stem on a distal radial portion over which the bearing guide portion 62 is formed. Nevertheless, as discussed above, the bearing guide portion 62 may be formed of any appropriate material such as a ceramic, or a metal including titanium and cobalt chromium molybdenum alloy.

With additional reference to FIGS. 3 and 4, the carpal implant 54 is illustrated to include a body 70, an ulnar flange 72 and a radial flange 74. The carpal implant 54 is unitarily formed from a titanium material, such as Ti-6Al-4V (F136), although those skilled in the art will understand that other materials having sufficient strength and biocompatibility may also be employed.

The body 70 includes a stem 80, a proximal stem 82 and an interconnecting flange 84. The stem 80, which is formed along a stem axis 86 and extends from the distal side of the body 70, is configured to be inserted into a hole formed in the capitate 20 (FIG. 2). The proximal stem 82 extends in a direction opposite the stem 80 and is sized to engage the wrist bearing component 56. In the particular embodiment illustrated, the proximal stem 82 is formed as a tapered cylinder having an axis 88 that is offset ulnarly from the stem axis 86. Those skilled in the art will appreciate, however, that the axis 88 of the proximal stem 82 may be coincident with the stem axis 86. The taper of the proximal stem 82 is configured to the profile of a conventional Morse taper for attachment to the wrist bearing component 56. A fillet radius R is employed to reduce the concentration of stress at the points at which the stem 80 and the proximal stem 82 are joined to the remainder of the body 70.

The interconnecting flange 84 couples the stem 80 to the ulnar flange 72. The interconnecting flange 84 includes an interconnecting bone abutment surface 90 that is skewed to the stem axis 86 by an angle that is less than 90 degrees in magnitude and which is preferably about 80 degrees to permit the interconnecting flange 84 to conform to the proximal end of the distal portion 6a of the carpal bone complex 6.

The ulnar flange 72 is coupled to a side of the interconnecting flange 84 proximate the stem 80 and has a lateral bone abutment surface 96 that is configured to abut an ulnar side of the hamate 22 and which projects upwardly from the body 70 in a manner that is skewed to both the stem axis 86 and the interconnecting bone abutment surface 90 by an angle of less than 90 degrees. A securing aperture 98a, which is formed in the distal end of the ulnar flange 72 along an axis that is generally perpendicular to the lateral bone abutment surface 96, is illustrated to include a first portion 100 and a second portion 102. Although it will be understood that a perpendicular aperture is not required. The first portion 100 of the securing aperture 98a has a spherical shape that is configured to matingly engage the frustoconical surface of the head 58a of a bone screw 58. (FIG. 3). The second portion 102 of the securing aperture 98a has a generally cylindrical shape that is sized to receive the body 58b of the bone screw 58.

In the particular embodiment illustrated, the ulnar bone abutment surface 96 is arranged at an angle of about 50 degrees relative to the stem axis 86. The distal end of the ulnar flange 72 terminates at an arcuate edge 104 that is defined by a radius that is centered at the centerpoint of the securing aperture 98a. As those skilled in the art will readily appreciate, however, the center of the radius need not be centered at the centerpoint of the securing aperture 98a.

The radial flange 74 is coupled to the body 70, and more specifically to the interconnecting flange 84, on a side opposite the ulnar flange 72 and includes a medial bone abutment surface 110 that is configured to abut a radial side of the distal portion 6a of the carpal bone complex 6 and which projects upwardly from the body 70 in a manner that is skewed to the stem axis 86 by an angle of less than 90 degrees. In the particular embodiment illustrated, the radial bone abutment surface 110 is skewed to the stem axis 86 by an angle of about 80 degrees. Like the ulnar flange 72, the radial flange 74 includes a securing aperture 98b and terminates at its distal end at an arcuate edge 112 that is defined by a radius that is centered at the centerpoint of the securing aperture 98b. The securing aperture 98b is substantially identical to the securing aperture 98a but is formed about an axis that is generally perpendicular to the radial bone abutment surface 110.

In view of the above discussion, those skilled in the art will appreciate that one general concept of the present invention is the provision of a carpal implant having radial and ulnar flanges that are configured to abut portions of the carpal bone complex (whether resected or not) in a way that supports the bones of the radial and ulnar sides of the carpal bone complex. Accordingly, those skilled in the art will appreciate that the carpal implant of the present invention may be formed in any generally concave manner (i.e., wherein at least a portion of each of the radial and ulnar flanges is skewed to the axis of the body) that is configured to abut the radial and ulnar sides of the carpal bone complex (whether resected or not). Other examples of the "concave" formation of the carpal implant of the present invention are illustrated in FIGS. 10 through 12 and 15 through 27 and will be described in detail below.

Figure 6:
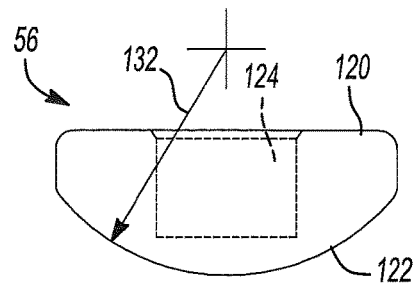
FIG. 6 is a side view of a portion of the prosthetic wrist of FIG. 2 illustrating the wrist bearing component in the sagittal plane.

With renewed reference to FIGS. 2 and 3 and additional reference to FIGS. 5 and 6, the wrist bearing component 56 has the general shape of an ellipsoidal segment and includes a generally flat abutting edge 120 and a wrist bearing surface 122. As those skilled in the art will appreciate, the wrist bearing surface 122 does not extend to a point where it intersects the abutting edge 120 as this would cause the wrist bearing component 56 to be too large in size. Accordingly, the flat sides at which the wrist bearing surface 122 terminates permit the wrist bearing surface 122 to be shaped in a desired manner while maintaining proper sizing of the wrist bearing component 56. A securing feature 124 is formed into or otherwise coupled to the abutting edge 120 to permit the wrist bearing component 56 to be secured to the proximal end of the carpal implant 54. In the particular example provided, the securing feature 124 is a blind tapered hole that is configured to matingly engage the proximal stem 82. Those skilled in the art will readily understand, however, that any appropriate coupling means may be employed to couple the wrist bearing component 56 to the carpal implant 54 and as such, the scope of the present invention will not be so limited as to require the coupling of the wrist bearing component 56 and the carpal implant 54 through the engagement of a tapered stem with a tapered hole. As those skilled in the art will appreciate, the modular nature of the wrist bearing component 56 permits the surgeon to select from a variety of wrist bearing components 56 that are differently sized and/or shaped to permit the surgeon to tailor the prosthetic wrist 50 to the individual needs of the patient. Those skilled in the art will also appreciate that the surgeon's selection of a particular wrist bearing component 56 may necessitate the use of a particular radial implant 52 that has a correspondingly different size and/or configuration.

The wrist bearing component 56 is preferably formed from a cobalt chromium alloy, such as CoCrMo, which provides fatigue and corrosion resistance, as well as a relatively high degree of strength. Those skilled in the art will understand that other appropriate materials, including metals and/or plastics, may alternatively be employed to form the wrist bearing component 56 or a portion thereof, which includes the wrist bearing surface 122.

With particular reference to FIGS. 5 and 6, the wrist bearing surface 122 is illustrated as being defined by a first radius 130 in the coronal plane and a second radius 132 in the sagittal plane. Preferably, the first and second radii 130 and 132 are different and more preferably, the first radius 130 is larger than the second radius 132. Configuration of the wrist bearing component 56 in this manner permits the prosthetic wrist 50 to move in a manner that more closely approximates the motion of a natural wrist.

Figure 7:
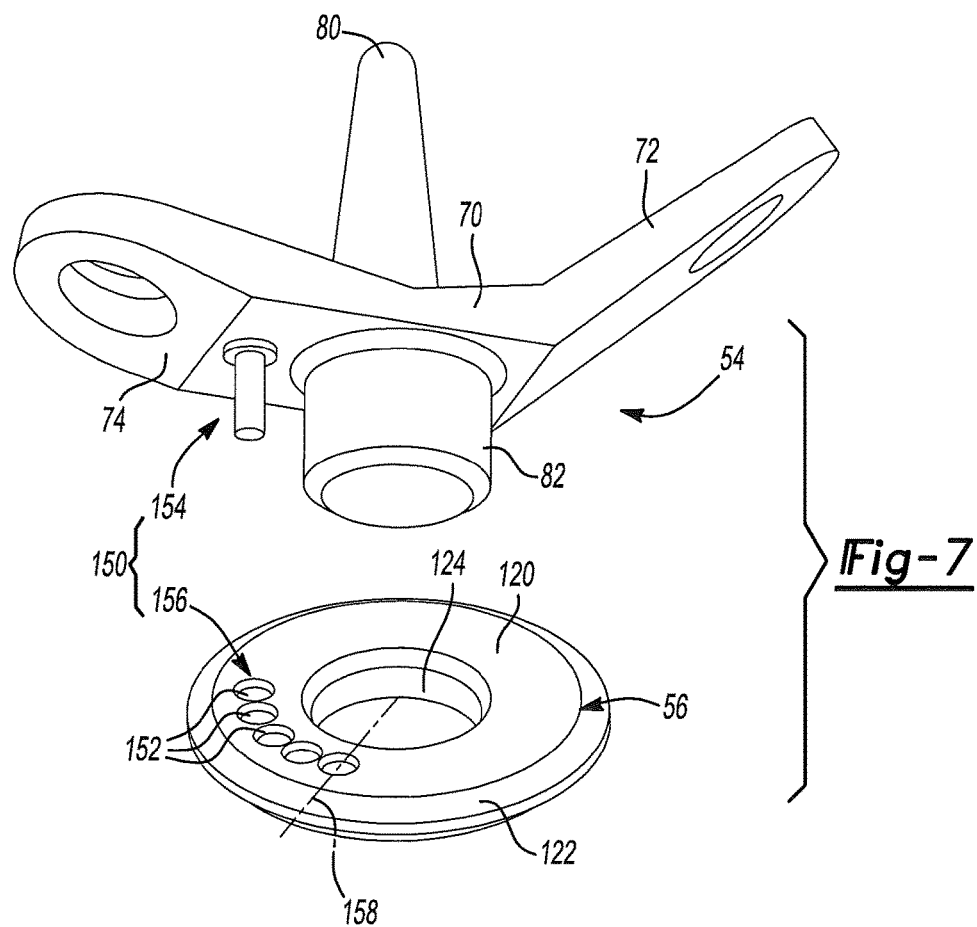
FIG. 7 is an exploded perspective view of a prosthetic wrist similar to that of FIG. 2 but additionally including an alignment mechanism for radially fixing the wrist bearing component relative to the carpal implant.

In situations where the wrist bearing surface 122 is contoured in a manner that is not defined by a single spherical radius, the orientation of the wrist bearing component 56 relative to the radial implant 52 is critical. Accordingly, the prosthetic wrist 50 preferably also includes an alignment mechanism 150 in such situations for radially fixing the wrist bearing component 56 relative to the carpal implant 54 as is illustrated in FIG. 7. Preferably, the alignment mechanism 150 permits the surgeon implanting the prosthetic wrist 50 to orient the wrist bearing surface 122 to a predetermined installation orientation that is dependent upon the orientation between the implanted carpal implant 54 and the implanted radial implant 52. For example, if the radial implant 52 were to be fixed to the distal portion 2a of the radius 2 in a manner that was rotated slightly from that which was considered "nominal", the surgeon may be able to compensate for the slight radial offset by rotating the wrist bearing component 56 relative to the carpal implant 54 in an equivalent manner.

The alignment mechanism 150 may permit the wrist bearing component 56 to be rotated in an infinite number of positions relative to the carpal implant 54, as would the connection of the wrist bearing component 56 to the carpal implant 54 through the Morse taper connection of the proximal stem 82 and the blind tapered hole of the securing feature 124, or through adhesives, or recessed screws that extend through the wrist bearing component 56 and which engage the body 70 of the carpal implant 54 (not illustrated).

In the particular example provided, the alignment mechanism 150 permits the wrist bearing component 56 to be rotated into one of a plurality of predetermined orientations 152. In this regard, the alignment mechanism 150 is illustrated to include a coupling member 154, which is coupled to the carpal implant 54, and a plurality of holes 156 that are formed into the wrist bearing component 56. Each of the holes 156 is sized to receive the coupling member 154 and is defined by a centerline 158 that is spaced circumferentially apart from the centerline 158 of an adjacent hole 156. Rotation of the wrist bearing component 56 relative to the carpal implant 54 is accomplished via engagement of the coupling member 154 into an associated one of the holes 156 that permits the wrist bearing component 56 to be placed in the installation orientation relative to the radial implant 52. Those skilled in the art will understand that the coupling member 154 may be removably coupled to the carpal implant 54 so as to provide the surgeon with an option not to use the coupling member 154 should the surgeon need more flexibility in positioning the wrist bearing component 56 relative to the carpal implant 54. Those skilled in the art will also understand that the coupling member 154 and the holes 156 may be reversed (i.e., the coupling member 154 may be attached to the wrist bearing component 56 and the holes 156 may be formed in the carpal implant 54).

In another preferred form, the present invention provides a method for implanting a prosthetic wrist 50 between the radius 2 and the portion 6a of the carpal bone complex 6 of a patient. The method includes: providing a carpal implant 54 including a body 70, a ulnar flange 72 and a radial flange 74, the body 70 having a stem 80 that is arranged along an axis 86, the ulnar flange 72 being coupled to the body 70 and extending therefrom, the ulnar flange 72 having a lateral bone abutment surface 96, at least a portion of the lateral bone abutment surface 96 being skewed to the axis 86 of the stem 80 by an angle of less than 90 degrees, the radial flange 74 being coupled to the body and extending therefrom on a side opposite the ulnar flange 72, the radial flange 74 having a medial bone abutment surface 110, each of the ulnar and radial flanges 72 and 74 having a bone screw aperture 98a, 98b, respectively, formed therethrough; resectioning the carpal bone complex 6 along lines that are skewed to an axis of the capitate 20 and which correspond to the distal faces of the ulnar and radial flanges 72 and 74 and the interconnecting flange 84; forming an opening in the capitate 20 that lies along an axis that is generally coincident with the axis of the capitate 20; forming a pair of securing apertures 160 (FIG. 2) into the distal portion 6a of the carpal bone complex 6, one of the pair of securing apertures 160 being formed in the hamate 22; securing the carpal implant 54 to the distal portion 6a of the carpal bone complex 6 such that the stem 80 is at least partially disposed in the opening in the capitate 20 and engaged to the capitate 20; providing a first and second screws 58, the first and second screws 58 being appropriately sized to the pair of securing apertures 160 and the bone screw apertures 98a, 98b; placing the first screw through the bone screw aperture 98a in the ulnar flange 72 and the securing aperture 160 in the hamate 22 and securing the first screw to the hamate 22 to bring the lateral bone abutment surface 96 into abutment with an ulnar side of a hamate 22; and placing the second screw 58 through the bone screw aperture 98b in the radial flange 74 and the other securing aperture 160 in the distal portion 6a of the carpal bone complex 6 and securing the second screw 58 to the distal portion 6a of the carpal bone complex 6 to bring the medial bone abutment surface 110 into abutment with a radial side of the distal portion 6a of the carpal bone complex 6.

Preferably, the method also includes: providing a wrist bearing component 56 having a wrist bearing surface 122 that is defined by a first radius 130 in the coronal plane and a second, different radius 132 in the sagittal plane; coupling the wrist bearing component 56 to a proximal stem 82 formed on the body 70 of the carpal implant 54 such that the wrist bearing component 56 is rotatable relative to the carpal implant 54; and fixing the wrist bearing component 56 to the proximal stem 82 such that the wrist bearing component 56 is aligned at a predetermined installation orientation relative to the distal portion 6a of the carpal bone complex 6.

Figure 8:
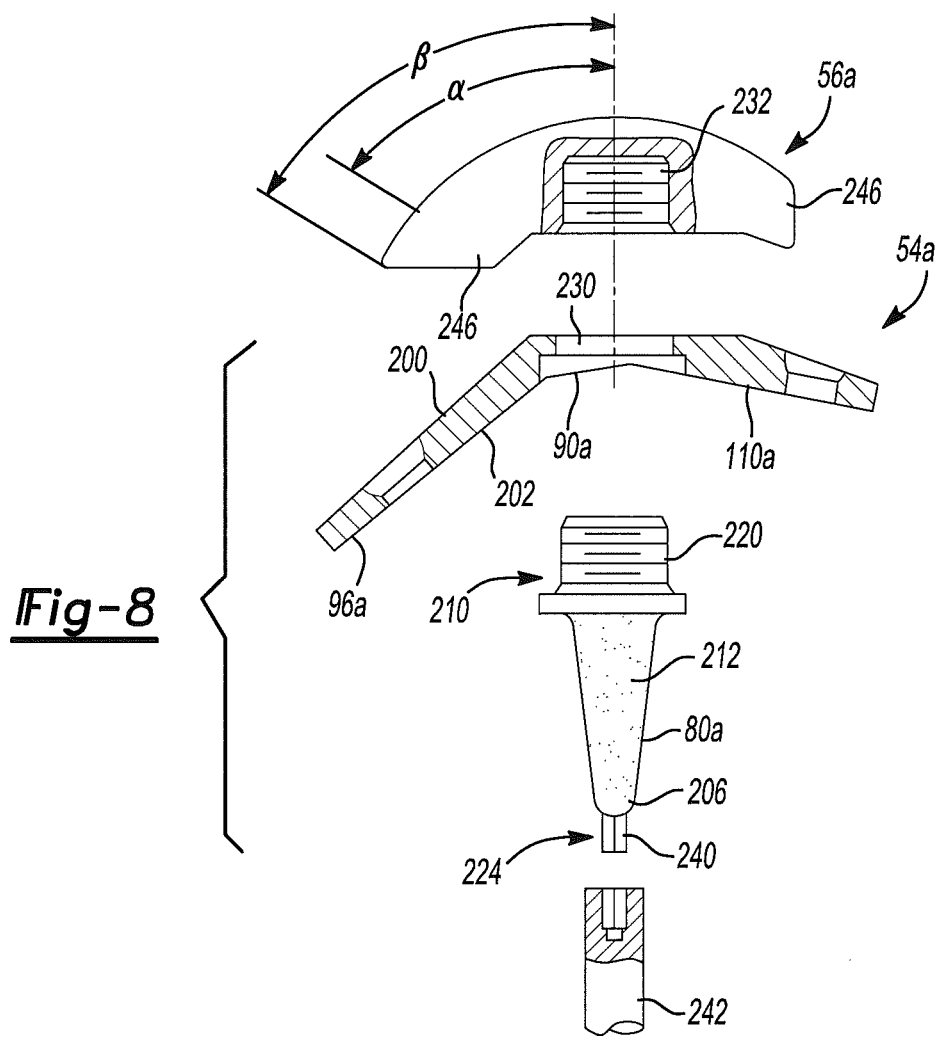
FIG. 8 is an exploded view in partial section of a prosthetic wrist constructed in accordance with the teachings of a second embodiment of the present invention.

While the carpal implant 54 has been described thus far as being unitarily formed and used in conjunction with a discrete wrist bearing component 56, those skilled in the art will appreciate that the invention, in its broader aspects, may be constructed somewhat differently. For example, the carpal implant 54a may be configured to include a discrete flange structure 200 and a discrete stem 80a as illustrated in FIG. 8. The flange structure 200 is unitarily formed from a suitable material, such as CoCrMo, and includes a bone abutment surface 202. In the particular example provided, the bone abutment surface 202 is shown to include an interconnecting, lateral and medial bone abutment surfaces 90a, 96a and 110a, respectively, which mimic the configurations of the interconnecting, lateral and medial bone abutment surfaces 90, 96, 110 (FIG. 3), respectively.

The stem 80a is illustrated to include a tapered cylindrical portion 206, which is configured to be fitted to a hole that is formed in the capitate 20 (FIG. 2), and a connecting portion 210 for coupling the stem 80a to the flange structure 200. The tapered cylindrical portion 206 is generally similar to the stem 80 (FIG. 3) discussed above and includes a porous coating 212. The coating 212 or surface may also be plasma sprayed or roughened to form an uneven or unsmooth surface and need not be porous.

In the example provided, the connecting portion 210 includes a threaded end portion 220, which is coupled to a proximal end of the tapered cylindrical portion 206, and a driving portion 224, which is coupled to an end of the tapered cylindrical portion 206 opposite the threaded end portion 220. The threaded end portion 220 is configured to extend through a stem receiving aperture 230 that is formed in the flange structure 200 and threadably engage a threaded aperture 232 that is formed in the wrist bearing component 56a. The driving portion 224 is illustrated to include a geometric feature, such as a male hexagon shank 240, that permits the stem 80a to be rotated with an appropriately configured tool 242 such that the threaded end portion 220 threadably engages the threaded aperture 232 in the wrist bearing component 56a. Those skilled in the art will readily understand that the driving portion 224 may be of any shape (e.g., triangular, square, Torx®) and may extend from the tapered cylindrical portion 206 in the form of a shank, or be recessed into the tapered cylindrical portion 206, in which case the tool 242 would have a corresponding male end to engage the driving portion 224, rather than a corresponding female as illustrated in this example.

With the exception of the threaded aperture 232 and a pair of anti-rotation tabs 246, the wrist bearing component 56a is otherwise identical to the wrist bearing component 56 of FIG. 2. The anti-rotation tabs 246 are configured to abut a proximal side of the flange structure 200 when the wrist bearing component 56a is coupled to the carpal implant 54a to thereby inhibit relative rotation between the wrist bearing component 56a and the carpal implant 54a. Those skilled in the art will appreciate, however, that other anti-rotation means may additionally or alternatively be incorporated into wrist bearing component 56a and/or the carpal implant 54a, including mating geometric features (e.g., a male hex protrusion formed onto the proximal side of the flange structure 200 and a mating hex recess formed into the distal side of the wrist bearing component 56a), fasteners and pins. The use of anti-rotation tabs 246 provides the wrist bearing component 56 with a relatively greater range of motion as comparatively illustrated by the angles $\alpha$ and $\beta$.

Figure 9:
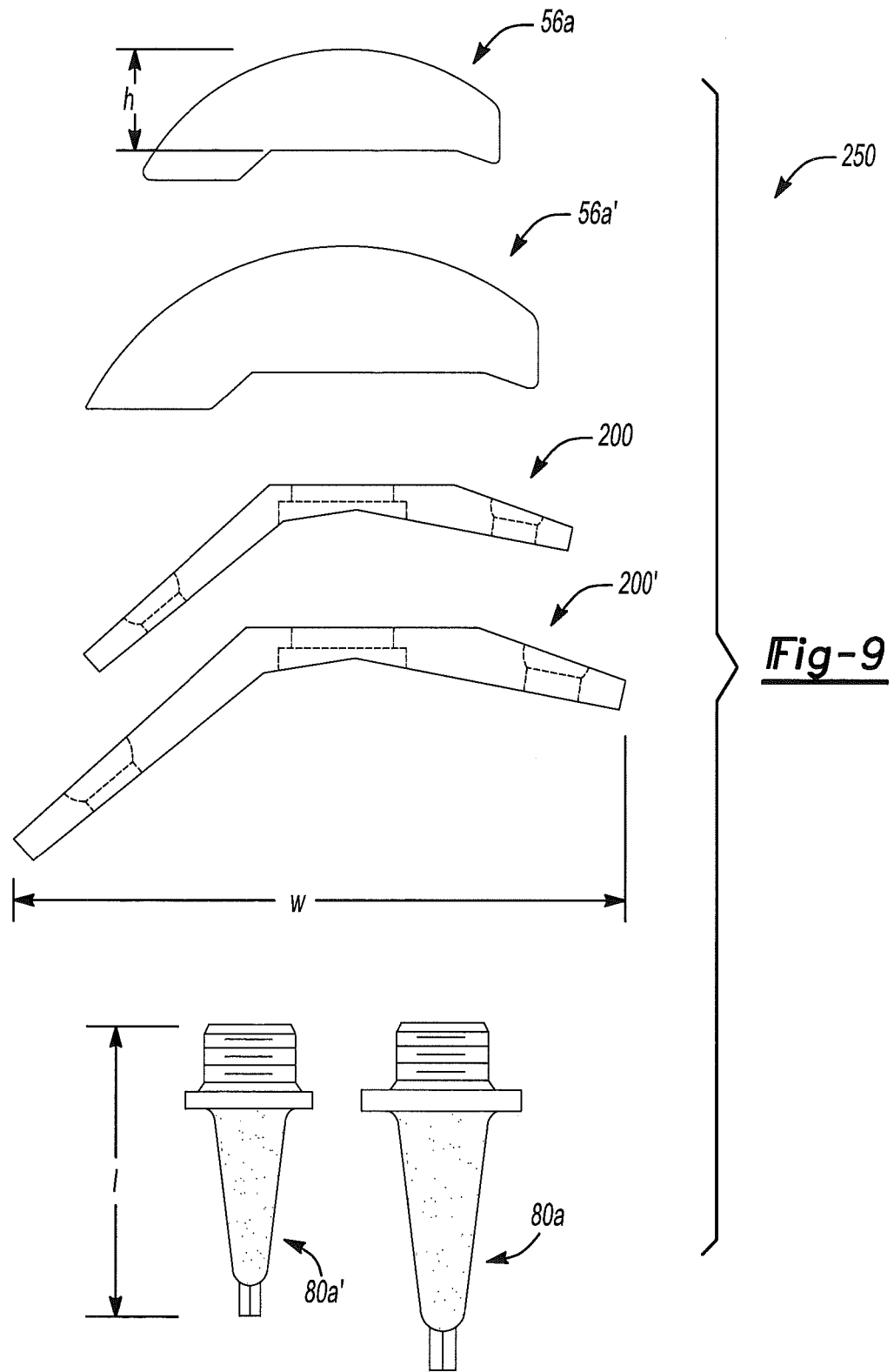
FIG. 9 is a view of a kit that utilizes the prosthetic wrist of FIG. 8.

The modular configuration described above provides the surgeon with a relatively high degree of flexibility when differently sized components are available in a kit form as shown in FIG. 9. In the example illustrated, several wrist bearing components (i.e., wrist bearing components 56a and 56a'), several flanges (i.e., flanges 200 and 200') and several stems (i.e., stems 80a and 80a') are provided in a kit 250. The wrist bearing components 56a and 56a' are configured with an identical articular shape, but vary in their overall height dimension h. Similarly, the flanges 200 and 200' and stems 80a and 80a' are similarly configured, but vary proportionally to achieve a desired overall width, w, and/or length, l, for example.

In the embodiments of FIGS. 10 and 11, the carpal implants 54b and 54c are generally similar to the carpal implant 54 (FIG. 3), except for the configuration of the interconnecting, ulnar and radial flanges. In FIG. 10, the ulnar and radial flanges 72b and 74b, respectively, intersect one another and as such, this embodiment lacks the interconnecting flange 84 of the carpal implant 54. The ulnar flange 72b is shown to be configured such that the lateral bone abutment surface 96b is skewed to the stem axis 86 by an angle of about 30 degrees, while the radial flange 74b is shown to be configured such that the medial bone abutment surface 110b is skewed to the stem axis 86 by an angle of about 45 degrees. In FIG. 11, the interconnecting flange 84c is configured such that the interconnecting bone abutment surface 90c is accurately shaped. In the particular example provided, the interconnecting bone abutment surface 90c is tangent to the lateral and medial bone abutment surfaces 96c and 110c, respectively.

A further embodiment is illustrated in FIG. 12, wherein the carpal implant portion 54d and the wrist bearing portion 56d are unitarily formed from a suitable material, such as CoCrMo. In the particular embodiment illustrated, the carpal implant portion 54d is illustrated to include ulnar and radial flanges 72d and 74d, respectively, that intersect one another in a manner that is similar to the ulnar and radial flanges 72b and 74b, respectively, of the carpal implant 54b of FIG. 10. Those skilled in the art will appreciate, however, that the ulnar and radial flanges 72d and 74d may be formed differently so as to intersect at any desired angle, or such that they are spaced apart by an interconnecting portion in a manner that is similar, for example, to the configurations of the carpal implants 54 and 54c of FIGS. 3 and 11, respectively.

A sixth embodiment is illustrated in FIGS. 13 and 14, and illustrates an alternately constructed radial implant 52e, wherein the bearing guide 62e is formed with an arcuate shape that is configured to matingly engage the curvilinear cut 300 of a resected radius 2a'. Those skilled in the art will appreciate that the curvilinear cut 300 will support the bearing guide 62e and thereby permit the radial implant 52e to be formed with a relatively lower profile as compared to the radial implant 52.

Figure 15:
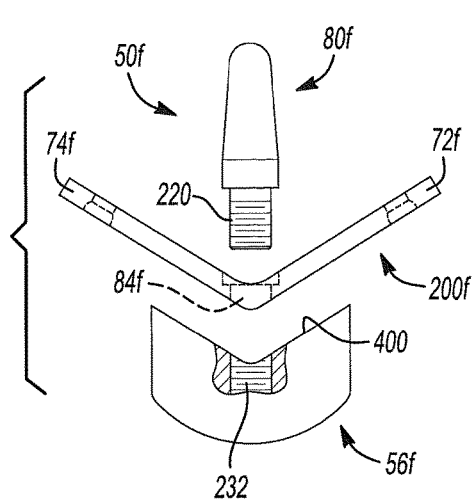
FIG. 15 is an exploded side elevation view of a prosthetic wrist constructed in accordance with the teachings of a seventh embodiment of the present invention.

A seventh embodiment is illustrated in FIG. 15, wherein the prosthetic wrist 50f is illustrated to be generally similar to the prosthetic wrist illustrated in FIG. 8, except for the shape of the flange structure 200f and the wrist bearing component 56f. More specifically, the flange structure 200f includes a generally V-shaped interconnecting flange 84f to which the ulnar and radial flanges 72f and 74f, respectively, are oppositely coupled. As will be apparent to those skilled in the art, the wrist bearing component 56f is contoured to matingly engage the proximal side of the flange structure 200f and accordingly includes a generally V-shaped profile 400. In a manner that is similar to the prosthetic wrist of FIG. 8, the stem 80f includes a threaded end portion 220 that is threadably received into a threaded aperture 232 that is formed in the wrist bearing component 56f.

Figure 16:
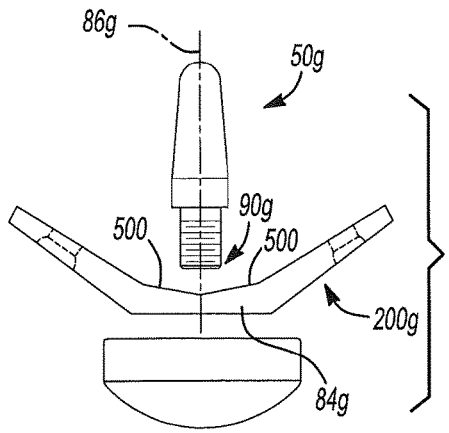
FIG. 16 is an exploded side elevation view of a prosthetic wrist constructed in accordance with the teachings of an eighth embodiment of the present invention.

An eighth embodiment is illustrated in FIG. 16, which is similar to the prosthetic wrist of FIG. 8 except for the flange structure 200g. The flange structure 200g of the prosthetic wrist 50g includes an interconnecting flange 84g with an interconnecting bone abutment surface 90g with a plurality of portions 500 that are each defined by a skew angle. The skew angles that define each portion 500 need not be symmetrical about the stem axis 86g. The skew angle of each portion 500 is less than 90 degrees in magnitude to permit the interconnecting flange 84g to conform and abut the proximal end of the distal portion 6a (FIG. 2) of the carpal bone complex 6 (FIG. 2).

Figure 17:
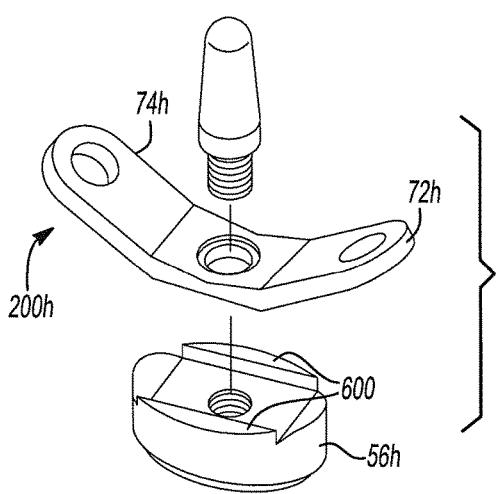
FIG. 17 is an exploded perspective view of a prosthetic wrist constructed in accordance with the teachings of a ninth embodiment of the present invention.
Figure 18:
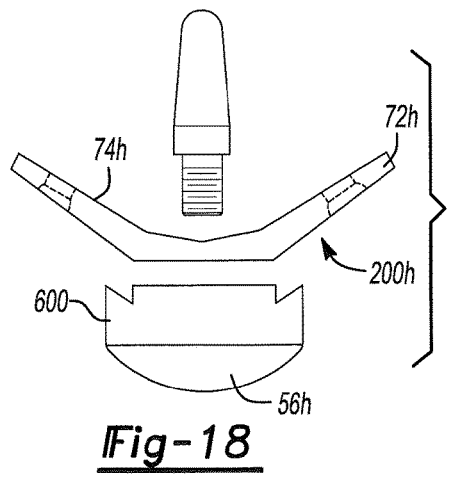
FIG. 18 is an exploded side elevation view of the prosthetic wrist of FIG. 17.

A ninth embodiment is illustrated in FIGS. 17 and 18. The flange structure 200h is generally identical to the flange structure 200g and as such, will not be discussed in further detail. The wrist bearing component 56h is generally similar to the wrist bearing component 56a (FIG. 8) in that the ulnar (lateral) and radial (medial) portions of the distal side of the wrist bearing component 56h are angled to match the angled proximal surfaces of the ulnar and radial flanges 72h and 74h, respectively. However, the wrist bearing component 56h also includes anterior and posterior located portions 600 on the distal sides of the wrist bearing component 56h that extend distally in a manner that overlaps the flange structure 200h. The configuration of the wrist bearing component 56h therefore inhibits both relative rotation and relative anterior-posterior movement between the wrist bearing component 56h and the flange structure 200h.

Figure 19:
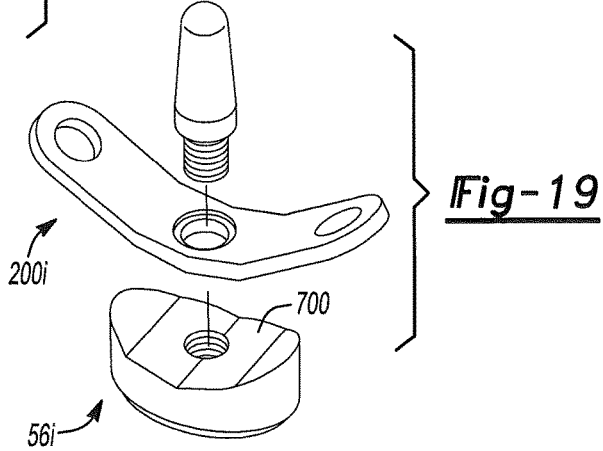
FIG. 19 is an exploded perspective view of a prosthetic wrist constructed in accordance with the teachings of a tenth embodiment of the present invention.
Figure 20:
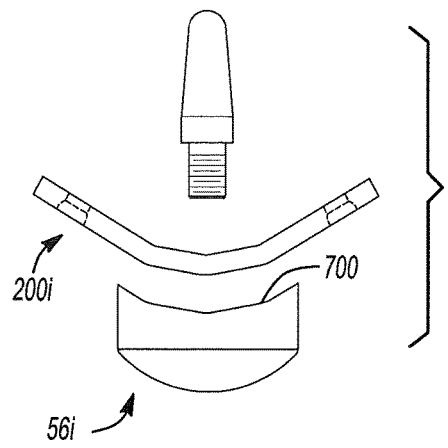
FIG. 20 is an exploded side elevation view of the prosthetic wrist of FIG. 19.

A tenth embodiment, which is also similar to the prosthetic wrist 50g, is illustrated in FIGS. 19 and 20. In this embodiment, the flange structure 200i is similar to the flange structure 200g except that the proximal side of the flange structure 200i is parallel to the distal side of the flange structure 200i (i.e., the proximal side of the flange structure 200i includes a plurality of segments that are parallel to the segments that make up the distal side of the flange structure 200i). As will be apparent to those skilled in the art, the wrist bearing component 56i is contoured to matingly engage the proximal side of the flange structure 200i and accordingly includes a profile 700 that matches the four angled surfaces that make up the proximal side of the flange structure 200i.

Figure 21:
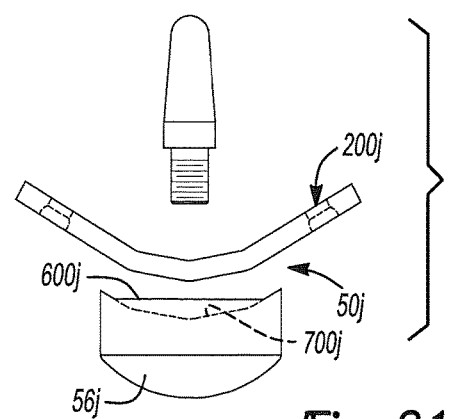
FIG. 21 is an exploded side elevation view of a prosthetic wrist constructed in accordance with the teachings of an eleventh embodiment of the present invention.
Figure 22:
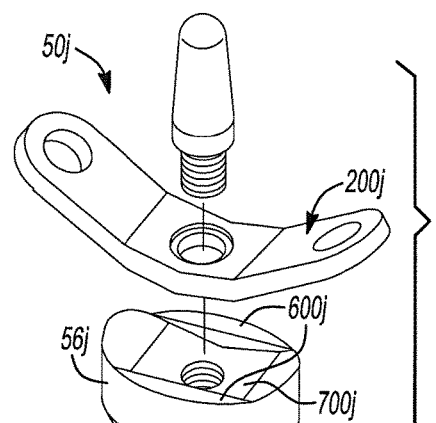
FIG. 22 is an exploded side perspective view of the prosthetic wrist of FIG. 21.

An eleventh embodiment is illustrated in FIGS. 21 and 22, wherein the prosthetic wrist 50j is illustrated to include a flange structure 200j and a wrist bearing component 56j. The flange structure 200j is generally identical to the flange structure 200i and as such, will not be discussed in further detail. The wrist bearing component 56j is similar to the wrist bearing component 56i in that it includes a profile 700j that matches the four angled surfaces that make up the proximal side of the flange structure 200j. The wrist bearing component 56j also includes anterior and posterior located portions 600j on the distal sides of the wrist bearing component 56j that extend distally in a manner that overlaps the flange structure 200j. Moreover, the flange 200j, may be any appropriate geometry to substantially complement or match the carpal plate.

Figure 21A:
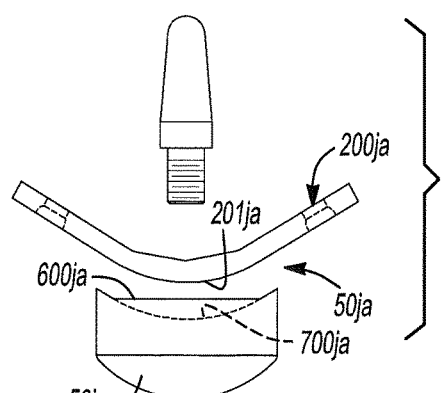
FIG. 21A is an exploded side elevation view of a prosthetic wrist constructed in accordance with the teachings of various embodiments of the present invention.
Figure 22A:
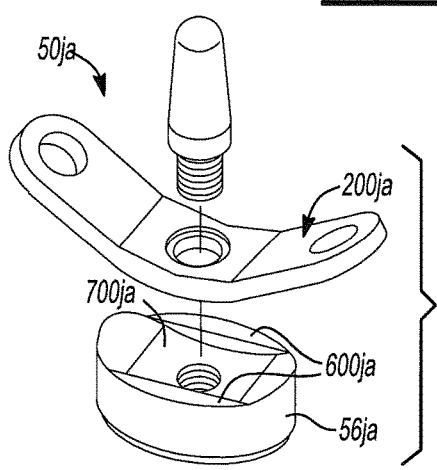
FIG. 22A is an exploded perspective view of the prosthetic wrist of FIG. 21A.

According to various embodiments, illustrated in FIGS. 21A and 22A, wherein the prosthetic wrist 50ja is illustrated to include a flange structure 200ja and a wrist bearing component 56ja. The flange structure 200ja is generally similar to the flange structure 200i and as such, will not be discussed in further detail. Nevertheless, it will be understood that the prosthetic wrist 50ja may include other features and variations. In addition, the flange 200ja may include a proximal surface 201ja that is a substantially smooth arc or radius, as discussed here.

The wrist bearing component 56ja is similar to the wrist bearing component 56i in that it includes a profile 700ja that substantially matches or complements the proximal side 201ja of the flange structure 200ja. The proximal side 201ja of the flange structure 200ja includes a substantially smooth radius or arc. That is the proximal side 201ja may be defined as an arc rather than a plurality of angles. The profile 700ja may include a substantially smooth radius or arc that complements or matches the arc of the flange 200ja. Therefore, the flange 200ja and the bearing component 56ja may substantially mate when assembled.

The wrist bearing component 56ja also includes anterior and posterior located portions 600ja on the distal sides of the wrist bearing component 56ja that extend distally in a manner that overlaps the flange structure 200ja. Moreover, the flange 200ja, including the proximal side 201ja, may be any appropriate geometry to substantially complement or match the surface 700ja of the bearing 56ja.

Figure 23:
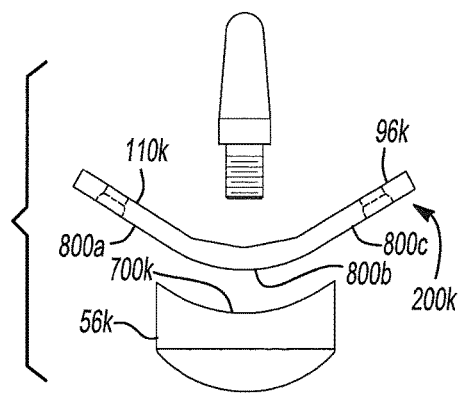
FIG. 23 is an exploded side elevation view of a prosthetic wrist constructed in accordance with the teachings of a twelfth embodiment of the present invention.

A twelfth embodiment is illustrated in FIG. 23 and includes a flange structure 200k and a wrist bearing component 56k. The flange structure 200k includes a distal surface that is configured generally identically to the distal surface of the flange structure 200g. The proximal surface of the flange structure 200k, however, is segregated into a plurality of zones 800a, 800b and 800c. Zones 800a and 800c are generally parallel the ulnar and medial bone abutment surfaces 96k and 110k. Zone 800b, which is coupled at its opposite ends to zones 800a and 800c, is defined by a radius that tangentially intersects zones 800a and 800c. The wrist bearing component 56k includes a profile 700k that matches the proximal surface of the flange structure 200k.

Figure 24:
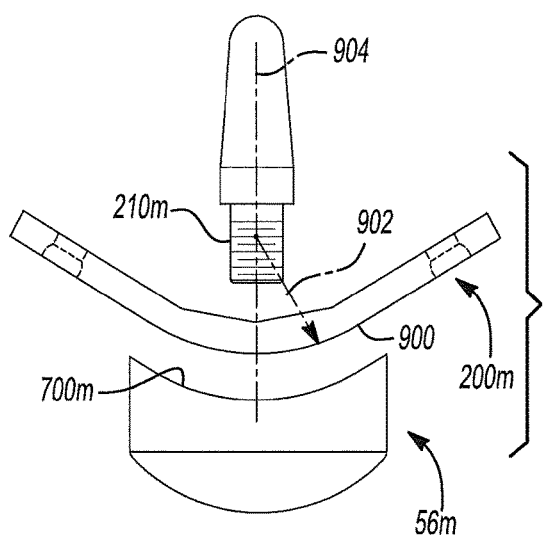
FIG. 24 is an exploded side elevation view of a prosthetic wrist constructed in accordance with the teachings of a thirteenth embodiment of the present invention.
Figure 25:
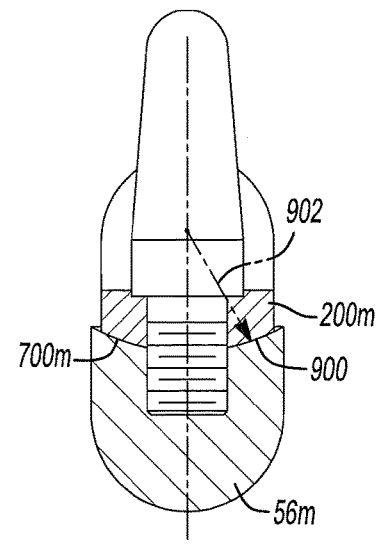
FIG. 25 is a sectional view taken along the line 25-25 of FIG. 24.

In FIGS. 24 and 25, a thirteenth embodiment is illustrated to include a flange structure 200m and a wrist bearing component 56m. The distal side of the flange structure 200m is configured in a manner that is generally identical to the distal side of the flange structure 200k discussed above. The proximal side 900 of the flange structure 200m, however, is defined by a spherical radius 902. In the particular embodiment illustrated, the spherical radius 902 is centered at a point that is disposed along the axis 904 of the connecting portion 210m. Those skilled in the art will appreciate, however, that the center of the spherical radius 902 may be positioned otherwise. The wrist bearing component 56m likewise includes a distal profile 700m that matingly engages the proximal side 900 of the flange structure 200m.

Figure 26:
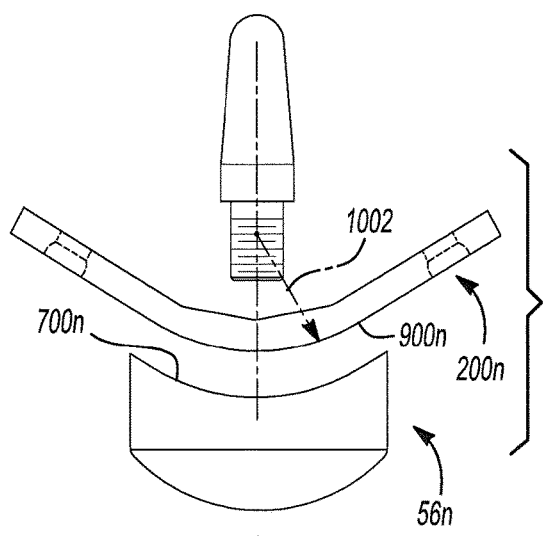
FIG. 26 is an exploded side elevation view of a prosthetic wrist constructed in accordance with the teachings of a fourteenth embodiment of the present invention.
Figure 27:
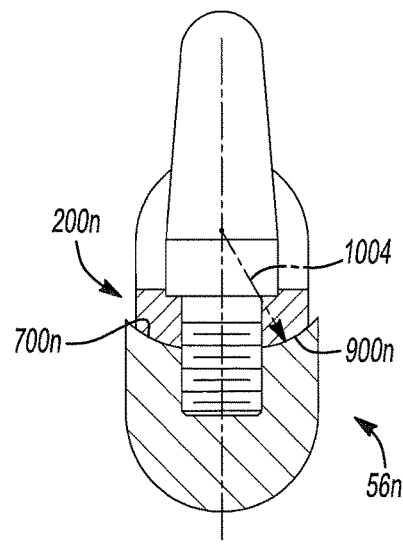
FIG. 27 is a sectional view taken along the line 27-27 of FIG. 26.

In FIGS. 26 and 27, a fourteenth embodiment is illustrated to include a flange structure 200n and a wrist bearing component 56n. The flange structure 200n is generally similar to the flange structure 200m, except that the proximal side 900n is defined by a first radius 1002 in the coronal plane and a second radius 1004 in the sagittal plane. The wrist bearing component 56n is likewise generally similar to the wrist bearing component 56m, except that the distal profile 700*n* of the wrist bearing component is configured with a first radius in the coronal plane and a second radius in the sagittal plane so as to matingly engage the proximal side 900*n* of the flange structure 200*n*.

While some embodiments have been illustrated to include a unitarily formed component, such as a unitarily formed carpal implant, and others have been illustrated to include a component assembly, such as a carpal implant assembly that includes a discretely formed stem and a discretely formed flange structure, those skilled in the art will appreciate that any unitarily formed component may be formed in the alternative utilizing a plurality of discretely formed components and that any embodiment that is shown to be formed using a plurality of discretely formed components may likewise be unitarily formed in the alternative.

Figure 28:
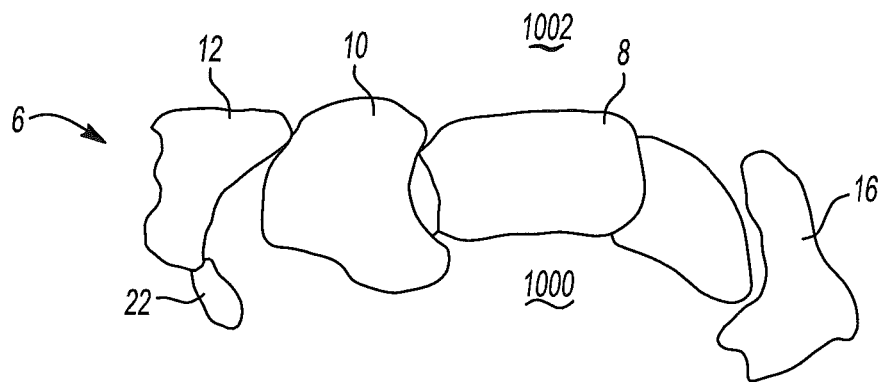
FIG. 28 is a proximal-to-distal view of the carpal complex.

With reference to FIG. 28, the carpal bone complex 6 includes a geometry that also angles or curves about a radius between a volar side 1000 and a dorsal side 1002. The angle is between the volar side 1000 and the dorsal side 1002 of the carpal complex 6. Generally the bones including the hamate 22, the triquetrum 12, the lunate 10, the scaphoid 8, and the trapezium 16 define the dorsal volar curvature or profile of the carpal complex 6. It may be selected to include the radius defined by the carpal complex 6 in a carpal implant. The carpal implant that includes the dorsal volar radius may allow for a substantially easier implantation of the carpal implant and allow for a more natural orientation of the bones of the carpal complex 6 after implantation of the carpal implant. It will be understood that although specific embodiments are illustrated for a carpal implant including the selected radius, that any carpal implant may include the selected radius to allow for a substantially natural implantation of the carpal implant relative to the carpal complex 6.

Figure 29A:
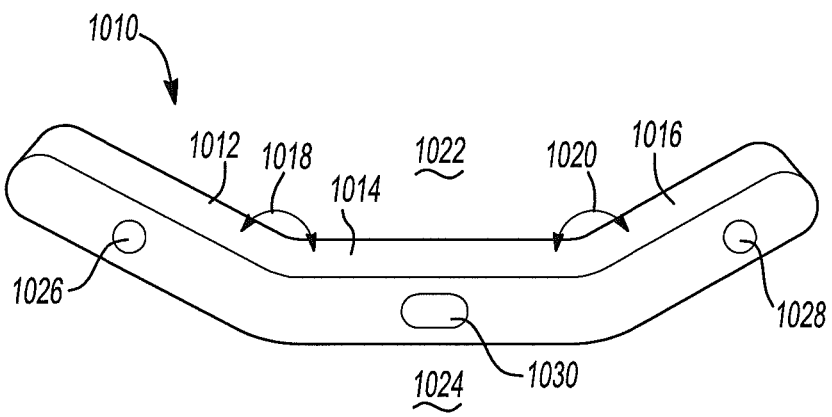
FIG. 29A is a plan view of a carpal implant according to various embodiments.
Figure 29B:
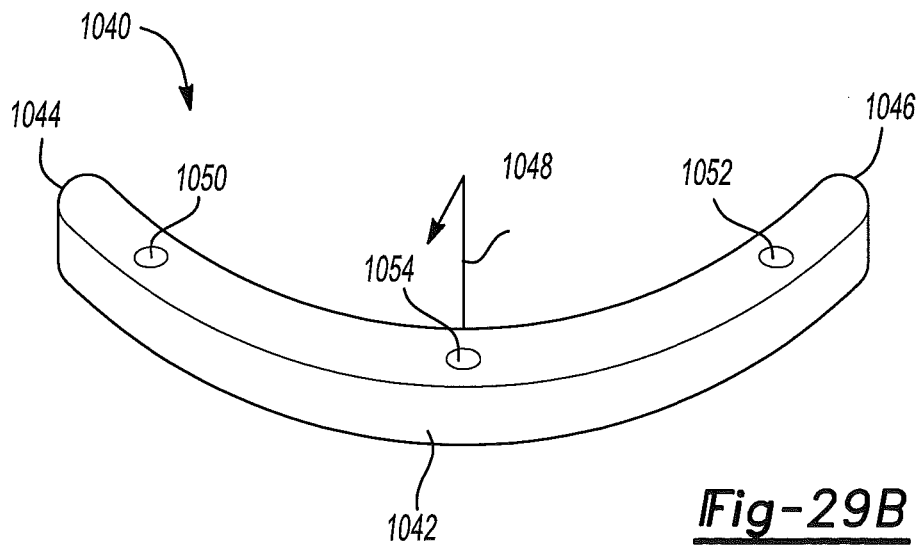
FIG. 29B is a plan view of a carpal implant according to various embodiments.

With reference to FIG. 29, a carpal implant 1010 may be provided that includes a first segment 1012, a second segment 1014, and a third segment 1016. Between the first segment 1012 and the second segment 1014 may be a first angle 1018. Between the second segment 1014 and the third segment 1016 may be a second angle 1020. The first angle 1018 and the second angle 1020 provide a radius about the volar side 1022 of the carpal implant 1010 that includes a radius away from the dorsal side 1024 of the carpal implant 1010. It will be understood that the geometry of the carpal implant 1010 may be included in any appropriate carpal implant, such as various embodiments discussed above and herein. Nevertheless, it will be understood that the geometry of the carpal implant 1010 is not limited to a particular embodiment but may be provided in the various embodiments.

The carpal implant 1010 may include various bores such as a first screw bore 1026 and a second screw bore 1028. In addition, a third bore 1030 may be provided for positioning the stem 80 (FIG. 3) that is to pass through the carpal implant 1010. Regardless, it will be understood that the carpal implant 1010 may be provided with a plurality of portions or included with any of the implants as described above, or herein, so that the first angle 1018 and the second angle 1020 are operable to provide the substantially natural volar radius or dorsal bow for a prosthesis.

With regard to FIG. 29, a carpal implant 1040 may include a member 1042 that extends between a first end 1044 and a second end 1046. The member 1042 may define a radius 1048. The radius 1048 may provide that the member 1042 includes a substantially constant radius or arch between the first end 1044 and the second end 1046. The arch or angle between the first end 1044 and the second end 1046 may be substantially similar to the arch or angle defined by the carpal implant 1010 except that the angle or arch of the carpal implant 1040 is substantially continuous.

The carpal implant 1040 may also include a plurality of portions. For example, the carpal implant may include a first screw bore 1050 and a second screw bore 1052. In addition, the carpal implant 1040 may include a post bore 1054 that is operable to receive a post, as described above.

Although the carpal implant 1010 may include a plurality of angles 1018, 1020, and the carpal implant 1040 may include a substantially continuous radius 1048, each may provide an angle or a bow that is substantially similar to the carpal complex 6. Therefore, the carpal implant 1010, 1040 may be implanted into an anatomy in a substantially natural manner. It will be understood, in addition, that the portions defining the selected bow or radius may be included in any appropriate carpal implant. For example, the carpal implant 54 may include the selected portions and angles that are substantially angled distally to allow for a formation about the carpal complex 6. The carpal implant 54 may also include the dorsal bow that may be defined by the angles 1018, 1020 or the radius 1048. Therefore, it will be understood that the carpal implant may include a plurality of features to allow it to be implanted into a selected anatomy.

In addition, it will be understood that the carpal implant may be substantially intraoperatively bowed to achieve a selected angle or radius. Therefore, during a procedure, a user, such as a surgeon, may determine that a selected bow or radius is required and forms the implant to the selected radius. This may be done by cold working, hot working, bending or any appropriate manner to form the selected bow or angles. Alternatively, or in addition, the carpal implant may be substantially customized for a selected individual. Therefore, pre- or intraoperative measures may be taken of the patient's anatomy, including the dorsal or volar bow of the carpal complex 6 to allow for a formation of the selected carpal implant to substantially mimic that of the natural anatomy of the patient. This may allow for a more natural implantation of the carpal implant into the anatomy of the patient for a substantially more precise anatomical implantation.

Figure 30:
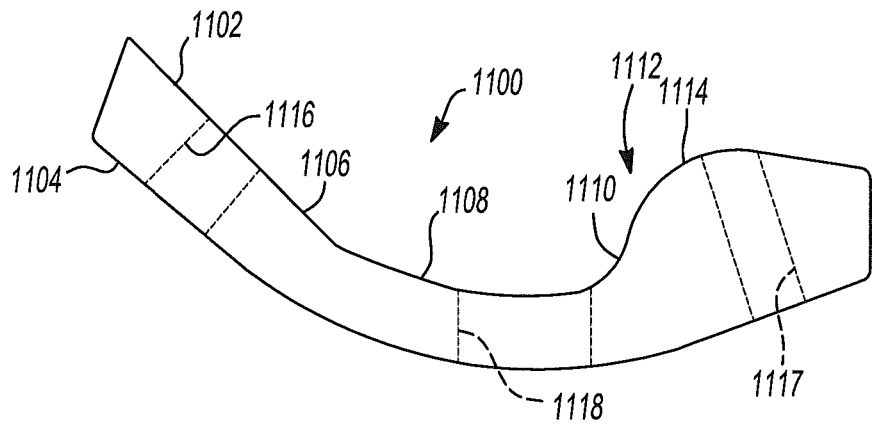
FIG. 30 is a plan view of a carpal implant according to various embodiments.

With reference to FIG. 30, a carpal implant 1100 is provided. The carpal implant 1100 may include a carpal complex engaging side 1102 and a proximal side 1104. The carpal implant 1100 may include the carpal side 1102 that is generally similar to the above-described carpal implants. For example, the carpal engaging side 1102 may include a first or ulnar section 1106, a second section 1108, a third section 1110 (wherein the second section 1108 and the third section 1110 may define a body), and a fourth, ulnar, or augmented section 1112. The augmented section 1112 may differ from those described above and may be provided to replace a selected bone portion, such as the scaphoid 8 in the carpal complex 6. The augmented section 1112 may include an augmented or exterior surface 1114 that may substantially replace the articulating surface of the scaphoid 8 during a procedure. Moreover, the augmented portion 1112 may be substantially integral or modular. Therefore, the carpal implant 1100 may include a member operable to receive a selected augmented region 1112 for selection by a user.

The carpal implant 1100 may further include a screw fixation bore 1116 and a post bore 1118. The screw which may be used to pass through the screw bore 1116 and the post 80 (FIG. 3) may be similar to those described above. In addition a screw fixation bore 1117 may be formed in the augmented section 1112. This may allow a fixation screw, such as those discussed above, to be passed through the augmented section 1112 to engage a portion of the carpal complex 6. This may allow fixing of the carpal implant 1100 to the carpal complex 6 in an appropriate manner. In this way it may also be understood that the surface 1114 does not particularly articulate with a portion of the carpal complex 6 yet the augmented section 1112 is operable to fill a void in the carpal complex 6, such as due to the removal of a selected bone from the carpal complex 6. Nevertheless, the augmented section 1112 may be provided to replace a selected boney portion and the remaining boney portions of the carpal complex 6 may articulate therewith, as discussed herein. Although it will be understood that the carpal implant 1110 may be connected to the carpal complex 6 in any appropriate manner, as mentioned above such that that surface 1114 does not articulate with the carpal complex 6.

The proximal surface 1104 of the carpal implant 1100 may include a substantially continuous convex radius such that it may articulate with a radial implant or a portion of the radius. Alternatively, the carpal implant 1100 may be fixed to a bearing member, such as the bearing member 56, to articulate with the radial implant. The carpal implant 1110 may allow for articulation of various portions of the carpal complex 6 with the other portions of the complex 6 and the radius 2 to allow for substantial replacement of the natural articulation of the wrist.

Figure 31:
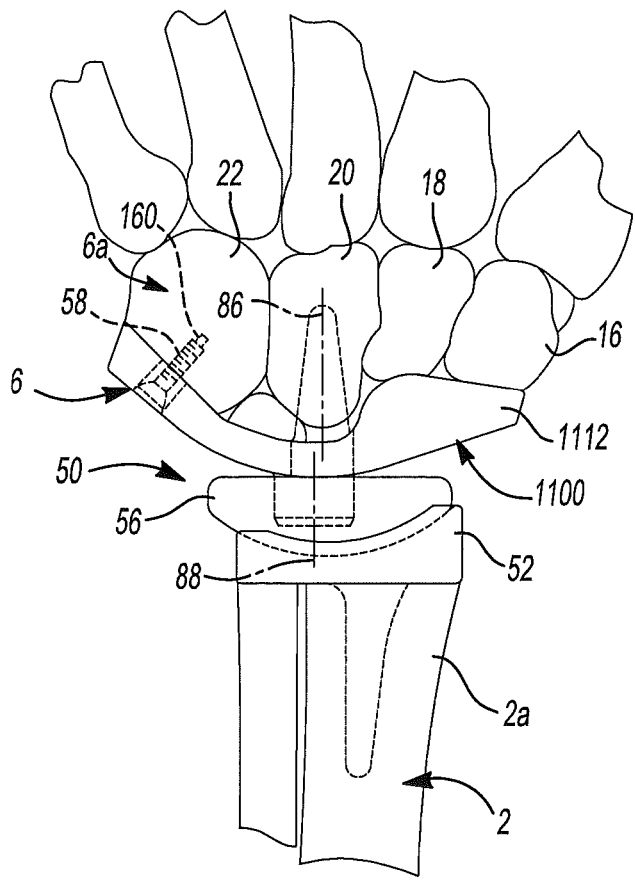
FIG. 31 is an environmental view of the carpal implant according to various embodiments of FIG. 30 implanted.

With reference to FIG. 31, the carpal implant 1100 may be positioned in the carpal complex 6 such that the augmented region 1112 replaces the scaphoid bone 8. Therefore, the augmented region 1112 may be able to articulate with the trapezium bone 16 and the trapezoid bone 18. The augment region may also articulate with the capitate bone 20 as will be understood by one skilled in the art. Therefore, a screw, such as the screw 58, may be used to engage the hamate bone 22 and the carpal implant 1110 is allowed to articulate freely with the other boney portions of the complex 6. Nevertheless, the augmented region 1112 need not articulate with the carpal complex 6.

The resection of the carpal complex 6 may be similar to a resection otherwise required to implant a carpal implant except that the scaphoid 8 may be replaced with the augmented region 1112. The articulating surface 1114 may be defined in such a way that the augmented region 1112 is operable to articulate with the selected bony portions to substantially mimic the natural articulation in the wrist. This may be selected if the scaphoid bone 8 is substantially removed due to a resection procedure, an injury, or the like. Therefore, it is not necessary to fix the carpal implant 1110 to a bone portion through the augmented region 1112, but the other bone portions of the carpal complex 6 may simply articulate with the augment region 1112. It will be understood, however, that the carpal implant 1110 can be fixed to any selected portion of the carpal complex 6.

It will be understood that the carpal implant 1110 may include any appropriate augments to engage any selected portions of the carpal complex 6. Therefore, the augmented region 1112 may be provided to replace the scaphoid bone 8 or other articulating the selected portions of the scaphoid complex 6. Thus, any appropriate augmented region of the carpal implant 1110 may be provided.

In addition, other various embodiments may include various portions that provide for replacement of selected bone segments such as the augmented region 1112. Thus, the carpal implant 1110, according to various embodiments or in conjunction with various embodiments, may be provided to replace a selected or bony portion to allow for a substantially natural articulation within the carpal complex regardless of the condition of the carpal complex. The augmented region 1112 may also be provided to replace other boney portions, such as the lunate 10. Moreover, the carpal implant 1110, as mentioned above, may be substantially modular such that the augmented region 1112 may or may not be included. Moreover, the augmented region may be selected to replace a selected bone by selecting a particular module.

In addition, the post 86 may be provided in the carpal implant 1100 to engage the bone portion capitate bone 20 and also engage the selected bearing member 56. Nevertheless, as discussed above, the radius side 1104 of the carpal implant 1100 may substantially provide an articulating or bearing surface to articulate or bear with the radius 2 or the radial implant 52, or any appropriate radial implant. Nevertheless, the carpal implant 1110 may articulate both with the radial portion, such as the radius 2, the radial implant 52, or any appropriate radial implant, and may also articulate with selected portions of the carpal complex 6. Therefore, the carpal implant 1100 may include both the radial side articulating surface 1104 and the articulating surface 1114 substantially defined by the augmented region 1112. Regardless, the carpal implant 1100 may be provided to allow for replacement of selected bony portions, such as those bony portions that are substantially incapable of providing anatomical support or articulation, by use of the augmented region 1112. Again, such as discussed above, the region 1112 need not articulate with the carpal complex 6 but may fill a mass in the carpal complex 6.

With reference to FIG. 32, a distal radial implant 1200 is illustrated according to various embodiments. The distal radial implant 1200 may be provided as a substantially modular implant that includes a stem portion 1202 that is operable to be positioned relative to a selected portion of the radius 2, such as intramedullary. Affixed or interconnected with a selected portion of the stem portion 1202 is a distal radial segment 1204. The distal radial segment 1204 may be provided to engage the stem 1202 to provide a selected orientation, configuration, size and other considerations for the distal radial implant 1200. Furthermore, a distal radial bearing 1206 may be provided that may engage a selected portion of the distal radial segment 1204. As discussed herein, the bearing 1206 may be fixed to the distal radial segment 1204, may articulate with the distal radial segment 1204, or may be provided in any appropriate configuration. In addition, the bearing 1206 may be omitted, as a bearing extending from the carpal implant may articulate with the distal radial segment 1204. Alternatively, the bearing member 1206 may be omitted, as a carpal implant or portions of the carpal complex 6 may articulate directly with the distal radial portion 1204. Nevertheless, the modular distal radial implant 1202 may be provided in a manner allowing a user, such as a physician, to select a distal radial implant intraoperatively to substantially match the anatomy of a patient.

With reference to FIG. 33, the stem 1202 includes a body portion 1208 and a neck or engaging portion 1210. The neck portion 1210 may include a connection area, such as a male connection post, to engage a respective female connecting area, discussed herein, in the distal radial segment 1204. For example, the stem connection 1210 may include a groove or detent 1212 that is operable to engage a deflectable member or portion of the distal radial segment 1204. Nevertheless, the connection member 1210 may be provided to allow for an interconnection of the stem 1202 with the distal radial component 1204.

The body portion 1208 of the stem 1202 may include a selected geometry. For example, the body portion 1208 may be substantially cylindrical or tapered/conical to allow for easy insertion of the stem 1202 into the radius 2. The body 1208, however, may include a selected geometry to substantially resist rotation of the distal radial implant 1200 after implantation. For example, various extensions or keys, such as fins or tabs 1214, may be provided that extend from an exterior of the body 1208 such that the fins 1214 may engage a selected portion of the bone. In addition, the body 1208 may include a selected irregular geometry or regular geometry that includes portions that may resist rotation. For example, the body 1208 may include a substantially square or rectangular cross-section, may define a substantially "I-beam" cross-section, an oval cross-section, a star cross-section, a cruciform cross-section, or any appropriate cross-section. Nevertheless, the body portion 1208 may be provided for allowing both substantially easy implantation of the modular distal radial implant 1200 and a mechanism to resist rotation of the distal radial implant 1200 after implantation thereof.

Figure 44:
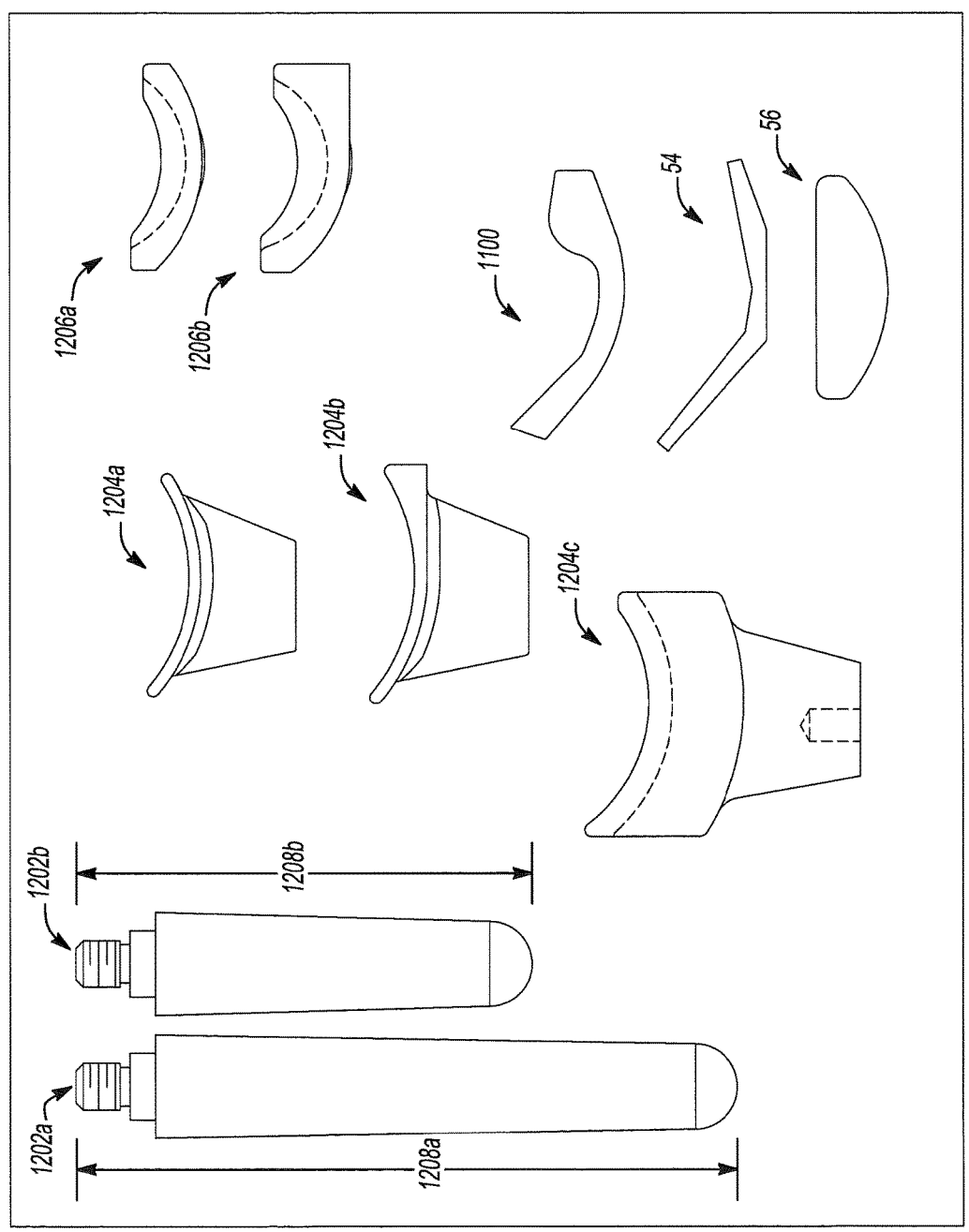
FIG. 44 is a kit view of various embodiments of the present invention.

Furthermore, the stem 1202 may be provided in a plurality of dimensions, such as a diameter, length, curve radius, cross-section, and combinations thereof. For example, the stem portion 1202 may include a diameter or a cross-sectional size 1216, a length 1218, or any other selected dimensions that may be varied. Therefore, a kit 1600 (FIG. 44), or other appropriate selection may be provided such that one or more of the stems 1202 may be provided with one or more variations in the selected dimensions 1216, 1218. For example, in the kit 1600, a plurality of the stems 1202 may be provided where each of the stems 1202 include a slightly different length 1218 such as about 4 cm, about 6 cm, and about 8 cm. Therefore, during a procedure, such as an implantation of the distal radial implant 1200, a user, such as a physician, may select the appropriate length for the stem 1202.

Figure 34A:
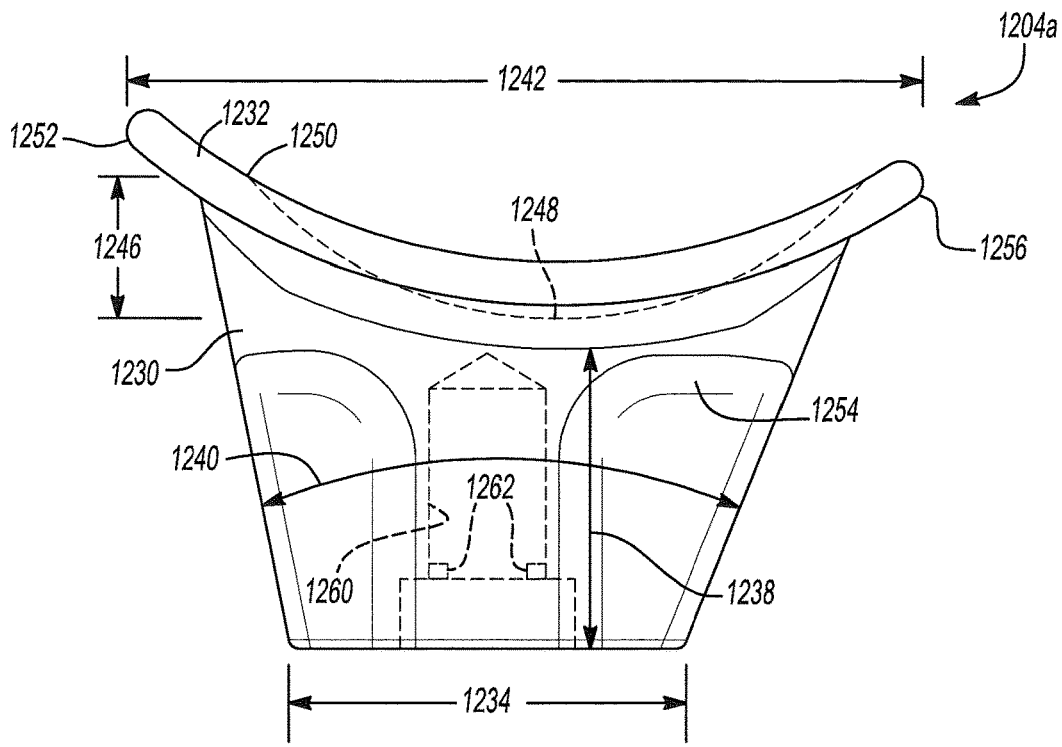
FIG. 34A is a plan view of a distal radial segment of a modular distal radial implant according to various embodiments.
Figure 34B:
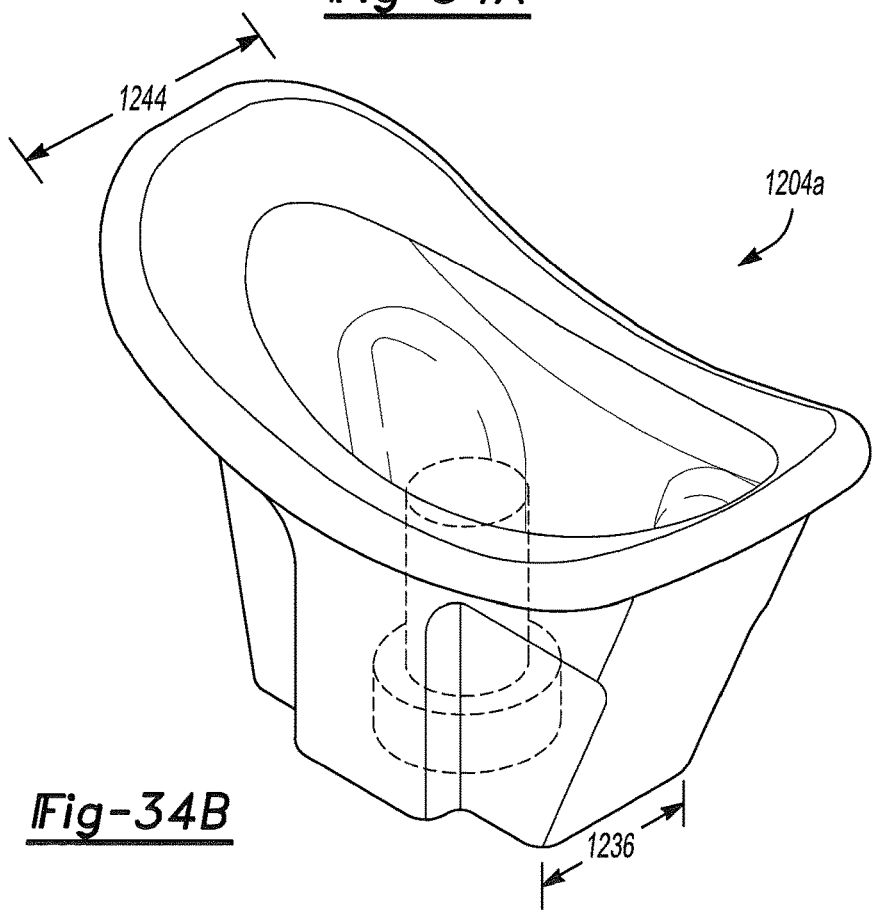
FIG. 34B is a perspective view of the distal radial segment of FIG. 34A.

With reference to FIGS. 34A and 34B, the distal radial segment 1204, according to various embodiments, is illustrated as the distal radial segment 1204*a*. The distal radial segment 1204*a* may include portions that are operable to engage the stem 1202. Nevertheless, the distal radial portion 1204*a* may be formed according to various embodiments, including various embodiments exemplary illustrated herein, or combinations thereof.

The distal radial component 1204*a* generally includes a body portion 1230 and a superior or articulating portion 1232. The body portion may be formed in any appropriate manner to engage a selected portion of the anatomy. The body 1230 may include selected dimensions such as a length 1234, a width 1236, a height 1238, and an arch or radius 1240. The various dimensions 1234, 1236, 1238, and 1240 may be varied for various applications. As discussed above, and in conjunction with the stem 1202, a plurality of the distal radial segments 1204*a* each including a unique set of dimensions 1234-1240 may be provided. Each may be provided in a large inventory or in the kit 1600 (FIG. 44) for selection by a user substantially intraoperatively or preoperatively. Nevertheless, various sizes or configurations of the distal radial implants 1204*a* may be provided to allow for a substantially customized fit with a selected patient.

The distal radial component may also include the articulating region or portion 1232 that may also include a plurality of selected dimensions. For example, the articulating region 1232 may include a length 1242 and a width 1244. The articulating region 1232 may also include an articulation depth 1246 that may vary depending upon a selected application. The articulation depth 1246 may generally be understood to be the deepest portion of the concave region 1248 that defines the articulating surface of the articulating region 1232. The uppermost portion of the height 1246 may be a point where the articulating surface stops or transforms into a lip 1252. Therefore, the upper portion 1250 of the articulating surface may extend to the edge of the articulating region 1232 or may stop intermediate thereof. Again the articulating region 1232 including the various dimensions 1242-1246 may be varied and unique for a plurality of the implants 1204*a*. Therefore, again, the user may select the distal radial implant 1204*a* according to selected requirements or dimensions of a patient.

The distal radial implant 1204*a* may define a selected geometry of the body 1230. For example, the body may include a single or plurality of depressions 1254 for various reasons. For example, the depressions 1254 may assist in allowing for a fixation of the distal radial implant 1204*a* to a selected portion of the anatomy. In addition, the body 1230 may be substantially smooth over the surface thereof or include other various selected geometries. Again a plurality of geometries may be selected for various uses during an implantation.

The articulating region 1232 may include the first lip 1252 and a second lip 1256. The lips 1252, 1256 may extend a distance beyond an edge of the body 1230. The lips 1252, 1256 may be dimensioned depending upon a selected portion of the anatomy or a selected patient.

Defined in the body 1230 is a female receiving or interconnection portion or depression 1260. The female interconnection 1260 may include a dimension that allows for substantial interconnection with the male interconnection 1210 of the stem 1202. The reception or interconnection portion 1260 may include a deformable member (such as a canted coil spring or screw or other mechanism) 1262, or screw which may engage the depression 1212 of the stem 1202. Therefore, the distal radial component 1204*a* may be interconnected with the stem 1202 for an implantation. It will be understood, that the body 1230 may define a male connection and the stem define a female connection. Thus the interconnection may be performed in any appropriate manner and these are merely exemplary.

Figure 35A:
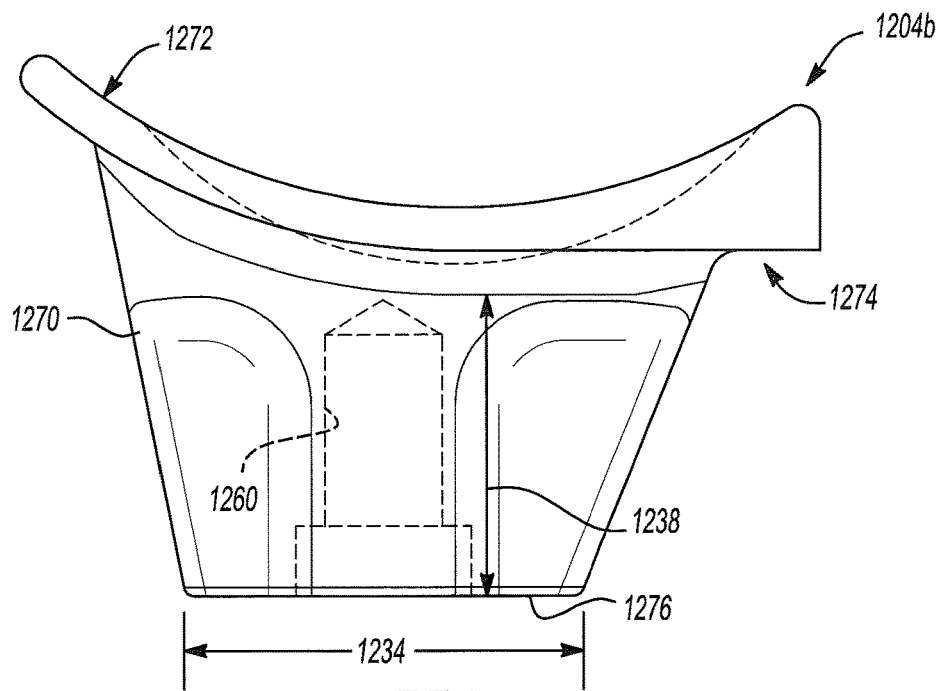
FIG. 35A is a plan view of distal radial segment for a distal radial implant according to various embodiments.
Figure 35B:
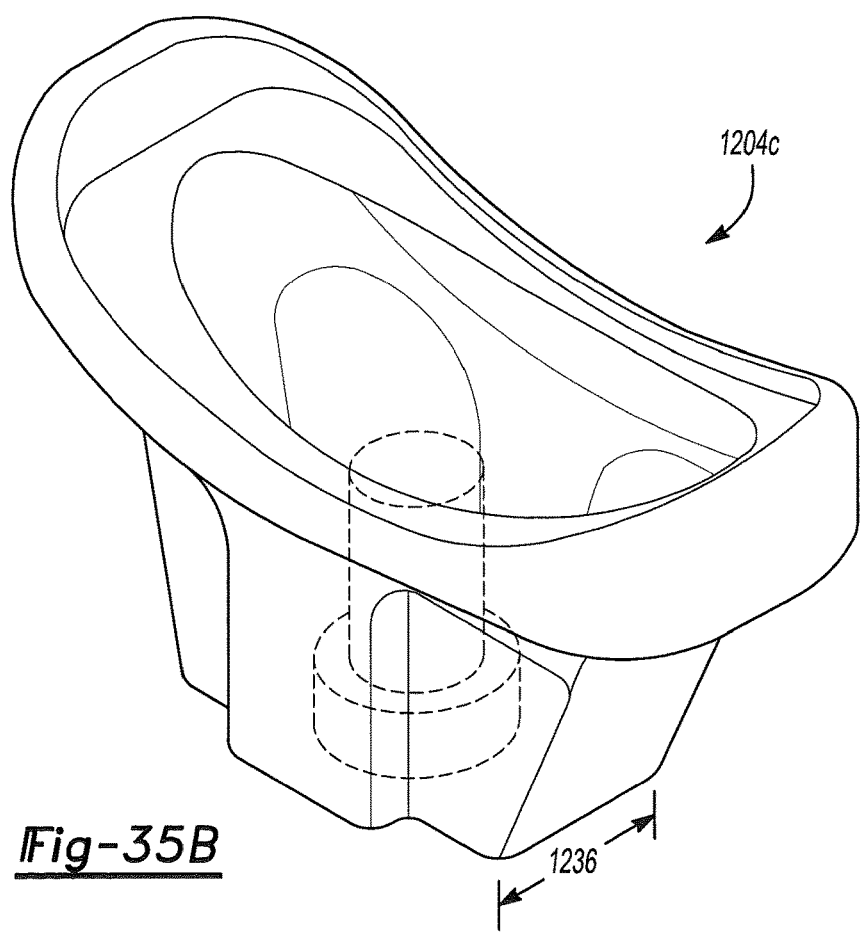
FIG. 35B is a perspective view of the distal radial segment of FIG. 35A.

With reference to FIGS. 35A and 35B, a distal radial implant 1204 according to various embodiments of a distal radial implant 1204*b* is illustrated. The distal radial implant 1204*b* includes portions similar to the distal radial implant 1204*a* and like numerals will be used to indicate like portions. The distal radial implant 1204*b* includes a body portion 1270 and an articulation portion 1272. The body 1270 may be substantially similar to the body 1230 of the distal radial implant 1204*a*. Nevertheless, the articulation region 1272 may include a projection or flat spot 1274. The flat spot 1274 may be viewed as a portion of the body 1270 but extends a distance substantially parallel to a base 1276 of the body 1270. The flat portion 1274 may substantially abut a distal portion of the radius 2 during and after implantation. Therefore, the flat portion 1274 may allow for a substantially stable interconnection with the radius 2 after the implantation. Alternatively, the flat portion 1274 may be provided for a further connection or fixation portion to engage the radius 2.

Nevertheless, the distal radial implant 1204*b* may include the plurality of dimensions 1234, 1236, 1238, 1240, 1242, 1244, and 1246. As discussed above, the plurality of dimensions may be substantially unique and different among a plurality of the distal radial implants 1204*b* for a modular interconnection and selection by a user. In addition, the flat portion 1274 may be provided on the distal radial implant 1204*b* as one of a plurality of the distal radial implants 1204 that may be provided in an inventory or the kit 1600 for use by a user. Therefore, the distal radial implant 1204*b* may be provided for forming a distal radial implant 1200 depending upon a selected patient.

Figure 36A:
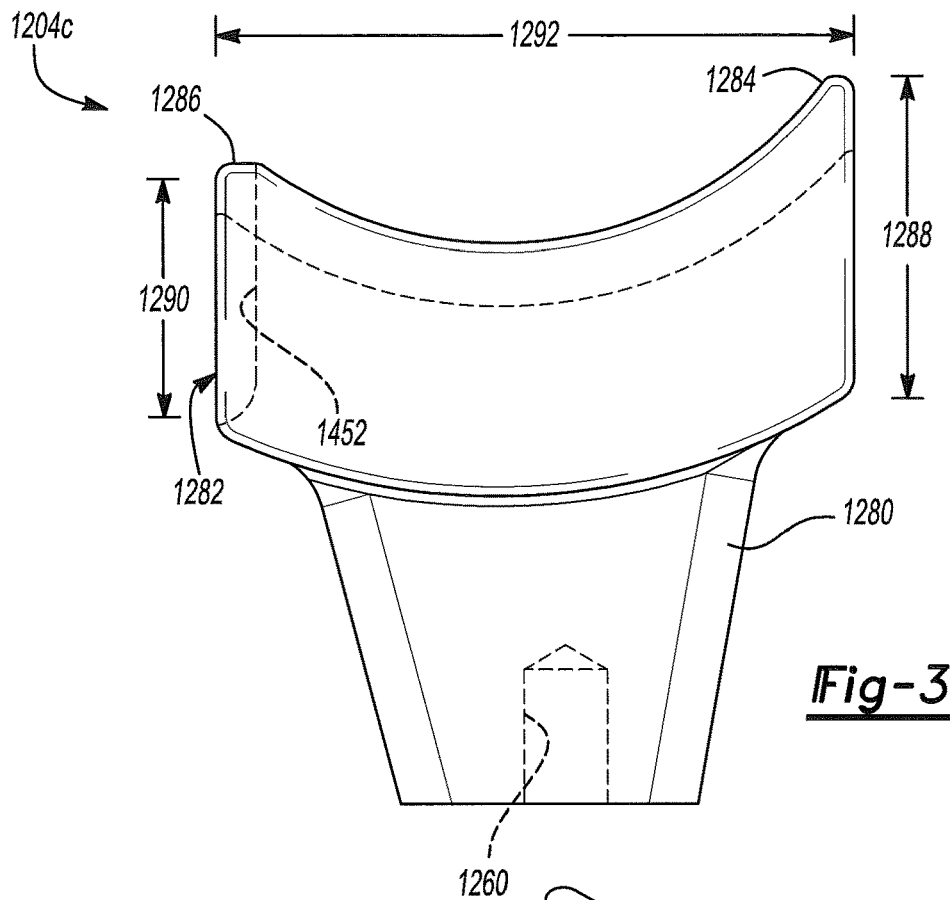
FIG. 36A is a plan view of a distal radial segment implant according to various embodiments.
Figure 36B:
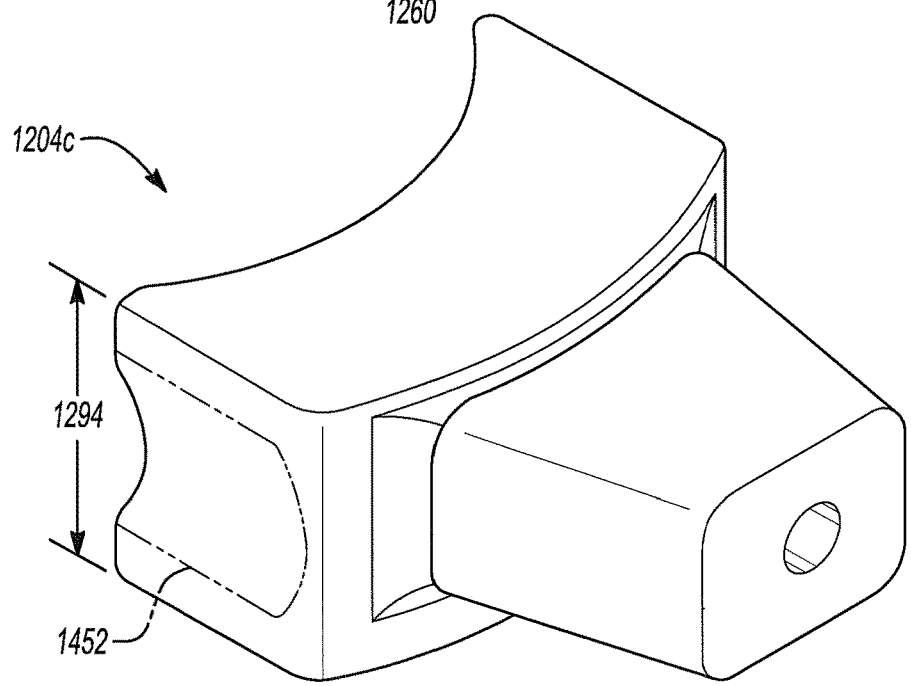
FIG. 36B is a perspective view of the distal radial implant of FIG. 36A.

With reference to FIGS. 36A and 36B, a distal radial implant 1204 according to various embodiments of a distal radial implant 1204*c* is illustrated. The distal radial implant 1204*c* may include portions that are similar to the portions of the distal radial implant 1204*a* and like numerals are used to reference like portions of the distal radial implant 1204*c*. In addition, it will be understood that the distal radial implant 1204*c* may include portions that are selectable to be used with other various embodiments of the distal radial implant 1204*a* and the distal radial implant 1204*c* is merely exemplary.

The distal radial segment 1204*c* includes a body 1280 that may be similar to the body 1230 of the distal radial implant 1204*a*. Therefore, the body 1280 may also include the female engaging portion 1260 operable to engage a selected portion of the stem 1202. Nevertheless, as discussed above, the female engaging portion 1260 may be any appropriate size, configuration and the like. In addition, any appropriate portion may be provided to engage the stem 1202. In addition, the body 1280 may include selected portions, such as depressions, dimensions and the like that may be substantially different for a selected use or patient.

Extending distally from the body 1280 is the carpal engaging region or portion 1282. The carpal engaging region 1282 can extend from the body 1280 to engage a selected portion of the carpal complex 6. The bones of the carpal complex 6 may be held within the carpal engaging portion 1282 so that the bones of the carpal complex 6 are operable to articulate in a generally natural manner but may be held relative to one another to allow for a fixation of the wrist relative to the distal portion of the radius. Essentially the holding portion 1282 may surround a selected number or volume of the carpal complex 6 to allow for retention of the natural boney portion after implantation of the distal radial segment 1204*c*.

The distal radial segment 1204*c* may be provided for a substantially hemi-arthroplasty where substantially only the distal portion of the radius 2 is replaced. The distal radial segment 1204*c* may articulate with the carpal complex 6 to reduce the need for a carpal implant. Further, distal radial segment 1204*c* can include an ulna articulation portion 1452, as discussed further herein. This articulation section can allow for a selected articulation of the ulna 4 with the distal radial segment 1204*c*.

Figure 37:
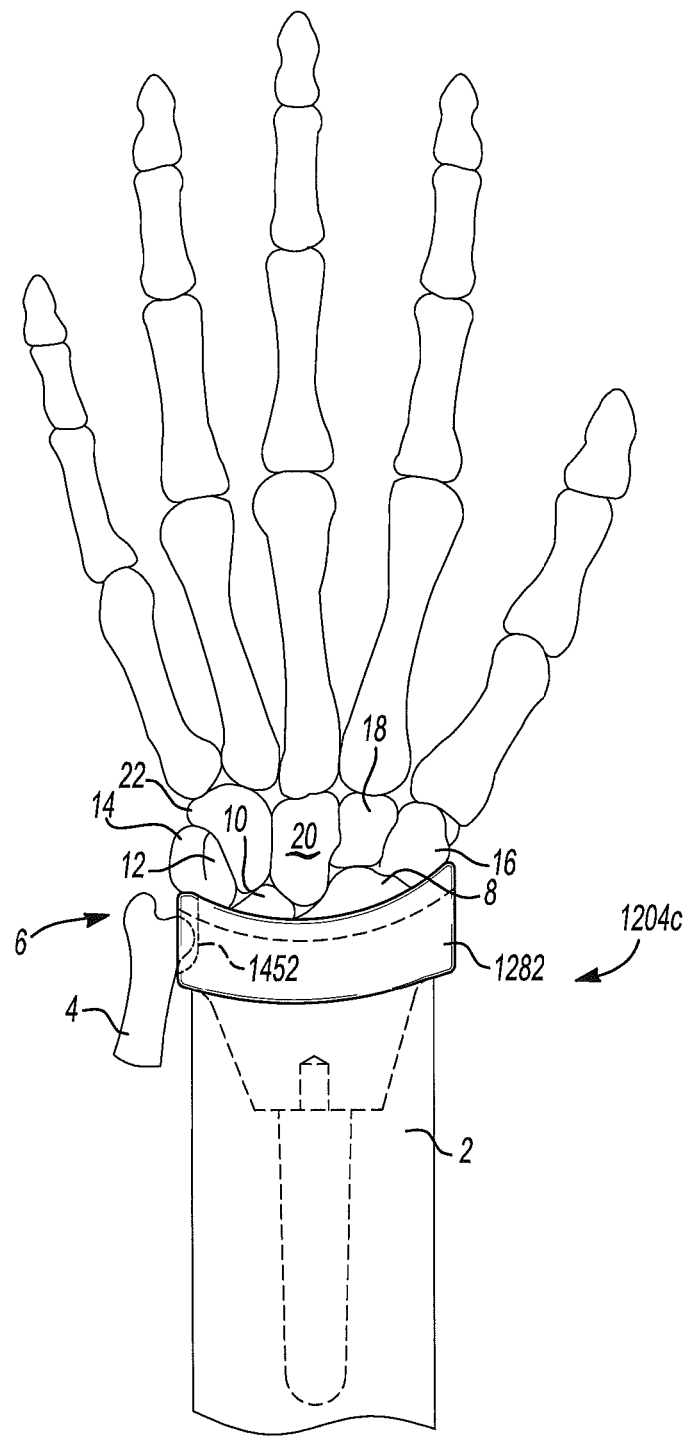
FIG. 37 is an environmental view of the distal radial implant of FIG. 36A in an implanted position.

With reference to FIG. 37, the distal radial implant segment 1204*c* may be implanted to substantially capture or surround selected portions of the carpal complex 6 such as the scaphoid 8, the lunate 10, the triquetrum 12, and the trapezium 14. Therefore, if any portions of these bones are resected or if the portions of the carpal complex 6 are left substantially whole, they may be enclosed within the carpal complex portion 1282 of the distal radial implant 1204*c* It will be understood that the containing portion 1282 may be shaped and sized for any appropriate application and may include a selected geometry for holding or fixing a selected number of the bones of the carpal complex 6. Moreover, a bearing component may be fit or molded onto the container portion 1282 to allow for a substantially smooth articulation of the various bones of the carpal complex 6 relative to the distal radial implant segment 1204*c*. The ulna 4 can be positioned relative to the implant member 1282 at any appropriate position and me be near the surface or deeper based upon various characteristics.

Returning reference to FIGS. 36A and 36B, the distal radial implant segment 1204*c* includes the carpal engaging section 1282, which may include a plurality of selected dimensions. For example, the carpal containing section 1282 may include a selected high or ulnar side 1284 and a radial side 1286. This may allow for the carpal engaging section 1282 to substantially mimic the natural shape of the distal radial portion and how it would engage the carpal complex 6. For example, the distal radial implant 1204*c* may engage and hold the carpal complex bone 6 in a selected orientation and shape. Therefore, the high side 1284 may include high side height 1288 and a low side 1286 may include a low side height 1290. Furthermore, the carpal containing section 1282 may include a length 1292 and a width 1294. Therefore, the carpal containing section 1282 may include a plurality of dimensions 1288-1294 that may be selected and varied depending upon a particular patient or user. In addition, as discussed above, a plurality of the radial distal implants 1204*c* may be provided in either an inventory or kit 1600 for selection during a procedure to allow for a substantial customization of the implant for a selected patient.

Nevertheless, the carpal containing selection 1282 may allow for holding a selected number of the carpal bones in the carpal complex 6 in a selected manner for a substantially natural articulation. The carpal containing section 1282 may hold portions of the carpal complex 6 in a manner such as to allow for an articulation of even a weakened or fractured carpal complex. In addition, the carpal containing section 1282 may be used when various portions of the anatomy may be resected, such as removal of the entire proximal row of the carpal complex 6. In addition, the carpal containing section 1282 may retain resected portions of the bone segments that form the proximal row of the carpal complex 6 and may allow for collecting the portions of the carpal complex in such a manner to allow for articulation of the carpal complex 6 relative to the radius 2 by way of the distal radius segment 1204*c*.

Figure 38A:
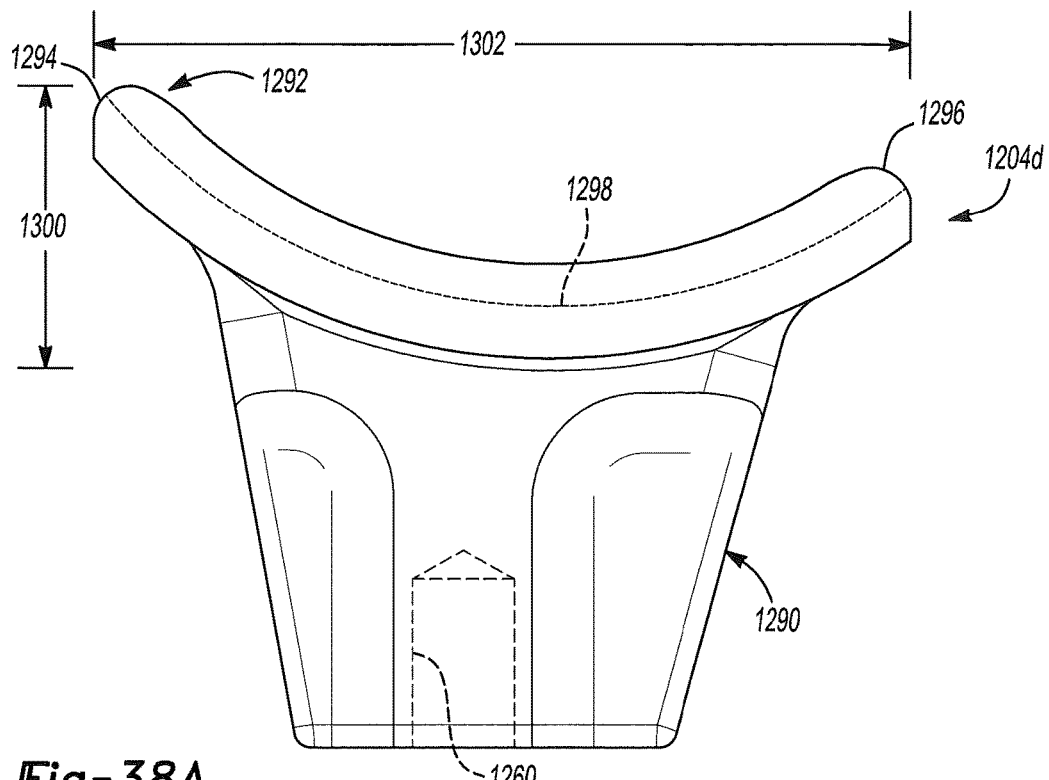
FIG. 38A is a distal radial segment of the distal radial implant according to various embodiments.
Figure 38B:
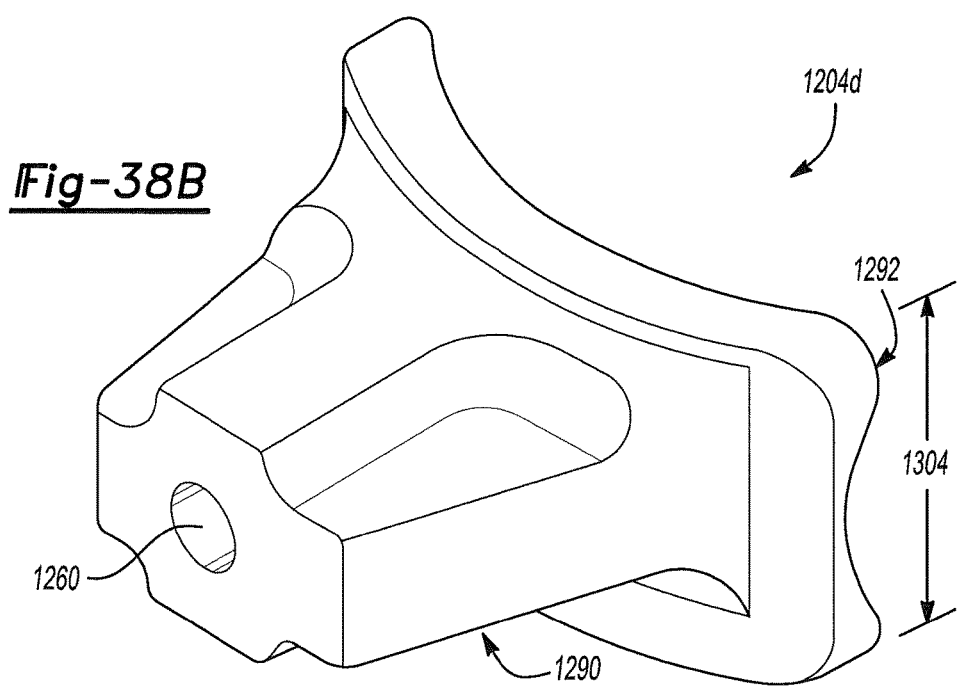
FIG. 38B is a perspective view of the distal radial segment of FIG. 38A.

With reference to FIGS. 38A and 38B, a distal radial implant 1204 according to a various embodiment of a distal radial implant 1204*d* is illustrated. The distal radial implant 1204*d* may include portions similar to the distal radial implant 1204*a* and like numerals are used to indicate like portions.

The distal radial implant 1204*d* may be similar to the distal radial implant 1204*c* in that both may be used for a substantially hemi-arthroplasty of the wrist including a resurfacing or arthroplasty of substantially only the radius bone 2 or the distal radial portion. Therefore, the distal radial segment 1204*d* may include a body 1290 that includes the female engaging portion 1260. The distal radial implant segment 1204*d* may interconnect with the stem 1202 to allow for formation of a selected distal radial implant. In addition, the body portion 1290 may include selected detents and other formations to allow for an implantation of the distal radial implant 1204*d* into a selected anatomy.

Extending from the body portion 1290 is an articulating or carpal portion 1292. The carpal portion 1292 may include a ulnar or first side 1294 and a radial or second side 1296. Extending between the two sides 1294, 1296 is a surface, such as an articulation surface 1298. The articulation surface 1298 may be a substantially metal articulation surface that does not necessarily require a bearing, such as a polymer bearing. The articulating surface 1298 may be used to articulate with a selected portion of the carpal complex in a substantially hemi arthroplasty replacement. Therefore, the articulating surface 1298 may be substantially a metal, or any other appropriate material, including a plastic, ceramic, pyrocarbon (also referred to as pyrolytic carbon) portion such that the body 1290 and the articulating region 1292 may be formed as a substantially single portion.

The articulating region 1292 may be provided in such a manner to articulate with a selected portion of the carpal complex 6 in a way that allows for replacement of only the distal portion of the radius 2 without augmentation of the carpal complex 6. Therefore, particularly in selected situations such as a fracture, chip and the like of the radius 2, the distal radial implant 1204*d* may be used to resurface the selected portion of the radius 2 without requiring a carpal implant.

The articulating region 1292 may include selected dimensions such as a height 1300, a length 1302, and a width 1304 that may be different or selected depending upon a use or patient. For example, a selected size of the carpal complex 6 may require a selected size of the articulating region 1298 to engage the carpal complex 6 in a selected manner. In this way, the articulating portion 1298 may articulate with the carpal complex 6 to allow for replacement of substantially only the distal portion of the radius 2 rather than a replacement of a portion of the carpal complex 6 and a carpal implant.

Although the articulating region 1298 may be a substantially metal or hard material, such as a ceramic or pyrocarbon, articulating region, it will be understood that the articulating region 1298 may also include a bearing. The bearing may include a polymer bearing, such as a bearing formed of a ultra-high molecular weight polyethylene or any other appropriate bearing portion. Alternatively, the bearing surface 1298 may simply be a highly polished surface, which allows for substantially easy, smooth articulation of portions of the carpal complex 6 relative to the distal radial implant segment 1204*d*. It will be understood, therefore, that the various distal radial implants 1204 may be used for a complete or hemi arthroplasty of the radius 2.

Figure 39A:
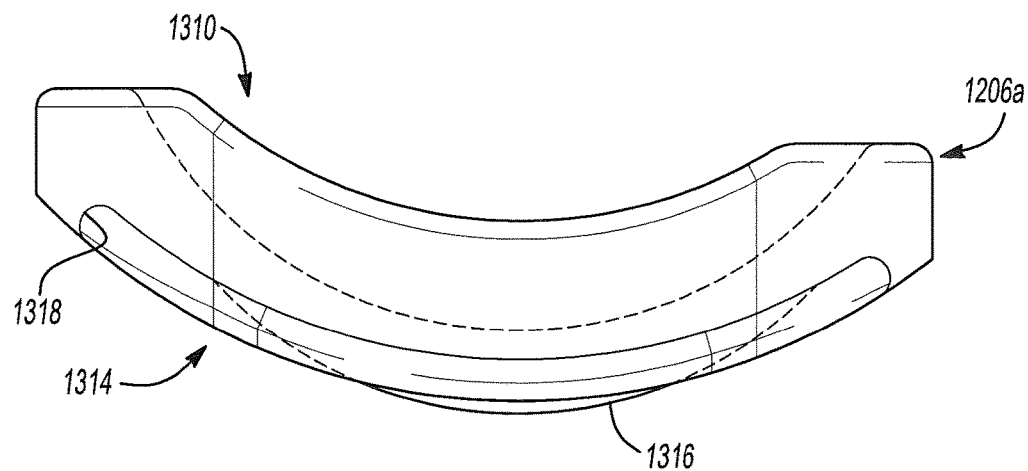
FIG. 39A is a plan view of a bearing portion for a distal radial segment according to various embodiments.
Figure 39B:
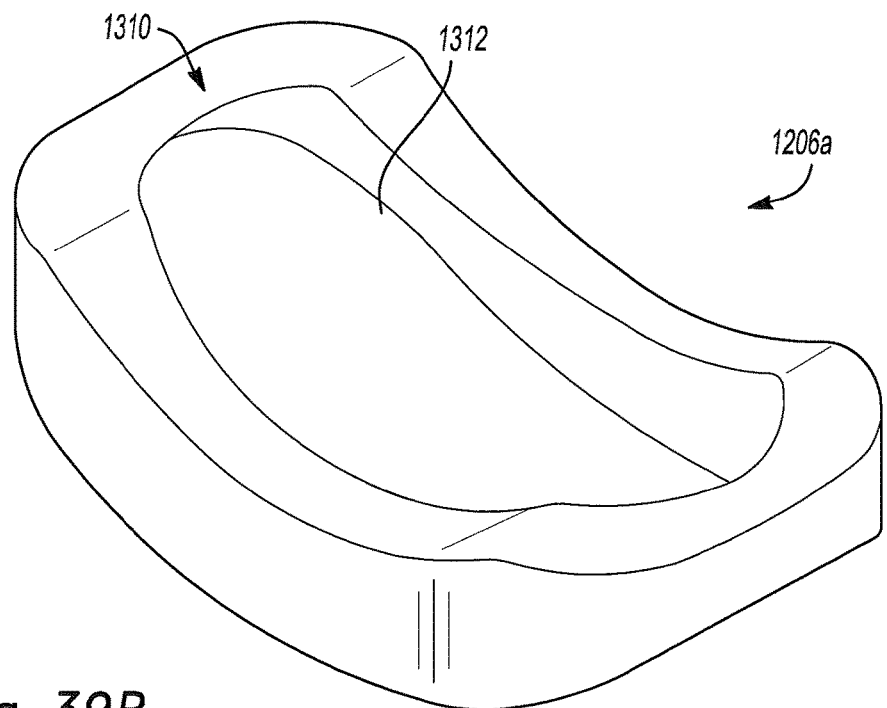
FIG. 39B is a perspective view of the bearing portion of FIG. 39A according to various embodiments.

With reference to FIGS. 39A and 39B, a bearing component 1206 according to selected embodiments of a bearing component 1206*a* is illustrated. The bearing 1206*a* may be interconnected with a selected distal radial implant 1204 according to various embodiments. Therefore, it will be understood that the bearing portion 1206*a* may be affixed to a selected one of the distal radial implants such as the distal radial implant 1204*a*.

The bearing components 1206*a* includes an articulation or carpal bearing side 1310 that defines a bearing surface 1312. The bearing component 1206*a* also defines a distal radial bearing side 1314. The distal radial bearing side 1314 defines a distal radial bearing surface 1316. The distal radial bearing surface 1316 is provided to substantially seat within the bearing side 1232 of the distal radial implant 1204.

The bearing 1206*a* may be substantially fixed to the distal radial component 1204*a* in any appropriate manner. For example, the bearing 1206*a* may be adhesively affixed, mechanical affixed, welded, otherwise bonded, or the like. For example, a selected deformable or engageable lip or edge 1318 may be provided to engage the lip 1252 and, 1256 of the distal radial implant 1204*a*. Alternatively, various locking portions such as screws, bars, and the like may substantially interconnect the bearing components 1206*a* with the distal radial components 1204*a*. Therefore, the bearing components 1206*a* may substantially be held relative to the distal radial component 1204*a* allowing for a substantially stable base of articulation of the carpal complex 6 and portions of the wrist relative to the varying portion 1206*a* and the distal radial implant 1204*a*.

The articulating surface 1312 of the distal radial implant 1206*a* may allow for articulation of selected portions of the distal carpal complex 6. The carpal complex 6 may be allowed to articulate within the articulating surface 1312 to allow for a natural articulation of the wrist relative to the implant 1200.

Alternatively, the articulating surface 1312 may be provided to articulate with a selected portion of the carpal implant according to various embodiments. For example, the carpal bearing member 56 may be provided to articulate within the articulating surface 1312 of the bearing member 1206*a*. Therefore, a total wrist replacement may be provided that includes the carpal implant 54 and the carpal bearing implant 56. The carpal bearing implant 56 may include a substantially polymer or a substantially metallic surface. Nevertheless, it is generally selected to provide a metal on polymer bearing articulation such that the bearing member 1206*a* may be formed of either a polymer or a metal portion.

Alternatively, a carpal implant such as the carpal implant 1100 may be provided. The articulating surface 1104 of the carpal implant 1100 may be allowed to articulate with the articulating surface 1312 of the bearing member 1206*a*. Therefore, the carpal implant 1100 may be implanted relative to the carpal complex 6 and may then articulate with the bearing 1206*a*. Therefore, no additional or separate bearing components may be necessary and the bearing 1206*a* may divide the bearing portion between the carpal implant 1100 and a selected distal radial implant segment 1204.

As discussed above, the distal radial bearing 1206*a* may be substantially molded to the distal radial implant segment 1204 to allow for a fixation of the bearing components relative to the distal radial segment 1204. Thus, the modular component may be provided to allow for a minimal amount of portions that are necessary to be implanted to form a substantially total wrist arthroplasty.

Figure 40A:
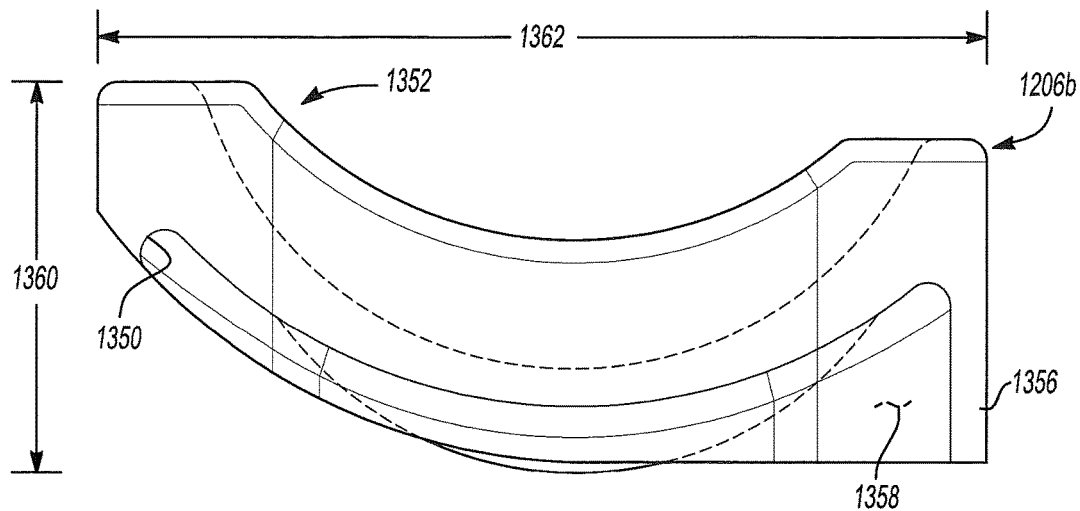
FIG. 40A is a plan view of a bearing portion for a distal radial implant according to various embodiments.
Figure 40B:
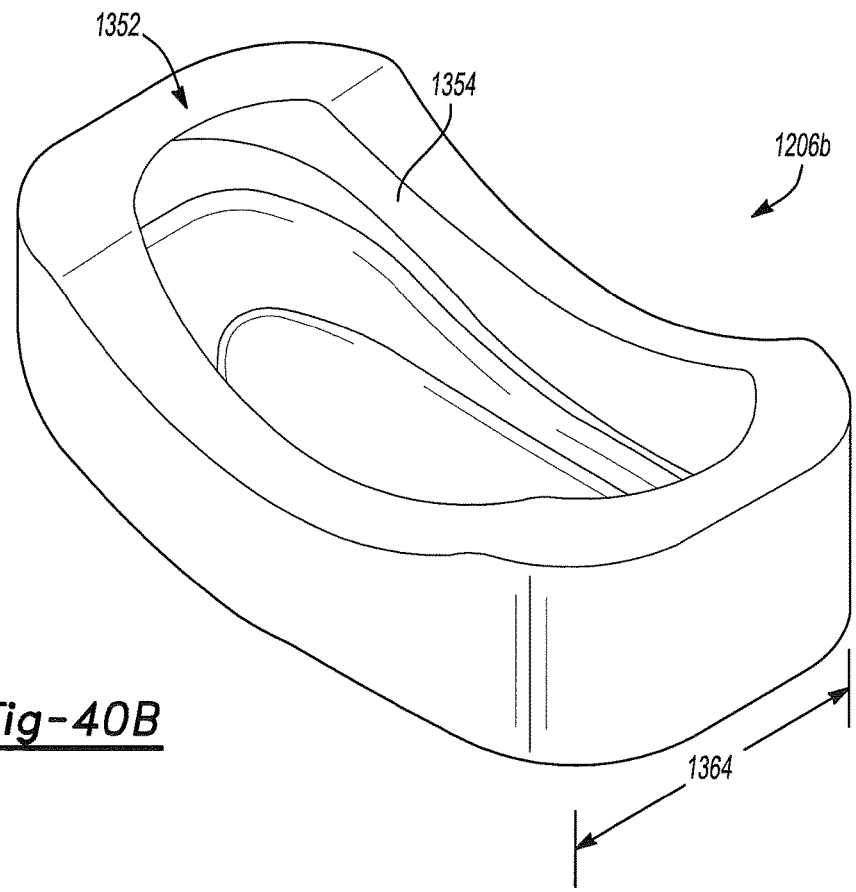
FIG. 40B is a perspective view of the bearing portion of FIG. 40A.

With reference to FIGS. 40A and 40B, a distal radial bearing member 1206*b* which is a distal bearing member according to various embodiments of the distal radial bearing member 1206 is illustrated. The distal radial bearing member 1206*b* may be provided with any of the selected distal radial implant segments 1204. According to various embodiments, the distal radial implant 1206*b* may be interconnected with the distal radial implant 1204*b*.

For example, the distal bearing implants 1206*b* may be substantially molded or adhered to the distal radial implant 1204*b* similar to the fixation of the distal radial bearing portion 1206*a*. Therefore, various fixation mechanisms such as an adhesive, a screw, a locking bar and the like may be provided. For example, a substantial locking tab or projection 1350 may be provided to engage a rim or section 1272 of the distal radial implant 1204*b*. The distal radial bearing member 1206*b* also includes an articulation side 1352 that defines a bearing surface 1354. The bearing surface 1354 may articulate with a selected portion of the carpal complex 6 or a selected portion of a carpal implant.

As discussed above, the articulation surface 1354 may articulate with a bearing portion of a carpal implant 54 or any appropriate bearing portion of a selected various embodiment of a carpal implant. In addition, the articulation surface 1354 may articulate with an articulating surface 1104 of the carpal implant 1100, discussed above. Therefore, either the carpal implant 1100 alone may articulate with the bearing member 1206*b* or a separate bearing portion, which is interconnected with a carpal implant, may articulate with the bearing surface 1354 of the bearing implant 1206*b*.

In addition, the bearing portion 1206*b* includes a flat or flat extending portion 1356 that extends proximally away from the articulating side 1352. The flat portion 1356 may extend around the flat portion 1274 of the distal radial implant 1204*b*. This may allow for providing a portion of the bearing member around a selected portion of the distal radial implant 1204*b* for selected purposes. The extending or flat member 1356 may define a void 1358 which is operable to engage or receive a selected portion of the flat portion 1274 of the distal radial implant 1204*b*.

The bearing portion 1206 according to various embodiments, including the exemplary embodiments, 1206*a* and 1206*b*, may include various dimensions, such as height 1360, a length, 1362 and a width 1364 or a plurality of dimensions. Therefore, the bearing component 1206 according to various embodiments may include a substantial plurality number of unique and selectable dimensions for various applications. Therefore, a user may select one of a plurality of the varying components 1206 to meet selected requirements of a particular patient. The user may select an implant from the kit 1600 (FIG. 44), an inventory or the like to provide an implant for the requirements of a selected patient.

Therefore, it will be understood that the modular distal radial implant 1200 may include a plurality of the stems 1202, a plurality of the distal radial segments 1204, and a plurality of the distal radial bearing components that may be selected and interconnected in various and selected manners. This allows for the distal radial implant 1200 to be provided as a substantially selectable implant for various particular patients and uses by a user, such as physician. The modular assembly may also allow for a substantial intraoperative selection of the implant for a particular patient by a physician or user. Thus, the implantation may proceed while allowing for a substantially intraoperative customization of the implant 1200 to the patient. In addition, the modular implant 1200 may be easily augmented or portions replaced during a revision procedure due to the modular nature of the implant 1200.

Figure 45:
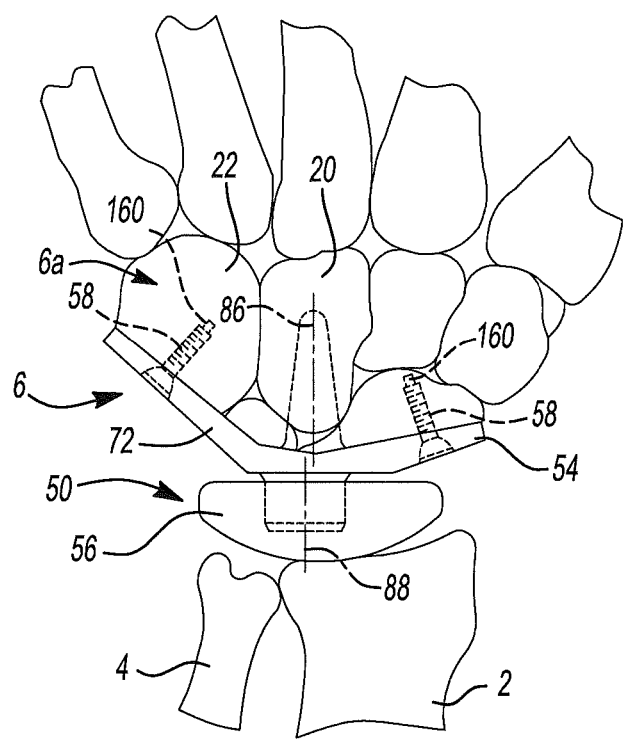
FIG. 45 is an environmental view of a hemi-arthroplasty replacing a portion of a carpal complex according to various embodiments.

As briefly discussed above, it will be understood that various implants may be provided as substantially hemi-arthroplasty or total wrist replacement. For example, the carpal implants, such as the carpal implants 54 or the carpal implant 1100 may be provided to interconnect with selected portions of the carpal complex 6 to substantially articulate with a natural portion of the radius and ulna, as illustrated in FIG. 45. Therefore, a hemi-arthroplasty of the wrist joint or the wrist area may be provided by only resurfacing or providing the carpal implant. As discussed above, the carpal implant may include a size to interconnect with a plurality of the bones of the carpal complex 6 or may also replace a selected portion of the bones of the carpal complex 6. Regardless, the carpal implant may be provided to articulate with a natural portion of the radius.

Likewise, the distal radial implant according to various embodiments may be provided to substantially articulate with a natural portion of the carpal complex, as discussed above and herein. Therefore, the distal radial implant may be provided to articulate with a selected carpal implant or articulate with selected portions of the carpal complex 6.

As discussed above, the various portions of the distal radial implant may include a substantially modular distal radial implant 1200. The distal radial implant 1200 may include a plurality of distal radial portions 1204 which may include a plurality of the distal radial implant segments 1206 from which may be chosen one to articulate with a natural portion of the carpal complex 6, a carpal implant, or a combination thereof. Therefore, in the kit 1600 or a supply, the selected implant may be chosen to include the distal radial implant portion 1200 that is operable to interconnect or articulate with a natural portion of the carpal complex 6 or the carpal prosthesis. It will be understood that this may be done substantially intraoperatively such that a user, such as a physician, is able to choose from the kit 1600 or selecting the portions that are required intraoperatively to allow for a substantial customization regarding the selected patient.

With reference to FIG. 41, a distal radial implant 1400 according to various embodiments is illustrated. The distal radial implant 1400 generally includes a stem 1402 and a distal radial segment 1404. It will be understood that the distal radial segment 1404 may be substantially modular from the stem 1402, such as the modular radial implant 1200. Therefore, the stem 1402 may be substantially similar to the stem 1202 and the distal radial portion 1404 similar to the distal radial portion 1204. Thus, the distal radial portion 1404 may be provided in the kit 1600 or supplied to be interconnected with a selected one of the stems 1202 for formation of the distal radial implant 1400. Regardless, it will be understood that the distal radial implant 1400 may be substantially provided as a single member for implantation and may also be included in the kit 1600 of modular portions.

The distal radial segment 1404 generally includes a body portion 1406 that is interconnected with the stem 1402. As discussed above, the body portion 1406 and the stem 1402 may be substantially formed as a single member such that the distal radial portion 1404 is not substantially separable from the stem 1402. Such a configuration may be selected for various reasons, such as strength, materials, and the like. Regardless, the distal radial portion 1404 may define an articulation region extending distally from the body 1406.

The articulating side 1408 may include a first articulating fossa or surface 1410 and a second articulating fossa or surface 1412. The first articulating surface 1410 may substantially replicate a scaphoid fossa for articulation with a scaphoid bone 8 after implantation. The second articulation surface 1412 may be designed to substantially articulate with the lunate bone 10 after implantation. Therefore, the articulating surface 1408 of the distal radial segment 1404 may be designed to substantially replicate the natural articulating surfaces of the radius 2. This may allow for a substantially natural articulation of the carpal complex 6 relative to the radius 2 after a hemi-arthroplasty regarding a resurfacing or replacement of the distal portion of the radius 2.

The articulating surface 1408 may include a bearing portion that is substantially fixed to the body 1406. Alternatively, the articulating surface 1408 may include the substantially identical material to the body 1406. For example, the body 1406 may be formed of a selected metal or metal alloy and the articulating surface 1408 may be provided as a substantially polished surface to allow for a selected articulation of the scaphoid 8 and the lunate 10 relative to the distal radial segment 1404.

The articulating surface 1408 may be defined substantially flat or straight across the articulating surface 1408. Although the articulating surface 1408 may include the depressions 1410 and 1412 to define the articulating surfaces, the articulating region 1408 may be substantially straight across its upper surface to as not to substantially hinder movement of the carpal complex. Therefore, the distal radial segment 1404 may include a height 1414, a selected length 1416, and a width 1418.

As discussed above, it will be understood that the various dimensions 1414-1418 may be substantially unique among a plurality of the distal radial segments 1404 for selection by a user substantially intraoperatively or preoperatively. Regardless, this allows the user to substantially select the portion for the distal radial implant 1400, or a modular portion for the distal radial implant 1200 to substantially suit a selected patient. Therefore, the user may be able to select whether to provide a hemi-arthroplasty or complete wrist replacement during the operative procedure depending upon the state of the patient.

With reference to FIG. 42, a distal radial implant 1450 according to various embodiments is illustrated. The distal radial implant 1450 may include portions that are substantially similar to the distal radial implant 1400 and similar reference numerals are used to reference like portions. Therefore, the distal radial implant 1450 may include the stem 1402 and a distal radial segment 1404.

As discussed above, the stem 1402 may be substantially modular relative to the distal radial segment 1404 to provide for a modular implantation of the distal radial implant 1450. In addition, a plurality of the stems 1402 and the distal radial segments 1404 may be provided for selection by a user. Alternatively, a plurality of a fully integrated distal radial implant 1450 may be provided. Therefore, the stem 1402 may be substantially integral with the distal radial segment 1404 or may be provided separately therefrom for interconnection during an operative procedure.

The articulating region 1408 of the distal radial implant 1450 may include the first articulating portion 1410 and the second articulating portion 1412. The first articulating portion 1410 may be provided to articulate with the scaphoid 8. As discussed above, the second articulating portion 1412 may be provided to articulate with the lunate bone 10.

Depending upon a selected patient's anatomy, the ulnar side of the distal radial segment 1404 may also include a recess 1452 for articulation with the ulna 4. As will be understood by one skilled in the art, the radius 2 may articulate with the ulna 4 during an anatomical motion (such as pronation or supination) of the wrist or arm portion and this may become damaged. Therefore, during an operative procedure which may be required or replacement or a resurfacing of the distal radial portion, the preparation of the radius 2, such as a resection thereof, may require removing the articulating region of the radius 2 that would generally articulate with the ulna 4. Therefore, using the distal radial implant 1450, including the recess 1452, may substantially allow an articulation of the ulna with the implant 1450 connected to the radius 2, after implantation of the distal radial implant 1450, in a substantially natural manner. It will be understood that the recess 1452 may be provided with any selected embodiment or in various embodiments of the distal radial implant and the distal radial implant 1450 is merely exemplary. For example, the recess 1452 can be added to the distal radial segment 1204*c* (FIGS. 36A and 36B).

In addition, the distal radial implant 1450 may include a curve or curvilinear portion 1454 that may be provided to substantially engage or hold a selected portion of the carpal complex 6 in a selected location. The carpal complex 6, such as after a trauma, may be unstable and require additional stabilization or retainment in a selected anatomical orientation. Therefore, the curvilinear portion 1454 may be provided on the distal radial implant 1450 for holding the selected portion of the carpal complex 6 in a location. It will be understood, again, that the curvilinear portion 1454 may be provided on any selected implant for holding the carpal complex 6 in a selected location.

Therefore, it will be understood that the illustrated embodiments are merely exemplary and not intended to limit the scope of any exemplary embodiments. Regardless, providing an articulating surfaces 1410 and 1412 that allows for substantially natural articulation of the carpal complex 6 relative to the distal radial implant 1400, 1450 may be selected to include further restricting portions such as the curvilinear portion 1454. Similarly, a resection of the radius 2 may allow or be selected to use the recess 1452 to create an articulation region for the ulna.

Figure 43:
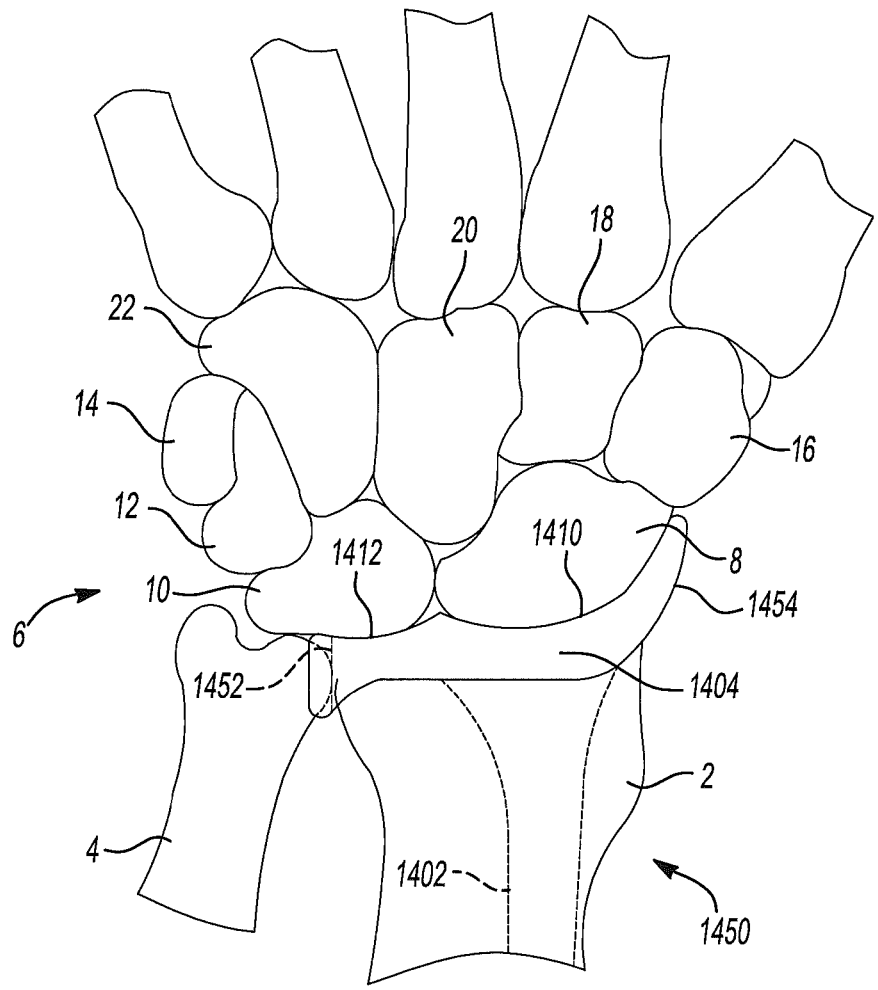
FIG. 43 is an environmental view of the distal radial implant of FIG. 42 according to various embodiments in an implanted position.

With reference to FIG. 43, the distal radial implant 1450 is illustrated exemplary implanted into a selected anatomy. The stem 1402 is implanted into the radius 2 to provide a fixation of the distal radial implant 1450 relative to the radius 2. The distal radial segment 1404 is positioned at an end, such as the distal end of the radius 2 after preparing the radius 2 for the implantation. The curvilinear portion 1454 is provided to retain a selected portion of the anatomy, such as the scaphoid 8 relative to the distal radial implant 1450. The first fossa 1410 is positioned to articulate with the scaphoid 8 while the second fossa 1412 is positioned to articulate with the lunate 10. In addition, the depression 1452 is provided to allow an articulation of the distal portion of the ulna 4 with the distal radial implant 1450.

Therefore, the implantation of the distal radial implant of 1450 may provide for articulation relative to the substantial natural or anatomical carpal complex 6 rather than positioning a carpal implant relative to the carpal complex 6. It will be understood that the distal radial segment 1404 may also include a bearing portion such as a polymer portion that may articulate with the bony portions such as the scaphoid 8 and the lunate 10. Regardless, as discussed above, the articulating surfaces 1410, 1412 may be substantially polished metal portions to allow for a smooth articulation of the natural portions of the carpal complex 6.

Therefore, it will be understood that each of the exemplary embodiments may include portions that are substantially dissimilar from the selected exemplary embodiments and may include combinations of each of the various embodiments. Therefore, the exemplary embodiments are not intended to limit the scope of the following claims but merely are provided to exemplify the portions thereof. Therefore, with reference to FIG. 44, the kit 1600 or supply may include a plurality of the stem portion 1202*a*, 1202*b* that each include a selected unique dimension, such as a length 1208*a*, 1208*b*, respectively. Furthermore, the kit 1600 may provide a plurality of distal radial portions 1204*a*, 1204*b*, 1204*c* to provide a distal radial portion according to any of the various embodiments. Also, the kit 1600 may provide a plurality of distal radial bearing members 1206*a*, 1206*b* that are operable to provide any of the various embodiments discussed above. The kit may be used by a user during procedure to select and assemble a distal radial implant that is substantial customized to a selected patient.

Furthermore, the kit 1600 may provide a plurality of the carpal implants, such as the carpal implant 54 according to various embodiments, or the carpal implant 1100 and the bearing 56 according to various embodiments for selection by a user. In this way, a user may select to provide a hemi-arthroplasty to provide a prosthesis relative to the carpal complex 6 alone or relative to the radius 2 alone. Alternatively, the user may select to provide a substantially total wrist replacement that will provide a distal radial implant and a carpal implant. While selecting either of the total wrist arthroplasty or the hemi-arthroplasty, the user may also select various portions that may be provided to allow for a customized implant relative to the patient. The selection may occur substantially intraoperative due to the kit which includes a plurality of members which may be assembled to form the selected prosthesis.

As discussed above, various implant portions, such as the distal radial implant 1415, can be used to articulate with a selected natural portion of the carpal complex 6. For example, if a fracture or other injury, due to an action or disease, of the distal radius, the distal radius can be replaced relative to the carpal complex 6. Although the carpal complex 6 may be substantially unharmed due to an injury or disease, the distal radius may necessitate replacement or a natural articulation may be improved by replacement of the distal radius portion. Therefore, the distal radius portion can be replaced with a selected implant, including those discussed above, and those described herein. As discussed above, the distal radial implant can be provided in the kit 1600 to include a plurality of portions, such as the stem portion 1202 and a plurality of the distal radial portions 1206. Therefore, a selected user, such as a physician, can select an implant combination that is suitable or appropriate for a selected patient. The selection can be based upon the amount of resection required, the condition of the bone, or other appropriate considerations.

As discussed herein, various implant portions and selections can be used to achieve a selected result for a procedure. Although any appropriate procedure can be used, exemplary methods are described herein to achieve a selected result for a selected ailment. For example, a distal radial implant can be used to replace a fractured distal radius portion. As discussed above, the implants can include both a carpal replacement and a distal radial replacement. Nevertheless, it may be selected, that only a distal portion of the radius need be replaced or is appropriately replaced. Therefore, the distal radius can include a portion that can articulate with the natural carpal complex in a substantially anatomical or natural manner or with a carpal implant.

Figure 46:
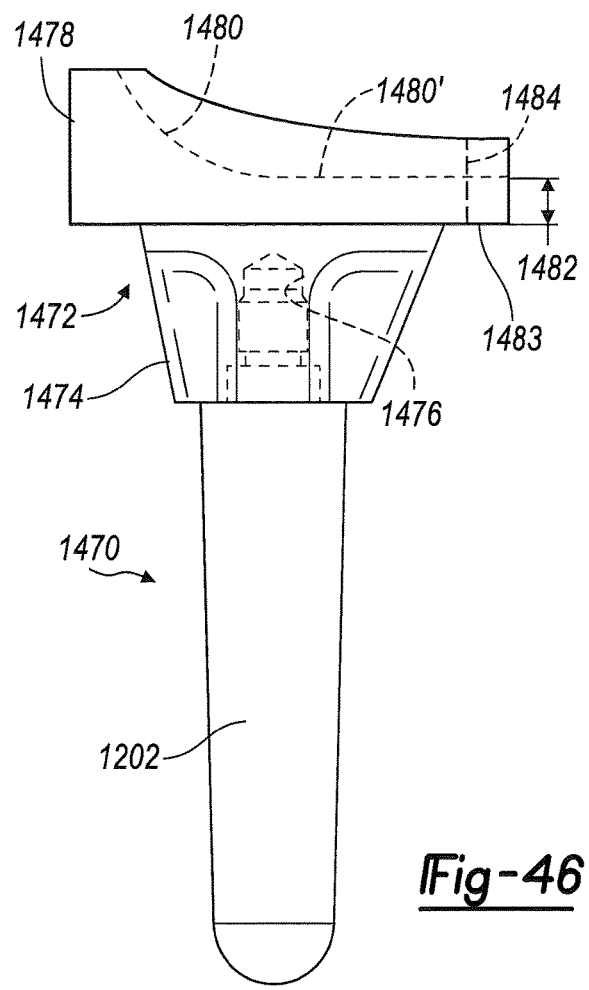
FIG. 46 is a plan view of a distal radial replacement according to various embodiments.

With reference to FIG. 46, a distal radial implant 1470 according to various embodiments is illustrated. The distal radial implant 1470 can include the stem portion 1202 or any appropriate stem. The stem portion 1202 can be formed in any appropriate manner and in any appropriate length. As discussed above, the stem portion 1202, can be provided in a plurality of sizes such as widths, lengths, geometries and the like for selected implantations. Nevertheless, the stem portion 1202 can be provided in a kit, such as that described herein or above, that includes substantially single shape, size, geometry or the like and can be interconnected with a plurality of other modular sections.

The distal radial implants 1470 can include a distal radial portion or member 1472. The distal radial portion 1472 can include a first section 1474 that includes a region to interconnect with the stem portion 1202. The interconnection portion 1476 can include any appropriate connection portion such as a taper, a thread, a locking portion, or the like. For example, as described above, the stem portion 1202 can include a thread region 1212 that can interconnect with an internal thread in the connection region 1476.

The distal radial portion 1472 can further include a carpal engaging area 1478. The carpal engaging area 1478 can include an articulation surface or articulation region 1480. The articulation surface 1480 can be formed in any appropriate manner to articulate the selected portion of the carpal complex 6 or carpal implant.

The articulation surface 1480 can include a lowermost region 1480' that extends a distance 1482 above a surface 1483 defined by the carpal engaging region 1478. The distance 1482 can be formed at any appropriate dimension for various purposes, such as substantially or selectively matching a selected anatomy. Generally, the distance 1482 can be about 0.25 mm to about 2.0 mm, or any appropriate dimension. Nevertheless, it will be understood that the distal radial portion 1472 can be provided in a plurality of sizes, including a plurality of the dimensions 1482 for selection from a kit by a user, as discussed herein.

Further, the distal radial portion 1472 can be formed of any appropriate material. For example, the entire distal radial portion 1472 can be formed of a polymer material, such as a high density polyethylene, a metal, a metal alloy, or a combination thereof. Also, the stem engaging portion 1474 can be formed of a metal or metal alloy while the carpal engaging portion 1478 can be formed of a polymer material. The polymer material can interconnect with the metal material in any appropriate manner, such as with a locking tab, be molded onto the stem engaging portion 1474, or any appropriate attachment. Nevertheless, it will be understood that the distal radial portion 1472 can be formed of any appropriate material or combinations of materials for selected purposes.

Figure 47:
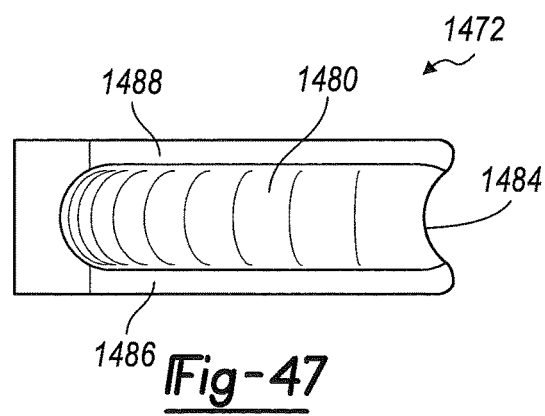
FIG. 47 is a top plan view of the device illustrated in FIG. 46.

With additional reference to FIG. 47, the carpal engaging section 1478 defines the articulating surface 1480 that can articulate with a selected portion, such as the carpal complex 6. It will be understood that the carpal articulating section 1478 can also articulate with a selected implant, such as a carpal implant, including those described above or any appropriate carpal implant. The articulating portion of the carpal implant can articulate with the carpal articulation surface 1480 in a selected manner. Alternatively, the distal radial portion 1472 can be replaced in a revision or selected procedure to implant a distal radial portion that is appropriately suited to articulate with a selected carpal implant.

In addition to the carpal articulation surface 1480, an ulna articulation surface or recess 1484 can also be provided. The ulna articulation recess 1484 is operable to articulate with a selected portion of the ulna 4 after implantation of the distal radial member 1472. This can allow for a generally natural articulation of the ulna 4 after implantation of the distal radial portion 1472. The ulna articulation recess 1484 can be formed in any appropriate manner to appropriately articulate with the ulna 4.

A first wall or portion 1486 and a second wall or portion 1488 can bound the carpal articulation surface 1480. This can help hold the various portions of the carpal complex 6 in a selected manner after positioning the distal radial member 1472. Therefore, the carpal complex 6 can be maintained substantially intact and can be held to allow for a substantially anatomical or natural articulation with the distal radial member 1472.

Figure 48:
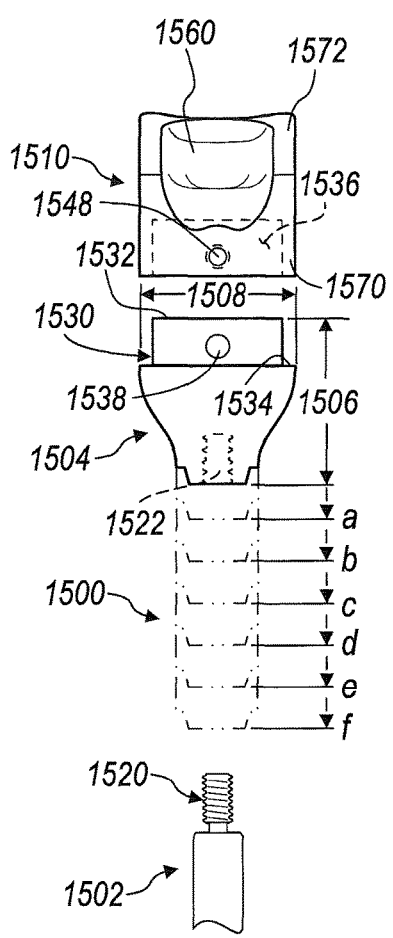
FIG. 48 is a end elevation view of a distal radial replacement according to various embodiments.
Figure 49:
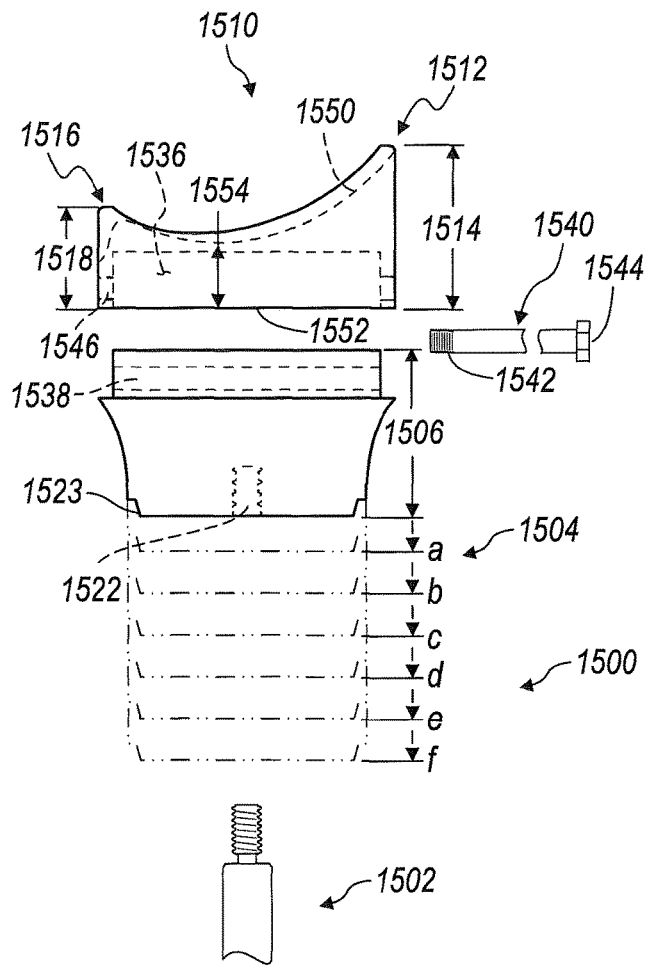
FIG. 49 is a side elevation view of a distal radial replacement according to various embodiments.

In addition to various embodiments, including those various embodiments described above, a distal radial implant can be provided with a plurality of modular portions. With reference to FIGS. 48 and 49, a distal radial implant 1500 is illustrated. The distal radial implant 1500 can include various portions such as a stem 1502. The stem 1502 can be similar to the stem 1202, described above. Regardless, the stem 1502 can generally be positioned in a portion of the bone, such as an intramedullary canal of the radius 2 to hold the distal radial implant 1500 in a selected position. The distal radial implant 1500 can further include a bone replacement portion 1504. The bone replacement portion 1504 can be provided for various selected anatomies and procedures, such as those described herein.

The bone replacement portion 1504 can include a selected dimension, such as a height 1506. The height 1506 can be provided in a plurality of different heights, such as height 1506a, 1506b, 1506c, 1506d, 1506e and 1506f, illustrated in phantom. It will be understood, as illustrated in the kit 1590 (FIG. 50) that the bone replacement portion 1504 can be provided in a plurality of sizes including at least one of the heights 1506-1506f. Therefore, it will be understood that the height 1506-1506f is a height that can be selected by a user, such as a physician, to replace a selected amount of bone that may be damaged, resected, removed, or the like. The bone replacement portion 1504 can also include a dimension such as a width 1508. The bone replacement portion 1504 can further include a plurality of widths 1508.

The distal radial implant 1500 can further include an articulating or carpal articulating section or portion 1510. The articulation portion 1510 can include a high walled or high side 1512 that includes a selected height 1514, and can also be included in a plurality of the heights 1514. Further, the carpal articulating portion 1510 can further include a low side 1516 that can include a second height 1518. Similar to the first height 1514, the second height 1518 can be provided in a plurality of dimensions along with a plurality of the carpal engaging a carpal articulating section 1510.

With continuing reference to FIGS. 47 and 48, the various modular portions of the distal radial implant 1500 can be provided according to selected embodiments. For example, the stem 1502 can include an engaging section 1520 that can engage an engaging portion 1522 in the bone replacement section 1504. The engaging section 1520 can include external threads while the bone replacement portion 1504 can include internal threads in the engaging portion 1522. This can allow the stem 1502 to be inserted into the IM canal of the radius 2 and the bone replacement portion 1504 to be threaded onto the stem 1502. Alternatively, or in addition thereto, a screw or bolt can be passed through the bone replacing portion 1504 to engage the stem 1502. Further, various other locking portions, such as a locking ring, or any other appropriate mechanism can be provided to interconnect the bone replacing portion 1504 with the stem 1502.

Further, the stem 1502 can include any appropriate geometry, extensions, shaped, or the like to engage the radius 2. For example, the stem 1502 can include an I-beam or other appropriate geometry to allow for fixation or rotation resistance after implantation of the stem 1502 into the bone, such as the radius 2. Further, various fins similar to the fins 1204 on the stem 1202, can be provided. Regardless, the stem 1502 can be interconnected with the radius 2 in a selected manner to allow for positioning of the distal radius implant 1500 Also, the stem 1502 and the bone replacement portion 1504 can be interconnected prior to implantation.

The stem 1502 can include a plurality of mechanisms to interconnect with the bone replacement portion 1504 as discussed above. Nevertheless, the bone replacement portion 1504 can include any appropriate geometry to replace a selected portion of the anatomy, such as a distal portion of the radius 2. Although the distal portion of the radius 2 may be resected for any appropriate reason such as injury, disease, and the like, the geometry of the bone replacement portion 1504 can be formed as a modular member or be custom formed for a selected individual based upon various considerations. Nevertheless, the bone replacement portion 1504 can include a stem connecting portion 1522 which can be any appropriate portion. Also a keel 1523 can extend from the bone replacement portion 1504 to engage bone to assist in maintaining a position of the portion 1504, such as to resist rotation.

Further, the bone replacement portion 1504 can include a plurality of the heights 1506 and the widths 1508. It will be understood that the difference between the various heights 1506 can be any appropriate increment, such as 1 mm, 2 mm, 3 mm, 4 mm, any fraction thereof, or any multiple thereof. Thus the bone replacing portion 1504 can be provided as a plurality of components in the kit 1590 or a kit according to any various embodiments for selection by a user. It will be understood, however, that the bone replacing portion can be provided in any appropriate manner. For example, the bone replacing portion 1504 can be telescopic. The telescopic bone replacing portion 1504 can include a single member than can be adjusted to various heights, such as selected by a user. The telescopic bone replacement portion may be infinitely adjustable or may include a plurality of discrete adjustments. Regardless, it will be understood that the bone replacement portion 1504 may be provided as one or a plurality of members and can be provided in the kit 1590.

Further, the bone replacing portion 1504 can be formed of any appropriate material such as a polymer, a metal, a metal alloy, a ceramic, or any combination thereof. For example, the bone replacing portion 1504 can be formed of a metal that can interconnect through the stem 1502 and may also be formed of a metal or metal alloy. Thus the connection between the stem 1502 and the bone replacing portion 1504 can be substantially strong and stable over a long period of time.

Further, the bone replacing portion 1504 can include a top portion or articulating connecting portion 1530. The articulating connecting portion 1530 can include a projection 1532 that extends above a ledge or depression 1534. This can allow the articulating portion 1510 to surround or encase a portion of the bone replacement member 1504 and to receive it within a depression area 1536. This can allow for a substantially strong interconnection between the articulating portion 1510 and the bone replacing portion 1504. Nevertheless, it will be understood that the articulating portion 1510 need not completely surround any portion of the bone replacing portion 1504 and the bone replacement portion 1504 may alternatively include a portion that surrounds a portion of the articulating member 1510. Therefore, it will be understood that any appropriate interconnection can be formed between the bone replacement portion 1504 and the articulating member 1510.

Further, a bore 1538 can be formed through the articulating connection region 1530 that is operable to receive a locking member, such as a bolt 1540. The bolt 1540 can include a threaded end 1542 and a driving end 1544. The threaded end 1542 can engage a threaded portion of the bore 1538 or a threaded portion of the articulating region 1546. The articulating region 1510 can also include a bore portion 1548 through which the bolt 1540 can pass. This can allow the bolt 1540 to selectively interconnect to the articulating member 1510 with the bone replacement member 1504. The bolt 1540 can pass through each of the bores 1548, 1538 and engage the threaded region 1546 to securely interconnect to the articulating member 1510 with the bone replacement member 1504. It will be understood, nevertheless, that the articulating member 1510 can interconnect with the bone replacement member 1504 in any appropriate manner. In other words, the bolt 1540 is not necessary and any other appropriate connection can be used, such as a taper, a locking ring, an adhesive, or any other selected connection.

The articulating member 1510 includes the various articulating surfaces. The articulating member 1510 can include a carpal articulation surface 1550. The carpal articulation surface 1550 can articulate with any appropriate portion, such as a carpal implant, a portion of the carpal complex, or any of the selected bones of the carpal complex 6. Therefore, the carpal articulation surface 1550 can be provided to interact with any of the appropriate portions or the articulating member 1510 can be specialized for articulation with the selected portion. The articulating surface 1550 can be formed at any appropriate distance above a bottom 1552 of the articulating member 1510. The distance 1554 can be any appropriate distance and can differ among the various members of the articulating member 1510. For example, the kit 1590 can include a plurality of the articulating member 1510 that can be used in the distal radial implant 1500. Therefore, a user can achieve a selected result by forming or selecting one of the articulation members 1510 that include a selected articulation surface 1550 for implantation.

In addition to the carpal articulating surface 1550, the articulating member 1510 can also include an ulna articulating surface 1560. The ulna articulating surface 1560 can allow for an interconnection or articulation of the ulna with the articulating member 1510. Therefore, the distal radial implant 1500 can replace substantially all of the articulations of the distal portion of the radius 2 for various purposes. Therefore a user can resect the distal portion of the radius 2 and replace it with the distal radius implant 1500 and substantially achieve a selected anatomical or natural articulation.

The various portions of the distal radial implant 1500 can be formed as a single piece member so that the stem 1502, the bone replacement member 1504, and the articulating member 1510 are not separate modular members. Although, each of these various portions can be formed as a single member they can also be formed as a plurality of portions that can be interconnected. Further, each of the portions can be formed as a single piece with one or more of the other portions. Therefore, each of the stem 1502, the bone replacing member 1504, or the articulating member 1510 can be provided as modular portions that can be interconnected with any of the other portions in a slightly less modular system or in a single piece system for a selected implantation. Thus, one skilled in the art will understand that the system can be more modular or less modular based on various considerations and manufacturing techniques or purposes.

Figure 50:
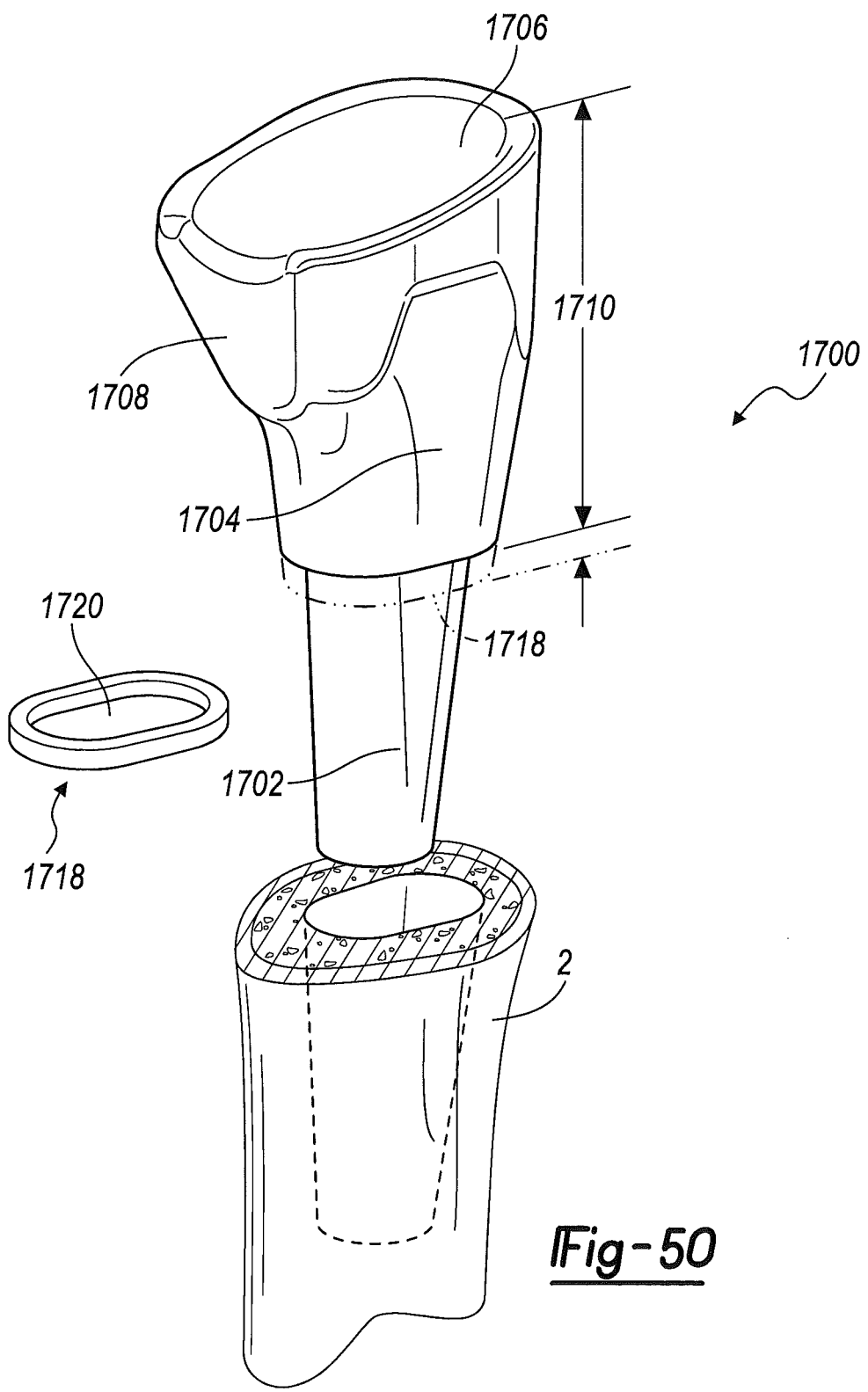
FIG. 50 is a perspective detail environmental view of a distal radial implant according to various embodiments.

For example, a single piece member, illustrated in FIG. 50 can be provided. A single piece implant 1700 can to include portions that are substantially similar to that of the implant 1500, but they can be formed as a single piece or unit. For example, the single piece implant 1700 can include a stem portion 1702, a bone replacement portion 1704, an articulation portion 1706, and an ulnar articulation portion 1708. Each of these portions can be similar to portions found in the implant 1500 save that they are formed as a single member or unit. It will be understood, however, that various portions may still be modular in the implant 1700. For example, an articulating portion can interconnect with the articulating portion 1706, such as a bearing surface or bearing member. Therefore the single piece implant 1700 can be formed of a selected material, such as a metal, and a polymer articulating portion can interconnect with the articulating portion 1706.

Though the bone replacement portion 1704 can be formed as one piece it can also be formed in a plurality of sizes or dimensions, such as height, 1710. For example, the single piece implant 1700 can be provided as a plurality of members (1700a, 1700b, 1700c) in the kit 1590 that each include a different height 1710. The height 1710 can vary between the various implant by any appropriate amount such as 1 mm, 2 mm, 3 mm, 4 mm, or any appropriate fraction or multiple thereof. Thus, it is understood that the single piece implant 1700 can be provided in addition to, or alternatively to, the modular implant 1500. Further, the height 1710 can be varied in any appropriate manner such as providing a plurality of the single piece implant 1700 providing a telescopic bone replacement portion 1704, or members that may interact over the stem 1702.

For example, the height 1710 can be altered by providing a modular member 1718 that includes a central bore 1720 that includes a geometry that would allow it to interact with the stem portion 1702. Therefore, the augmenting member 1718 can be fit over the stem portion 1702 to engage the bone replacement portion 1704. This would augment the height 1710 of the bone replacement portion 1704 by the height of the augmenting member 1718. The stem 1702, however, can still allow for connection of the single piece implant 1700 to the bone portion, such as the radius 2. The augmenting portion 1718 can be connected to the single piece implant 1700 or be held in place by fixation of the implant 1700 to the anatomy. Regardless, the implant 1700 can be provided as a substantially complete implant or be augmented by other portions, such as the augment portion 1718.

Various portions, such as the articulating member 1510 can also be formed of more than one material. For example, the articulating member 1510 can include a base 1570 that is formed of a first material and an articulating area 1572 formed of a second material. The base 1570 can be formed of a strong or hard material such as a metal or metal alloy that can substantially interconnect with the bone replacing portion 1504. The articulating surface or upper portion 1572, however, can be formed of a portion that can articulate with a bone member in a substantially long lasting or natural manner. Therefore, the upper portion 1572 can be formed of any appropriate material, such as a polymer including a high density polyethylene, a selected metal or metal alloy, a pyrolytic carbon, a ceramic, or any appropriate material. Therefore, various portions of the implant 1500, such as the articulating member 1510, can be formed of a plurality of materials to achieve a selected result. Further, the articulating member 1510 can be formed of various materials depending upon whether it articulates with a natural bone, such as a bone with a carpal complex 6, or with a member that can replace a selected portion of the carpal complex 6.

Further, the articulating member 1510 can be provided in the kit 1590 according to various embodiments that can be selected based upon an observed condition. For example, during a surgical planning, it may be determined that a live view by a user, such as a physician, is necessary to determine whether any of the carpal bones need to be replaced. Therefore, a kit 1590 can include both an articulating member 1510, that is able to articulate with a natural bone and one that is able to articulate with an implant for the carpal complex 6.

In addition to the distal radial implant 1500 a carpal implant can be provided to articulate directly with a portion of the radius 2, with reference to FIG. 20. As will be understood by on skilled in the art a hemi-arthroplasty of the wrist can also include replacement of substantially only the carpal bones 6. Thus the carpal implant 50, according to various embodiments can be implanted into the carpal complex to articulate with a natural portion of the radius 2. Further, as discussed herein the kit 1590 can also include the carpal implant 50. Thus, a user can determine intraoperatively whether a hemi-arthroplasty can be performed, on either of the radius or the carpal complex 6.

Further, as discussed herein, the modular distal radial implant 1500 can be assembled to articulate with the natural carpal complex 6 or with the carpal implant 50. Also, as discussed herein, the articulating member 1510 can be changed during a revision procedure to articulate with a carpal implant implanted during a revision procedure. Thus, it will be understood, that a hemiarthroplasty or total arthroplasty of the wrist can be performed. If a hemiarthroplasty is selected it may be of either the distal radius or the carpal complex 6.

Figure 51:
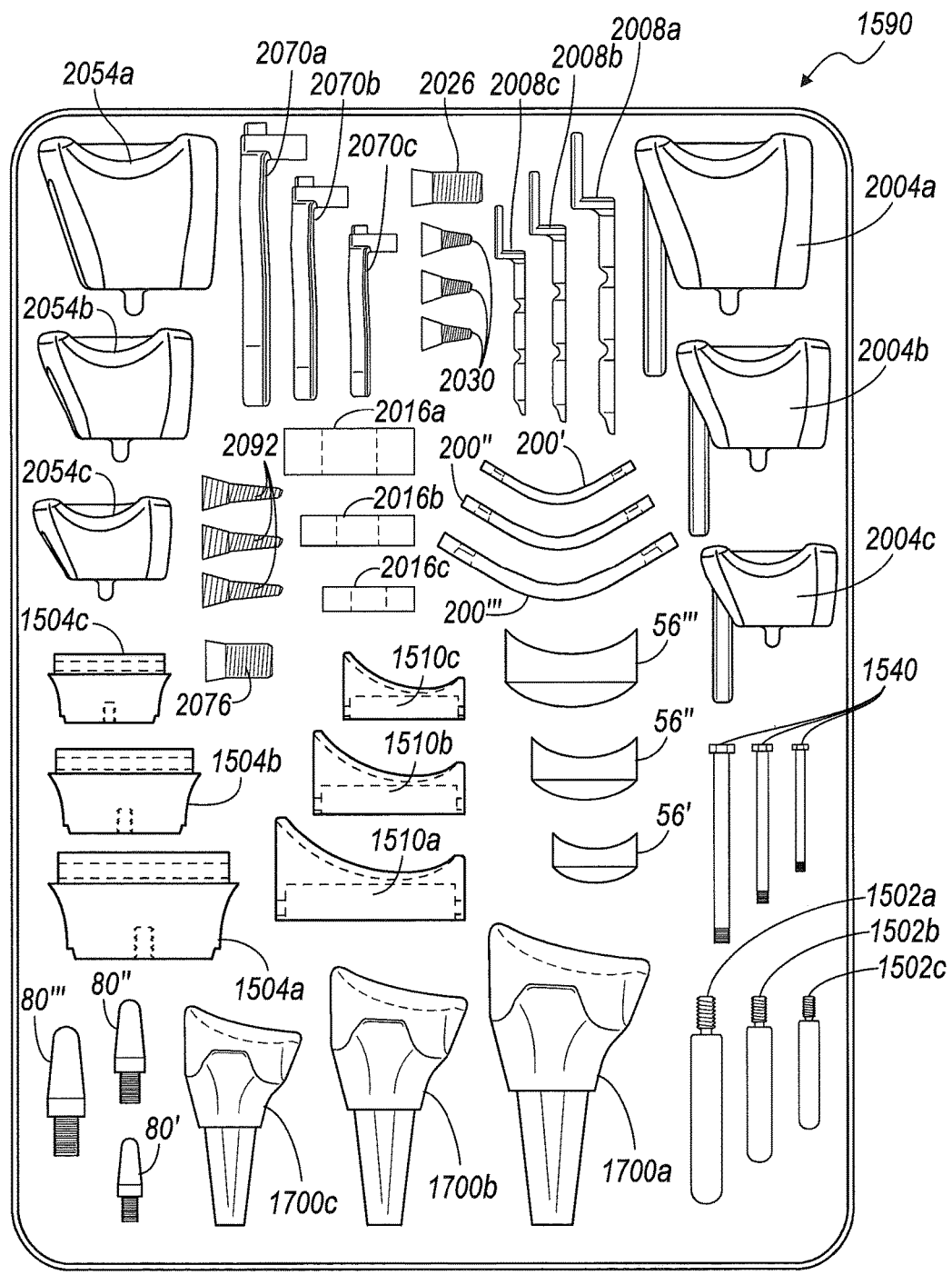
FIG. 51 is a plan view of a kit including various components for a bone replacement system.

The kit 1590, with reference to FIG. 51, can include the distal radial implant 1500, or any distal radial implant according to various embodiments. The distal radial implant 1500 can be provided in modular pieces, such as those discussed above, or as a single piece member. For example, however, the articulating member 1510 can be provided in various sizes and configurations, such as 1510a, 1510b, and 1510c. The various sizes can be selected by a user, such as a physician, based upon an observed requirement or position. The various sizes of the implant members can be provided in the kit 1590 and the user can select them either pre-operatively or intra-operatively. Therefore, the various portions of the kit 1590 can be provided whether or not the user has pre-operatively determined a selected size or determines intra-operatively the configuration for a selected patient.

Further, the kit 1590 can include a plurality of the bone replacement portions 1504, such as the portions 1504a, 1504b, and 1504c. Each of the various bone replacement portions 1504 can include a different height 1506, such as those discussed above. It will be understood that any appropriate number of the bone replacement portions 1504 can be provided, such as 10 bone replacement portions 1504 each including a different height 1506 that differs by about 1 mm. Nevertheless, it may be selected to provide less or more of the bone replacement member 1504 based upon a selected procedure or use. As mentioned above, however, a single bone replacement member 1504 can be provided that includes a telescopic portion.

Further, the kit 1590 can include the stem 1502 in a plurality of sizes or configurations such as the stem 1502a, the stem 1502b, or the stem 1502c. Again, the different sizes or configurations of the stems 1502 can be provided for selection by a user either pre-operatively or intra-operatively. Nevertheless, the plurality of the sizes, configurations, or the like can be used by a user to achieve an optimal or a selected result.

The kit 1590 can further include the connecting member 1540 such as the bolt. It will be understood that various other connecting members may be provided if selected. For example a snap ring, a cotter pin, or other devices can be provided.

The kit 1590 can also include, or alternatively include, the implant 1700. The implant 1700 can be included in a plurality of sizes 1700a, 1700b, and 1700c. Each of these sizes can vary by any appropriate amount, as discussed above. Also, it will be understood, that the kit 1590 can include only the implant 1700 and not the implant 1500, or both.

The kit 1590 can further include a carpal implant or replacement portion. The carpal implant can be provided according to various embodiments or provided according to a plurality of embodiments. Further, the carpal implant can be provided in a plurality of sizes. The carpal implant can include a flange of various sizes 200', 200", 200'". The carpal implant can be provided in the kit 1590 to include the stem 87', 80", 80'", in various sizes. Also the wrist bearing component 56', 56", 56'" can be provided in the kit 1590 in various sizes. It will be understood that any appropriate number of sizes of the various components can be provided in the kit 1590, and three sizes is merely exemplary.

Therefore, the user can obtain the kit 1590 and intra-operatively determine an appropriate or more optimal configuration. Thus, not only can the user determine whether a hemi-arthroplasty of either the carpal bones or the radius is selected or whether a hemi- or total arthroplasty is required to replace both the distal radius and the carpal bones. Further, the user can determine and select the amount of radial resection and the user may select a size of the bone replacement member to achieve a result. The user may also determine an appropriate size or configuration of the stem 1502, the articulating member 1510 and other appropriate considerations. It will be understood, however that the kit 1590 can include more modular components or instruments. For example, various adhesives, impacters, drill motors, reamers, saws, or the like can be used or provided in the kit 1590 for use by a user. Nevertheless, the various modular components are illustrated in the kit 1590 merely for purposes of the present discussion.

It will be understood that the implant members, such as the distal radial implant 1500, can be used according to any appropriate method, such as for a hemi-arthroplasty, a total arthroplasty, or any selected procedure. Nevertheless, the distal radial implant 1500 can be used according to the method described herein and illustrated in FIGS. 52-55. It will be understood that the following method described and illustrated is merely exemplary and not intended to limit the application or scope of the present teachings.

Figure 52:
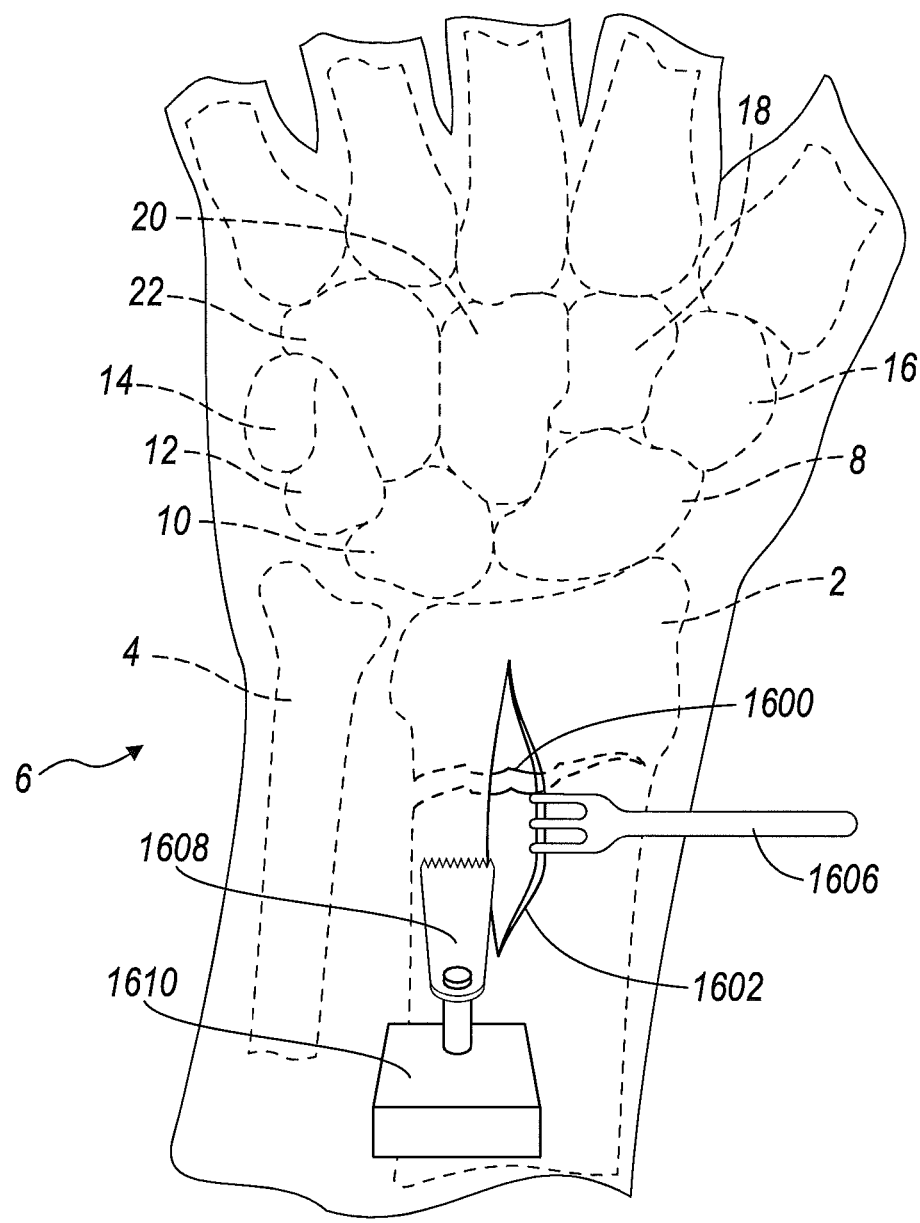
FIG. 52 is an environmental view of preparing an anatomical portion for a bone replacement.

With initial reference to FIG. 52, the radius 2 may include a fracture 1600. The fracture 1600 can be formed according to any appropriate reason, such as an injury, a disease, or the like. Nevertheless, the fracture 1600 can be formed in a radius 2, such as in a distal region of the radius 2 that may be replaced with a distal radial implant, such as the distal radial implant 1500. The fracture 1600 may be determined according to any appropriate procedure, such as an x-ray, a magnetic resonance imaging scan, a computer tomography scan, or the like. Nevertheless, once the fracture 1600 is discovered, a user, such as a physician, may determine whether the fracture 1600 can heal under natural or anatomical conditions or whether a portion of the radius 2 may be replaced with a distal radial implant. It will be understood that the fracture 1600 in the radius can be unique and none of the carpal bones in the carpal complex 6 may be compromised or fractured or various bones in the carpal complex 6 may also be injured.

To achieve a resection of the radius 2, an incision 1602 can be formed through various soft tissues 1604 of a patient. The soft tissue 1604 can include skin, dermis, muscle, tendons, ligaments, adipose tissue, and other soft tissue portions. Nevertheless, the incision 1602 can provide access to the radius 2 near the region of the fracture 1600. After the incision 1602 has been formed, it can be augmented with various instruments, such as a retractor 1606. The incision 1602 can therefore be made into any appropriate dimension, but can initially be formed in an appropriate dimension to achieve access to the radius 2 for resecting a portion of the radius 2 and implanting a selected prosthesis. For example, the incision 1602 can include a dimension, such as a length of the incision that is about 1 cm to about 15 cm. This can achieve a reduced invasive procedure for either a hemi- or a total arthroplasty of any portion of the wrist. After the incision 1602 is formed, any appropriate resecting instrument, such as a saw 1608, that is interconnected with an appropriate motor 1610 can be used to resect a selected portion of the radius 2. For example, the radius 2 can be resected near the incision 1600 or proximal to the fracture 1602.

With reference to FIG. 53, the radius 2 can be resected any appropriate amount, such as at a distance of 1612. The distance 1612 can be any appropriate amount and may depend upon the position of the fracture 1600, the strength of the bone surrounding the fracture 1600, or any other appropriate consideration. Nevertheless, the distance of the resection 1612 can be used to assist in selecting an appropriate size for the bone replacement member 1504. Also, the user, such as a physician, can monitor or observe the anatomy of the patient to determine whether or what size of the bone replacement portion is appropriate for a selected patient regardless of the amount of bone resected. The resection distance 1612 can be similar or related to the dimension, such as the height 1506 of the bone replacement member 1504.

With reference to FIG. 54, the radius 2 is initially resected at an appropriate location to allow repair of the fracture 1602. It will be understood that once the radius 2 has been resected a selected amount, that various preparatory steps can be performed to allow for implantation of the distal radial implant 1500. For example, the IM canal of the radius 2 can be reamed with any appropriate tool to allow for application of the stem 1502 into the radius 2. Further, a reaming or resection of a portion of the radius 2 can be performed to allow for positioning of the keel 1523 of the bone replacement portion 1504. As discussed above, the keel 1523 can interconnect with a selected portion of the radius 2 to resist rotation of the bone replacement portion 1504 after implantation thereof. Therefore, it will be understood that the radius 2 or any other appropriate bone portions, such as bones of the carpal complex 6 or the ulna 4 can be prepared for implantation of the distal radial implant 1500 or any appropriate distal radial implant according to various embodiments. Further, it will be understood that the radius 2 or any other bone portions need not be prepared for implantation of the various portions of the distal radial implant 1500, but rather the various portions of the distal implant 1500 can be interconnected with the radius 2 and implanted therein, such as with impaction.

The stem 1502, with reference to FIG. 54, can be positioned in the IM canal of the radius 2. The stem 1502 can be positioned in the IM canal in any appropriate manner. For example, the IM canal can be reamed to prepare an opening for positioning the stem 1502 therein and for positioning various other materials, such as antibiotics, adhesives, bone cements or the like. Alternatively, or in addition thereto, the stem 1502 can be driven or impacted into the IM canal of the radius 2 without any prior preparation. Regardless, the stem 1502 can be positioned relative to the radius 2 to allow for interconnection of the various other portions of the distal radial implant 1500.

The bone replacement portion 1504 can be selected based upon the anatomy of the patient. The bone replacement portion 1504 can be connected to the stem 1502 either before or after the stem is positioned in the radius 2. As discussed above, the amount of resection 1612 can be used to select the bone replacement portion 1504. For example, it may be selected that the entire amount of resection 1612 can be replaced with the bone replacement portion 1504. The articulating portion 1510 would then only replace the articulating surface or geometry of the radius 2. Alternatively, the bone replacement portion 1504 may only replace a portion of the bone resected 1612 and the articulating member 1510 can also replace a portion of the resected bone and the articulating surfaces. Nevertheless, the various sizes provided in the kit 1590 can be used by a user, such as a physician, to achieve the selected result with the patient.

Also, the various members or trialing components can be used to trial various sizes to achieve an optimum or selected configuration for the distal radius replacement 1500. The trialing components, though not specifically illustrated, can be substantially similar to the components of the distal radial implant 1500. The trialing components can simply be temporarily interconnected to allow trialing of the articulation of the carpal complex 6 relative to the radius 2 and the ulna 4 to achieve a selected anatomical or natural articulation.

The bone replacement portion 1504 can be selected from a plurality of sizes provided in the kit 1590, as described above. Once the selected bone replacement portion 1504 is selected from the kit 1590, it can be interconnected with the connecting portion 1520 of the stem 1502. As discussed above, the keel portion 1523 can be positioned in a reamed out area in the radius 2 or simply impacted into the radius 2. Alternatively, or in addition thereto, the keel 1523 may not be provided and the bone replacement portion 1504 contacts a resected surface of the radius 2. Regardless, various other components, such as antibiotics, other medications, cements, or the like, can be provided to interconnect the bone replacement portion 1504 with the radius 2 and the stem 1502. It will be understood that the various components can be sized and orientated to be passed through the incision 1602 formed in the soft tissue 1604.

Figure 55:
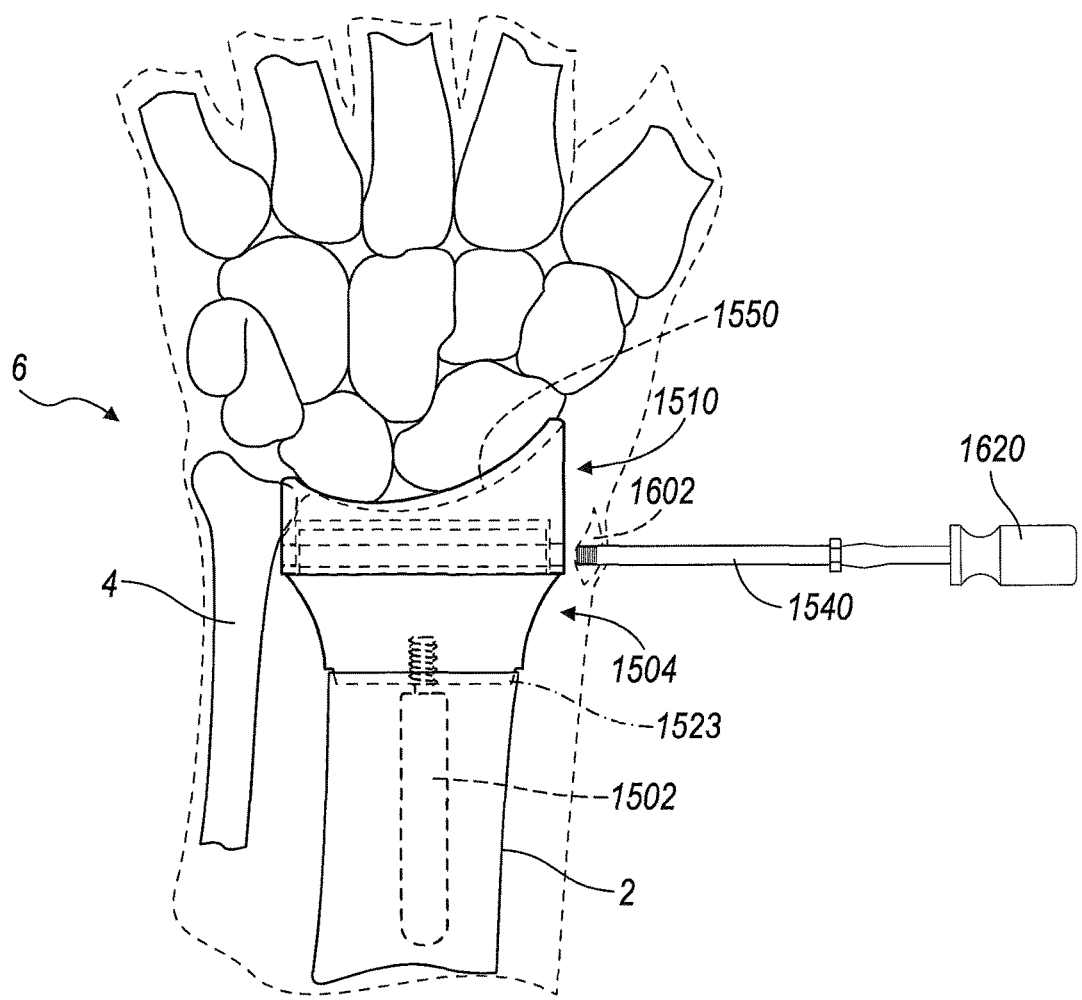
FIG. 55 is an environmental view of an implant positioned relative to a portion of the anatomy according to various embodiments.

With reference to FIG. 55, the articulating member 1510 can be positioned relative to the bone replacement portion 1504. As discussed above, the articulating member 1510 can be provided in a plurality of heights 1514, 1518 and a user, for implantation relative to the radius 2, can select an appropriate height. The articulating member 1510 further includes an articulating surface 1550 that can articulate with various portions of the carpal complex 6. It can be further understood that the depth or height of the articulating surface 1550 can also vary and be selected. Therefore, again, the user can select an appropriate articulating member 1510 that can include any appropriate orientation of the articulating surface 1550.

Further, the articulating member 1510 includes the ulna articulating surface 1560 with which the ulna 4 can articulate. Therefore, the appropriate dimensions of the articulating member 1510 can also include determining the appropriate location of the articulating surface 1560 for the ulna.

Nevertheless, the user, such as the physician, can select an appropriate articulating member 1510 from the kit 1590. Further, it will be understood that the trialing portion for the articulating member 1510, though not specifically illustrated, can be provided for trialing to determine an appropriate dimension, geometry, and like of the articulating member 1510.

Once the appropriate articulating member 1510 has been selected, it can be interconnected with the bone replacing portion 1504. The locking member, such as the locking screw 1540, can be provided through the incision 1602 to lock the bone replacing member 1504 with the articulating member 1510. Any appropriate driver, such as a hex head driver 1620, can be provided to interconnect the bone replacing portion 1504 with the articulating member 1510. The driver 1620 can be manual or powered to assist in interconnecting or positioning the locking member 1540.

Therefore, it will be understood that the distal radial replacement 1500 can be interconnected with the radius 2 to replace a selected portion of the anatomy. Though the reasons for the positioning of the distal radial member 1500 can be varied, a fracture can indicate positioning the distal radial implant 1500 relative to the radius 2. As discussed above, the various modular portions can be provided in the kit 1590 to allow for selection by a user of an appropriate geometry, size, orientation and the like.

Further, the modular portions of the distal radial implant 1500 can allow for easy revision or changing of the implant. Since the bone replacement portion 1504 can be modular from the stem 1502 and the articulating member 1510 can be modular from both the stem and the bone replacing portion, the various portions of the implant 1500 can be individually selected for implantation. Further, if a revision procedure is required or indicated, a user, such as a physician, can select to do a replacement of the articulating member 1510, the bone replacement member 1504, or any appropriate portions and replace them with a selected other portions. For example, the articulating member 1510, that can initially be used or allowed to articulate with the natural bone of the carpal complex 6 and can be later replaced to articulate with the carpal implant 50. Therefore, during a revision procedure, the articulating member 1510 can be removed from the modular implant 1500 and replaced with a portion that can articulate with the carpal implant. Further, during a revision or second procedure, the articulating member can be replaced with a replacement articulating member of varying configurations as selected by a user. Therefore, the modular implant 1500 can allow for ease of revision procedure or for the intraoperative determination of an appropriate implant assembly.

In addition to the various modular assemblies discussed above, which can be used in hemi- or total wrist arthroplasties, various other modular members can be used. The modular members can be included for various reasons, such as fracture fixation, soft tissue fixation, bone replacements, or any other appropriate purposes. As discussed above, various modular portions can be provided for bone replacement of a selected amount of bone depending upon the amount of bone that is resected or damaged. Further, various modular, semi-modular components, or single piece components can be provided for fracture fixation or stabilization.

Figure 56:
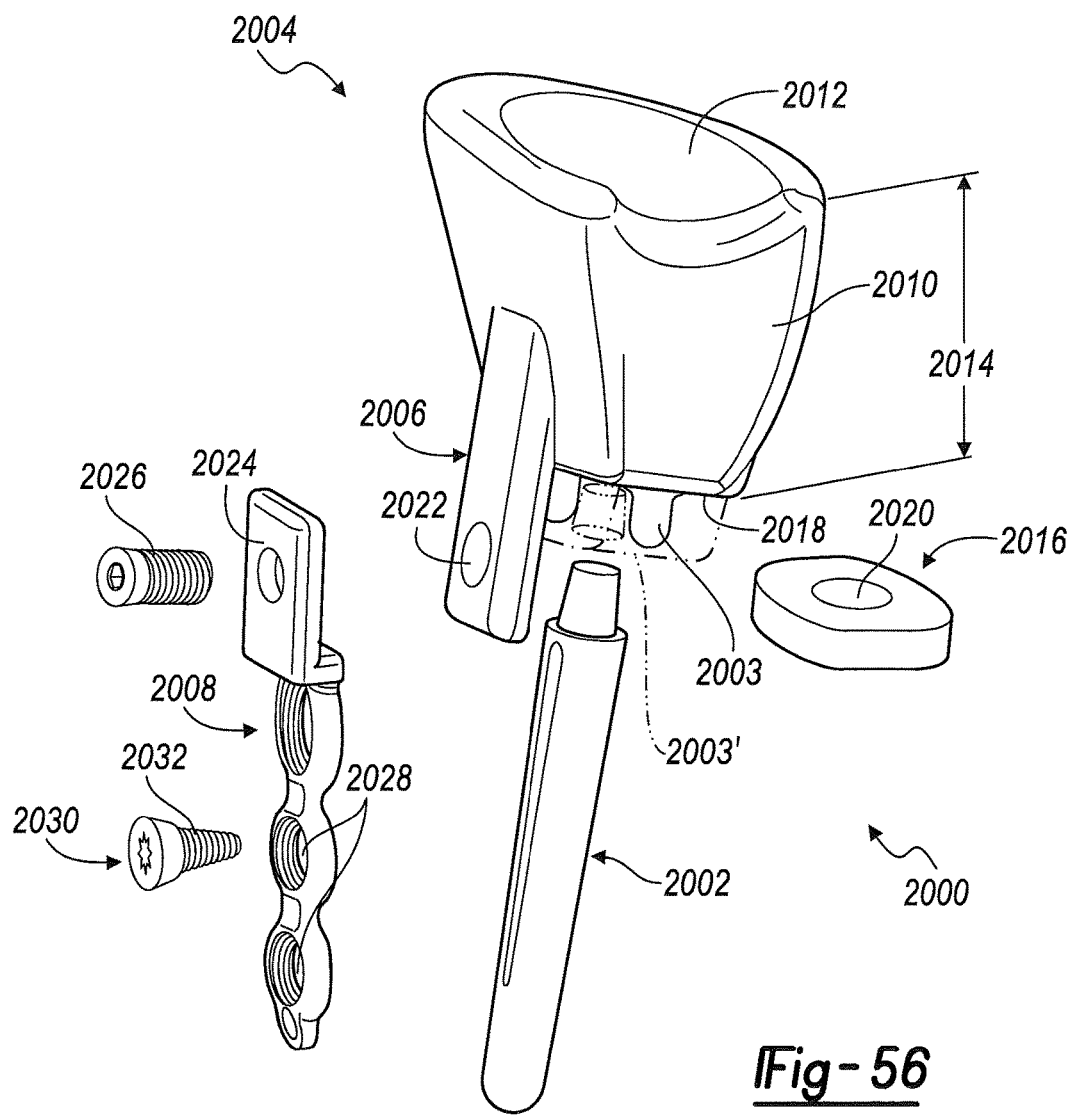
FIG. 56 is an exploded perspective view of a distal radial prosthesis according to various embodiments.
Figure 57:
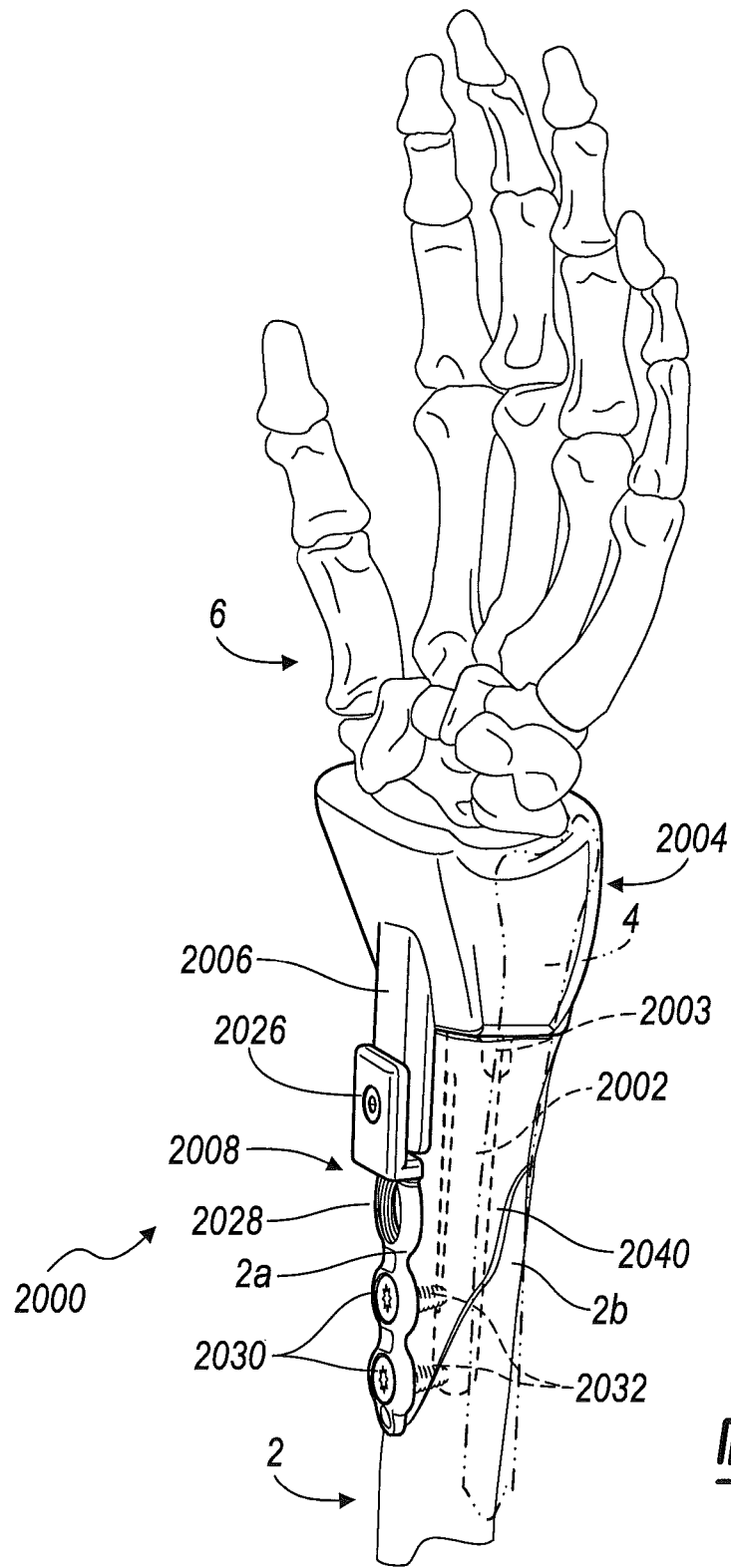
FIG. 57 is an environmental perspective view of the distal radial prosthesis of FIG. 56.

With reference to FIG. 56, a distal humeral implant or system 2000 is illustrated. The distal radial implant 2000 can include a stem 2002, which can be any appropriate stem, such as the stem 1502, stem 1202, or any appropriate stem. It will be understood that the stem can be substantially cylindrical, annular, polygonal, "I"-shaped, "T"-shaped in cross-section, or the like. The stem 2002 can be fit or implanted into a selected bone portion, such as the radius 2, to assist in holding a bone replacement section 2004 relative to the radius 2, as illustrated herein. The stem 2002 cannot only hold the bone replacement section 2004 relative to the radius 2, but may also assist in anti-rotation, or the like of the implant 2000. Also projections 2003, at any appropriate shape, size, etc., can be provided to extend from the bone replacement portion 2004 and engage the bone 2 (FIG. 57). One skilled in the art will understand that an alternative projection portion 2003' can also be provided. The alternative projection 2003' can include an outer dimension to engage a portion of the bone 2 and also in clued a region to engage or receive the stem 2002. The projection 2003' can be any appropriate portion to engage the bone, including those taught above. One skilled in the art will also understand that more than a single projection can be provided.

The distal radial prosthesis 2000 can also include a flange member 2006. The flange member 2006 can be formed as a single piece with the bone replacement portion 2004. Alternatively, the flange 2006 may be completely or partially modular as discussed further herein. In addition, a flange or flange extension 2008 can be provided to interconnect with the flange 2006 in any appropriate manner, including those discussed herein. The distal radial assembly 2000 can be interconnected in any appropriate fashion and implanted into an anatomy, such as interconnected with the radius 2.

The bone replacement portion 2004 can include appropriate portions or sections. For example, the bone replacement portion 2004 can include an ulnar articulation section 2010. The ulna articulation section 2010 can allow for articulation with the natural ulna 4, a prosthesis and/or a graft that are connected with the ulna 4. Further the bone replacement portion 2004 can include a carpal complex articulation section 2012. The carpal articulation region 2012 can articulate with a portion of the carpal complex 6, a carpal bone replacement prosthesis, including those discussed above, and/or any other appropriate portion.

The bone replacement portion 2004 can also be provided in a plurality of sizes. For example, the bone replacement portion 2004 can include a height 2014 that can vary between a plurality of bone replacement portions and can be selected for various purposes. Further, as discussed above, a modular member 2016 can be provided to interconnect with a proximal bone contacting side 2018 of the bone replacement portion 2004 to assist in adjusting the height 2014 of the bone replacement portion 2004 if only a single bone replacement portion 2004 is provided. As discussed above, the distal radial prosthesis 2000 can be included in a kit, such as the kit 1590. The kit 1590 can include the bone replacement portion 2004 in a plurality of sizes or include a plurality of the augment members 2016. The augment members 2016 can be similar to the augment member 1718 (FIG. 50) and perform a similar function. For example, the augment member 2016 can include a central aperture 2020 to pass over a portion of the stem 2002. The augment 2016 can allow the stem 2002 to assist in positioning the augment portion 2016 relative to the bone replacement portion 2004.

The bone replacement portion 2004 can be formed of any appropriate material, such as a metal, a metal alloy, a polymer, synthetic material, composite of metals, polymers, pyrolytic carbon, or other appropriate materials. It will be understood that the bone replacement portion 2004, the stem 2002, the augment portion 2016, and the flange extension 2008, can be formed of any appropriate material. The bone replacement portion 2004, however, can be formed partially or completely of a material that is appropriate for articulation with the carpal complex 6 or the ulna 4. Any appropriate material can be used for this, such as an ultra high molecular weight polyethylene, pyrolytic carbon, and other appropriate materials.

The flange 2006 can be formed integrally or as a single portion with the bone replacement portion 2004. The flange 2006 can be also integrated into the bone replacement portion 2004 in any appropriate manners, such as welding, melding, melting, casting, forging, or the like. The various techniques can also include mechanical connections such as a screw or latch. Nevertheless, the flange 2006 can include a connection section 2022 that is formed near a selected portion of the flange 2006, such as an end thereof. The connection portion 2022 can be used to interconnect with various members, such as the flange extension 2008, or with a structure to which the distal radial prosthesis 2000 is positioned. For example, a screw or other appropriate member can be passed through the connection portion 2022 to connect to a selected portion of bone, such as the radius, or the flange extension 2008.

The flange extension 2008 can be interconnected with the flange 2006 at the interconnection portion 2022 for various purposes. For example, the flange 2006 may be provided in a substantially single length in the kit 1590 or the kit 1590 may include a plurality of the flange extensions 2008 of different sizes to allow for use in multiple or plurality of different situations. It will be understood that although the flange 2006 can be provided in a plurality of lengths with a plurality of the bone replacement portions 2004, the flange extension 2008 can also be provided to extend a length of the flange 2006 relative to the bone replacement portion 2004 for various purposes.

The flange extension 2008 can include a flange interconnection portion 2024 that can allow for interconnection of the flange extension 2008 with the interconnection portion 2022 of the flange 2006. For example, a bolt or flange connection screw 2026 can be provided to interconnect the flange extension 2008 with the flange 2006. Other appropriate mechanisms, such as a cotter pin, rivet, adhesive, ball joint, snap-fit, or the like may be used to interconnect the flange extension 2008 with the flange 2006. Further, as briefly discussed above, the flange 2008 can be provided in a plurality of sizes, such as in the kit 1590, to be selectively interconnected with the flange 2006 to achieve a selective length.

The flange extension 2008 can include or define bone connection portals or apertures 2028 that can allow for interconnection of the flange extension 2008 with a selected bone portion, such as the radius 2. An appropriate bone connection member, such as a screw 2030 can be provided to interconnect the flange extension 2008 with the appropriate bone member. The screw 2030 is merely exemplary and any appropriate connection portion can be provided, such as a pin, a pop rivet, an anchor, a bolt, or any other appropriate connection member.

The bone connection apertures 2028 can be provided in any appropriate manner, for example, the apertures 2028 can be threaded, smooth, partially threaded, countersunk threaded, or the like. Further, it will be understood that the apertures 2028 can include machine threads to engage a machine thread portion of the screw 2030 while the screw 2030 can include a shank 2032 that includes substantially bone-engaging threads. It will be further understood that the screw 2030 can interconnect with the apertures 2028 of the flange extension 2008 to assist in resisting or eliminating back out of the screw 2030.

The distal radial prosthesis 2000 can be used for any appropriate purpose, such as for implantation into the radius 2, exemplary illustrated in FIG. 57. It will be understood that the prosthesis 2000 can be implanted in various embodiments in any appropriate bone portion or any appropriate bone segments and a distal radius 2 is merely exemplary. As discussed above, the radius 2 can be prepared in any appropriate manner, such as illustrated and discussed in relation to FIG. 53. Briefly, a selected portion of the distal radius can be resected, such as the distance 1612 and an appropriate size of the bone replacement section 2004 or an appropriate combination of the bone replacement section 2004 and the augment members 2016 can be selected from an appropriate inventory, such as the kit 1590.

Once the appropriate distance 1612 has been resected of the radius 2 and the appropriate bone replacement portion 2004 has been selected, the radius 2 may still include or be injured with a fracture 2040. The fracture 2040 can be a fracture, such as a severely comminuted spiral, or diaphysal fracture. The fracture 2040 can be formed in the radius 2 at any time, such as when the radius may have been injured, requiring the distal radial implants 2000. The fracture 2040, however, may also have occurred after the initial procedure of implanting the prosthesis 2000 when only a portion of the initial flange 2006 is included. A flange or the flange extension 2008 can then be added at any appropriate subsequent time. It will be understood, therefore, that the distal radial prosthesis 2000 can be used both for a primary and a revisionary procedure, depending upon the appropriate requirements. Nevertheless, the flange 2006 and/or the flange extension 2008 can be provided to extend a distance proximally along the radius 2 from the bone replacement portion 2004. This may be selected, for example, if the extreme distal portion of the radius 2002 was unsalvageable, due to an injury, disease, or the like. But a proximal portion of the radius 2 is salvageable, and includes a weakness or injury, such as a fracture 2040. The flange 2006 and flange extension 2008 can extend generally parallel to or at an angle to the longitudinal axis of the stem 2002.

The flange extension 2008 can be interconnected relative to the flange 2006 in an appropriate manner. As discussed above, the flange interconnection mechanism 2026 can be used to interconnect the flange extension 2008 with the flange 2006. At any appropriate time, the bone connection screws 2030 can also be passed through selected portals 2028 of the flange extension member 2008 or the flange 2006 to interconnect with the radius 2. As illustrated, the bone screws 2030 can pass through selected portions of bone, including the radius 2, to provide a fixation of the bone relative to the prosthesis 2000 and also provide for a compression force, such as to assist in healing.

The bone screws 2030 can pass through both a first portion 2A and a second portion 2B of the radius 2 to span the fracture 2040 and assist in providing a compressive force relative to the portions 2A, 2B of the radius 2. Therefore, the fracture 2040 can be held and stabilized with the bone screw 2030 and the flange 2006 or the flange extension 2008. It will be further understood that various soft tissue members can be interconnected with the flange 2006, 2008, such as tendons, to assist in fixing soft tissue relative to the prosthesis 2000, as one skilled in the art will understand.

Figure 58A:
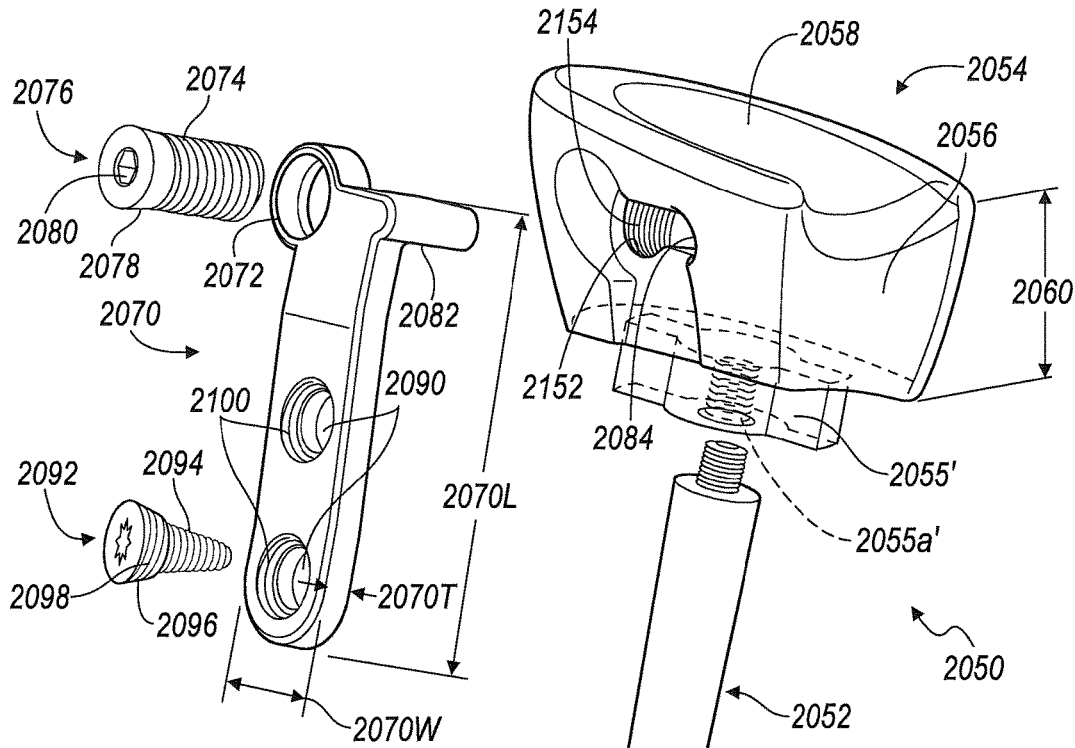
FIG. 58A is an exploded perspective view of a distal radial prosthesis according to various embodiments.

Further, a prosthesis system 2050, illustrated in FIG. 58, can be provided to be more modular than the distal radial prosthesis 2000 and also includes various beneficial features and similar features to the prosthesis 2000. With continuing reference to FIG. 58, the modular flange distal radial prosthesis 2050 can include portions substantially similar to the distal radial prosthesis 2000, illustrated and described above. Various similar portions will be mentioned briefly, but not described in detail.

The modular distal radial prosthesis 2050 can include a stem 2052 that can be provided in any appropriate length, cross-section or the like, such as those described above. Further, the modular distal radial prosthesis 2050 can include a bone replacement portion 2054. The bone replacement portion 2054 can include portions or sections that are similar to the bone replacement portion 2004 discussed above. For example, the bone replacement portion 2054 can include an ulna articulation section 2056 and a carpal complex articulation section 2058. It can also include projections 2055 to engage the radius 2. As discussed above alternative projections, such as a projection section 2055' can be provided with the bone replacement section 2054. Also, a stem engaging portion 2055'*a* can be provided in the projection section 2055'. The projection 2055, 2055' can be any appropriate portion to engage the bone, including those taught above. As discussed above more than one projection section can be provided.

It will be understood that the articulation sections 2056, 2058 can be similar to those described above or provided in any appropriate manner. Further, the bone replacement portion 2054 can be provided in any appropriate manner or of any appropriate material. For example, the bone replacement portion 2054 can include a height 2060 that can be variable or can be augmented with an augment section, such as the augment section described above. A plurality of the bone replacement portions 2054 can be provided in a kit, such as the kit 1059 in any appropriate size to be selected for a procedure, either pre- or intraoperatively. Also, the bone replacement portion 2054 can be formed of any appropriate material, such as a metal, metal alloy, polymer, pyrolytic carbon, or combinations thereof or composites thereof.

The modular distal radial implant 2050 can also include a modular flange section 2070. The modular flange section 2070 can include a flange attachment portion 2072 and a flange attachment member 2074. The flange attachment segments or members 2074 can be any appropriate member, such as a screw. The flange attachment member 2074 can include a threaded shank 2076 and a head 2078. The head can define a drive section 2080, such as an internal hex drive segment. It will be understood that the flange attachment member 2076 can be any appropriate member and can include appropriate threads, such as including a single thread through the head 2078 or include a second thread segment on the head 2078 to engage a selected portion of the modular flange 2070.

The modular flange 2070 can also include a stabilization projection 2082 that can engage a portion of the bone replacement member 2054. The stabilization section 2084 can be provided in any appropriate manner, such as to resist rotation of the modular flange 2070, resist back out of the modular flange 2070, or any appropriate reason. The stabilization section 2084 can be keyed to a configuration of the stabilization projection 2082. The stabilization section 2084 can also be provided to allow for the movement of the flange 2080, as discussed further herein. The interconnection of the modular flange 2070 with the bone replacement portion 2054 will be discussed in further detail herein, but can be provided to assist in positioning the modular flange 2070 relative to the bone replacement portion 2054 as a part of the prosthesis assembly system 2050.

The modular flange 2070 can also include apertures 2090 to allow for passage of connection members, such as bone screws 2092. The bone screw 2092 can include a threaded shank 2094 and a head 2096, which can include an optional thread 2098. The apertures 2090 can receive the screw 2092 to engage a bone portion, such as the radius 2 as described above. Therefore, the apertures 2090 can include internal threads 2100, if selected. The internal thread 2100 can assist in reducing back out of the screw 2092, increase interconnection of the screw 2092 with the modular flange 2070, or other appropriate reasons. Further, the threads on the shank 2094 and the threads on the head 2098 can be the same, or different, such as a machine and a bone thread.

It will be understood that the modular flange 2070 can be provided in a plurality of lengths 2070L, widths 2070W, and thicknesses 2070T. A selected modular flange 2070 can be provided or selected from the kit 1590, or any other appropriate kit or stock, to be used with the prosthesis system 2050. Therefore, the prosthesis system 2050 can be customized intraoperatively, preoperatively, or at any appropriate time. The prosthesis assembly 2050 can be used to replace a portion of the radius 2 for various reasons. Also, the flange 2070 can be interconnected to the bone replacement portion 2054 during a revision procedure.

Figure 58B:
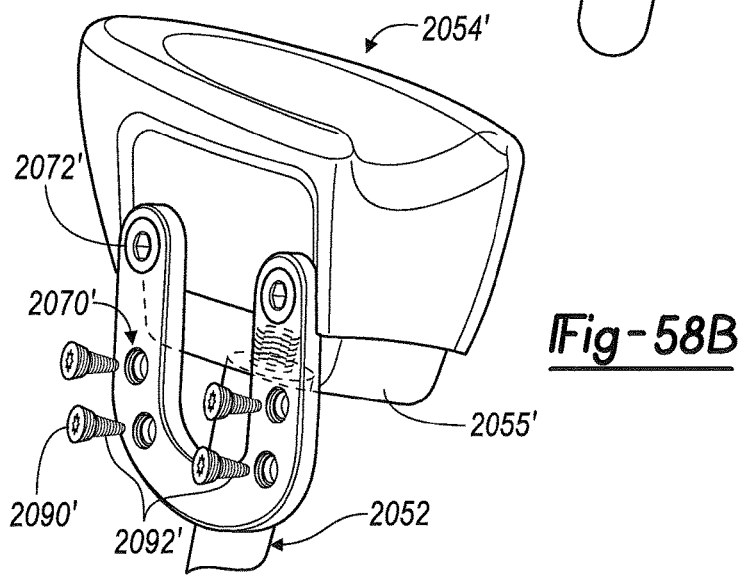
FIG. 58B is an assembled perspective view of a distal radial prosthesis according to various embodiments.

With reference to FIG. 58B, a prosthesis 2050' similar to the prosthesis 2050 is illustrated, thus substantially similar portions will be referenced with the same reference numerals augmented by a prime. The prosthesis 2050' can include a flange 2070' that is formed as a "U" or "V" or other generally open shape or configuration. The open configuration can be provided for various reasons. For example, the connection bores 2090' can be positioned a distance apart and/or away from a center line of the prosthesis 2050'. Thus, the bone connection members 2092' can easily pass the stem 2052' during implantation of the prosthesis 2050'.

In addition, the bone connection portals 2090, 2090' can be formed to allow the bone connection members to converge or diverge relative to the stem 2052. One skilled in the art will understand that the direction of the bone connection members as they pass through the flange 2070, 2070', 2006, 2008 can be selected to be any appropriate angle and can be selected for various reasons. One skilled in the art will also understand that the angle of passage can be selected according to various embodiments and any particular embodiment is merely exemplary.

Figure 59A:
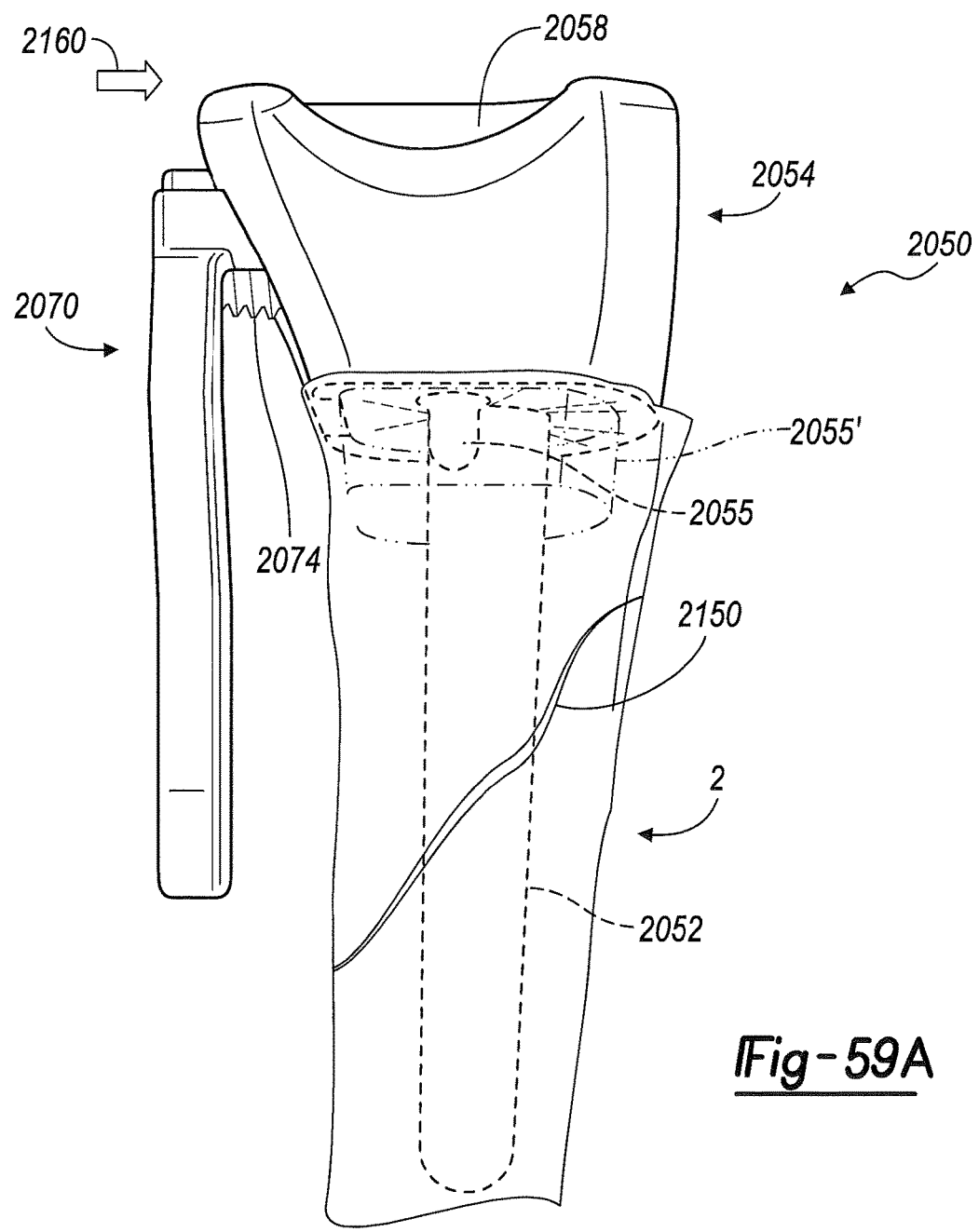
FIG. 59A is an environmental perspective view of a distal radial prosthesis according to various embodiments.
Figure 59B:
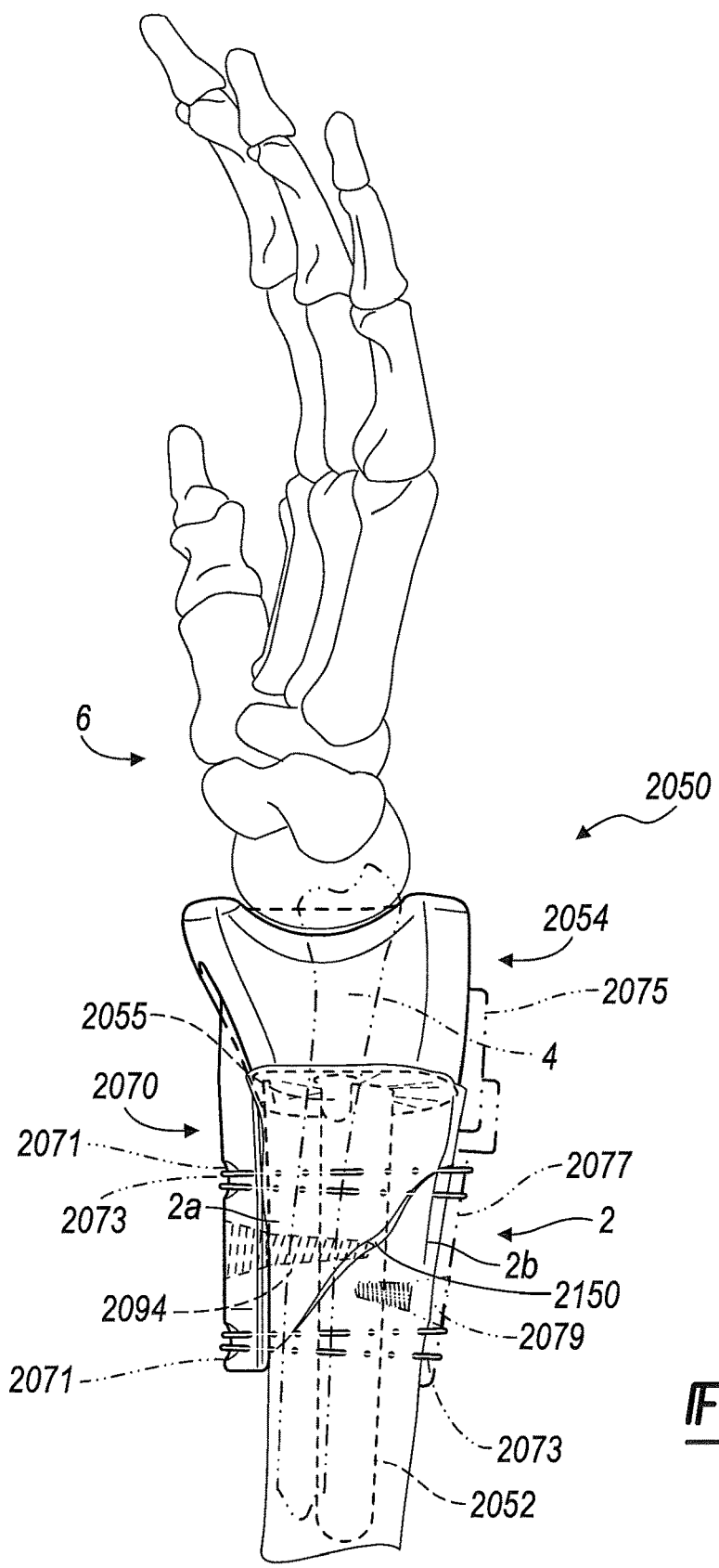
FIG. 59B is an environmental perspective view of a distal radial prosthesis according to various embodiments substantially implanted relative to a radius.

Turning reference to FIG. 59B, the prosthesis according to various embodiments, such as the modular prosthesis 2050 can include selected portions. The flange 2070, or a flange according to various embodiments, can include connection sections 2071, which can be depressions or hollows in the flange 2070. It will be understood that bores can also be formed in the flange 2070 to act as the connection sections 2071. The connection sections 2071 can be used to capture or engage connection portions 2073, such as cables. The connection portions 2073 can surround the bone 2 or other portions of the prosthesis 2050, such as a second flange 2077. The connection portions 2073 can compress selected portions for stability and healing or repair.

In addition, the second flange member 2077 can be provided as a part of the prosthesis 2050. The second flange member 2077 can interconnect with a third flange member 2075 according to any appropriate connection mechanism, including those discussed above. Further, a bone connection member 2079 can be provided to interconnect the second flange member 2077 with the bone 2. The second flange 2077 and the third flange 2075 can both be modular relative to the bone replacement portion 2054 or one or both the second flange 2077 and the third flange 2075 can be formed as a single member with the bone replacement member 2054, combinations thereof. Thus, one skilled in the art will understand that multiple flanges can be provided relative to the bone replacement member 2054 to provide support to different or plural areas of the bone 2 or other portions of an anatomy. For example, the flange 2070 and the second flange 2077 can be provided substantially opposed to one another so that they can compress the bone 2 between them.

An exemplary method of implanting the prosthesis 2050 is illustrated in FIGS. 59A and 59B. The radius 2 can be resected according to any appropriate method, including those described above and illustrated in FIGS. 52-54. The radius 2 can be prepared by resecting a selected portion of the radius 2, such as a distal portion thereof by the selected distance 1612. The resected distance 1612 can be replaced with the bone replacement portion 2054 of any appropriate height 2060. The stem 2052 can be implanted in the radius 2 and interconnected with the bone replacement portion 2054 in any appropriate manner, such as with the taper, a thread, a locking pin, a locking screw, or any other appropriate interconnection. Although a selected portion of the distal radius 2 can be resected, the distal radius 2 may also include a fracture 2150 that is not resected or replaced with the bone replacement portion 2054. The fracture 2150 can be stabilized, however, with use of the modular flange 2070 and the screws 2092 or other appropriate interconnection member.

The modular flange 2070 can be interconnected with the bone replacement portion 2054 using the connection member 2074. The bone replacement portion 2054 can include a threaded bore 2152 that includes an internal thread 2154 that can interconnect or engage the threads of the connection member 2074. As the connection member 2074 is driven, the modular flange 2070 can be moved in the direction of arrow 2160.

Once the attachment member 2074 has moved the flange 2070 relative to the radius 2, the interaction of the flange 2070 with the bone replacement portion 2054 and the stem 2052 can compress the radius 2 in an appropriate or selected manner. The compression of the flange 2070 against the radius 2 can assist in stabilizing the prosthesis 2050, compressing the fracture 2150, or be provided for any other appropriate reason. Further, the screws 2092 can be passed through the flange 2070 so that the shank 2094 can engage both a first side 2A and a second side 2B of the radius 2 and can span the fracture 2150. By spanning the fracture 2150, the fracture 2150 can be further compressed or stabilized. The compression of the fracture 2150 can assist in healing of the fracture, maintenance of the integrity of the radius 2, or any other appropriate reason. It will be understood that any appropriate number of screws 2092 or lengths of the screws 2092 can be provided with the distal radial prosthesis assembly 2050. Providing one screw is merely exemplary and provided for illustration purposes only.

Therefore, a modular flange, an integral flange, or a combination thereof can be provided for various purposes as illustrated in FIGS. 56 and 58. The flange can be a part of the prosthesis assembly that can be integral or formed as a single piece with another portion of the prosthesis assembly or be provided as a completely separate member. Further, it will be understood that the prosthesis assembly, such as the distal radial prosthesis 2000 and 2050 can be provided for both an initial or primary and a revision procedure. For example, the flange can be interconnected with a bone, such as the radius 2, at any appropriate time, such as during a second or revision procedure. Further, the various prosthesis assemblies can be used with modular flange portions to allow for installation of a flange member at a revision procedure. Thus, a completely one piece or modular system can be provided as selected.

Figure 60:
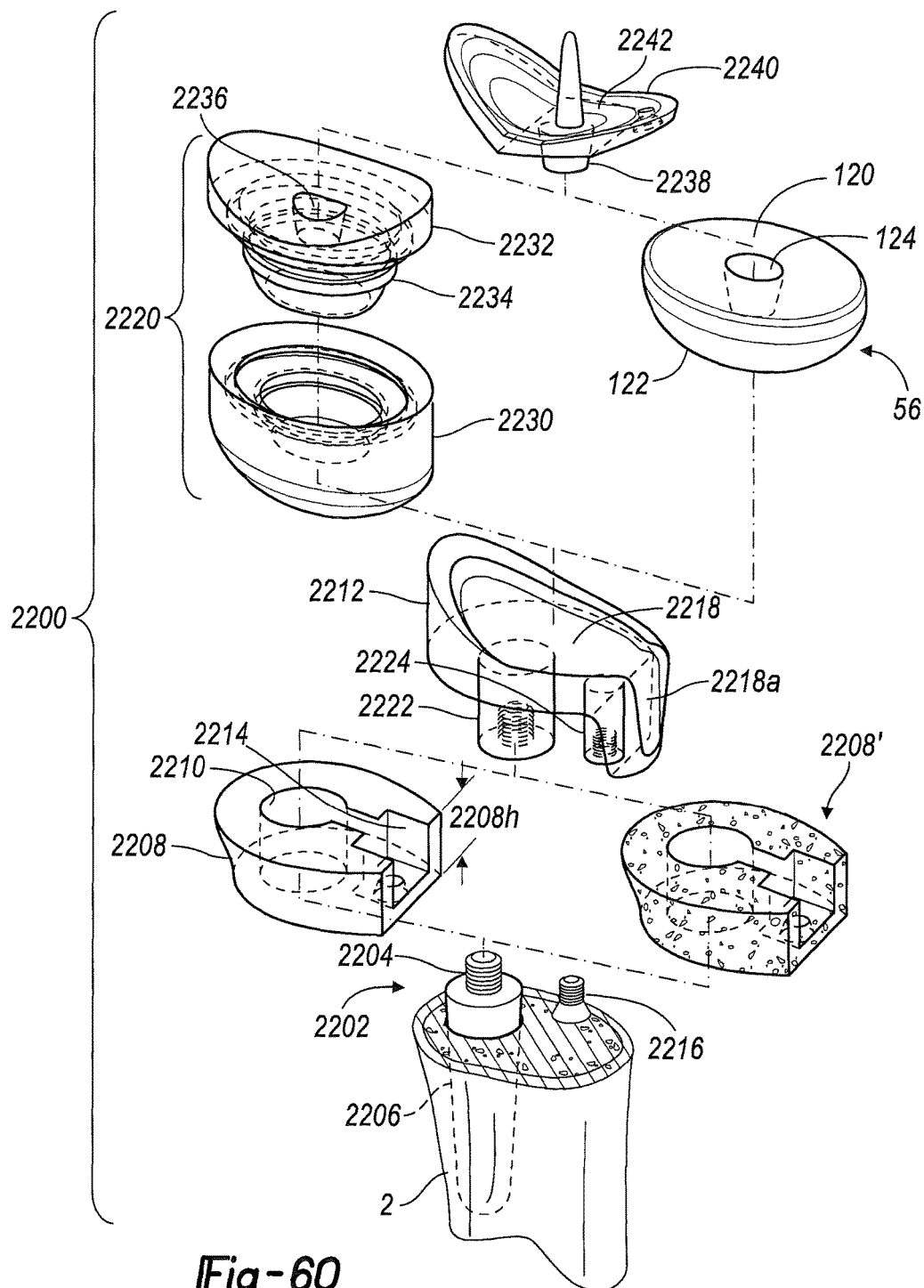
FIG. 60 is an exploded perspective view of a wrist prosthesis, according to various embodiments.

A total wrist prosthesis assembly 2200, illustrated in FIG. 60, can be used to replace various portions of the anatomy. For example, a distal portion of the radius 2 can be resected and all or part of the carpal bones can be replaced. The total wrist prosthesis 2200, therefore, can replace all or most of the carpal bones in the carpal complex or articulate relative to them. The total wrist prosthesis 2200, however, can include multiple portions, as discussed further herein, such as a stem 2202, bone replacement portion 2208, articulation portion 2212, carpal articulation portion 2220, and a bearing plate implant portion 2240.

As discussed above, the carpal implant can be affixed relative to selected portions of the carpal bones of a carpal complex after resecting and removing one or more of the bones in the carpal complex. The total wrist prosthesis 2200 can also be used for a total wrist prosthesis or in conversion of a hemi-wrist prosthesis to a complete wrist prosthesis. As discussed above, a hemi-wrist prosthesis can be used to replace a selected portion of the wrist, such as the distal radius or a portion of carpal complex, without replacing both sides of the articulating portion.

The various portions of the total wrist prosthesis 2200 can include the stem member 2202 that can be positioned in the radius 2. The stem member 2202 can include a connection portion 2204, which can be threaded to engage a matingly threaded portion 2222. The stem member 2202 can include a stem portion 2206 that extends into the radius 2. The stem portion 2206 can be provided in any appropriate configuration such as an I-Beam, cylindrical, or the like. Various configurations can assist in reducing rotation or reducing the possibility of rotation of the stem within the radius 2. Further, the stem can be formed from any appropriate material such as titanium, an alloy of cobalt chromium, an alloy of cobalt chromium and molybdenum, stainless steels, or any appropriate biologically compatible materials.

The body or bone replacement portion 2208 can be provided to be positioned at the distal end of the radius 2. The distal end or resected end of the radius 2 can be resected in any appropriate manner to engage or contact the body 2208. The body 2208 can include a passage or throughbore 2210 to allow for the connection portion 2204 of the stem 2202 to pass through and engage the articulation portion or member 2212. The body 2208 can also include a second passage or throughbore 2214 to allow for a connection portion or member 2216 to pass therethrough and also engage the articulating member 2212.

The articulation member 2212 can define an articulation or moving surface 2218. The articulation surface 2218 can be provided to articulate with a selected portion of the anatomy or the second prosthesis, such as the carpal prosthesis 2220. The articulation surface 2218 can also include a second or bone articulation surface 2218a. Extending proximally from the articulation member 2212 can be an engagement or connecting portion. A stem connection portion 2222 can include a mating thread to engage the threads 2204 of the stem. A second connection portion 2224 can also include mating threads to engage the screw 2216. The various connection portions can also be provided to mate with the body 2208 to allow for substantially tight tolerances once they are connected. Also the connection portions 2222 and 2224 can allow for a single keyed or unique connection and configuration of the articulation portion 2212, bone replacement portion 2208, and the stem member 2202. It will be understood that such keying is not required, but can be provided for various purposes (e.g. assembly efficiency and implant efficiency).

The radial portion of the total wrist prosthesis 2200 can generally include the stem 2202, the screw 2216, the body 2208, and the articulation member 2212. According to various embodiments, the body 2208 can be formed of a substantially solid and non-porous metal, a porous metal, a porous coated metal. As illustrated in FIG. 60, a body 2208', according to various embodiments, can be formed of or include a porous surface. The porous surface of the body 2208' can assist with fixation of the body 2208' to the anatomy, such as the radius 2. It will be understood that over time, after implantation of the body 2208', the distal end of the radius 2 can grow into the porous surface of the porous body 2208'. The porous portion of the body 2208' can include a porous coating; a porous metal portion (e.g. Regenerex™ Porous Titanium Construct sold by Biomet Manufacturing Corp.); porous metal portions disclosed in U.S. patent application Ser. No. 11/357,868, entitled "Method And Apparatus For Use Of Porous Implants" and in U.S. patent application Ser. No. 11/546,500, entitled "Method And Apparatus For Use Of Porous Implants", both of these are incorporated herein by reference; or other appropriate porous portions. The body 2208, 2208' can also be appropriately formed of U.H.M.W.P.E., ceramics, pyrolitic carbon, plastic, or polymers.

Further, the articulation member 2212 can also be formed of a metal or substantially hard material such as the same materials that form the body 2208. Therefore, the portions of the radial portion of the prosthesis 2200 can be formed substantially of a metal or other appropriate hard materials. Various metals can include titanium, stainless steels, alloys such as cobalt, chromium and molybdenum alloys, or any appropriate metals. The various metal portions can assist in a fracture treating prosthesis. It will be further understood, the radial portion of the prosthesis 2200 can be any appropriate prosthesis, such as those described above. Further, the various portions of the radial portion of the prosthesis 2200 can be assembled prior to implanting them into the radius 2.

Figure 61:
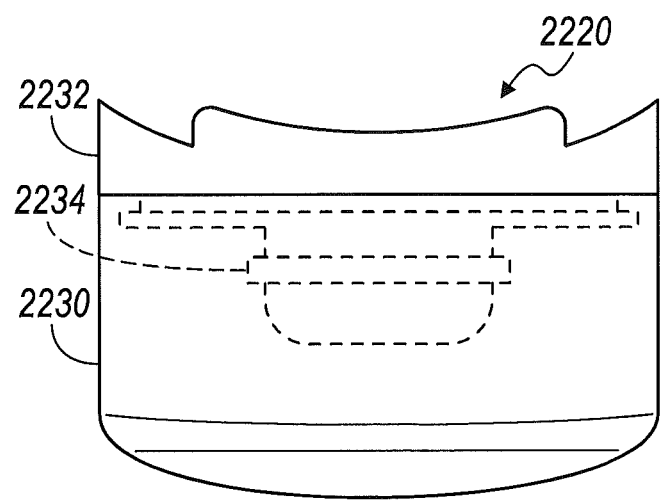
FIG. 61 is a plan view of a bearing component, according to various embodiments.

The prosthesis 2200 can also include the carpal complex prosthesis 2220. With continuing reference to FIG. 60 and additional reference to FIG. 61, the carpal complex prosthesis 2220 can be formed as a single unit from modular components. For example, an articulation or bearing portion 2230 can be molded onto or around an insert member 2232. The insert member 2232 can include one or more protrusions 2234 that can engage a portion of the bearing portion 2230 to hold it securely relative to the metal insert portion 2232.

The bearing portion 2230 can be formed of any appropriate material such as polyethylene, high molecular weight polyethylene, ceramics, for example, the materials that can be used to form the body 2208 or any appropriate material. Generally, the bearing portion 2230 can be formed of a material that can and is formed to articulate with the articulation surface 2218 of the articulation member 2212. As discussed above, the articulation member 2212 can be formed of a metal, thus the bearing portion 2230 can be formed of a polymer, plastic, ceramic, pyrocarbon (also referred to as pyrolytic carbon), or other appropriate material for articulating with the articulation member 2212 after implantation.

The metal insert 2232 can define an attachment or mating portion 2236 to mate with a complementary mating portion 2238 of a carpal implant member 2240. The carpal implant member 2240 can include a surface or portion 2242 that engages or is positioned next to one or more of the carpal bones in the carpal complex. The carpal prosthesis 2240 can be interconnected with the metal insert, such that the bearing member 2230 acts as a bearing portion for the carpal complex when articulating with the articulation member 2212 of the prosthesis 2200. Therefore, the radial portion of the prosthesis 2200 can be formed or include a metal material as the articulation portion 2212 and articulate with a polymer or similar material that forms the articulation bearing 2230.

It will be understood that the carpal bearing portion 2220 can be used with an appropriate prosthesis, including those discussed above. The carpal bearing portion 2220 can include the polymer or similar bearing member 2230 to articulate with a substantially hard, although smooth, articulation member. Further, it will be understood, that the carpal articulation or bearing portion 2220 can be used to assist in converting a hemi-prosthesis to a full prosthesis.

The attachment portion 2236 can be any appropriate attachment portion such as a mating locking taper, threaded, an adhesive, a receptacle or portion, or any appropriate connecting portion. Further, the body 2208 can be provided in a kit, including the kits discussed above, to provide or include a plurality of heights. A height 2208$h$ of the body 2208 can be selected based upon the amount of material to be resected from the radius 2. The portion of the radius 2 to be resected can depend upon the amount of fracture, disease, or the like of the radius 2 and, therefore, can be patient specific. Nevertheless, a kit can include a plurality of the bodies 2208 to allow for a substantially customized assembly and prosthesis during the procedure or intra-operatively.

As briefly described above, the various distal radial implant assemblies or members can be used in either a hemi-arthroplasty or a complete or total arthroplasty. For example, the distal radial implant assemblies 1500, 2000, 2050, etc. can be used to simply replace a distal portion of the radius 2. In this manner, a hemi-arthroplasty of the wrist can occur, which allows for maintenance of substantially the entire carpal complex. Alternatively, a substantial total wrist arthroplasty can be performed. In the total wrist arthroplasty, not only can a portion of the radius be replaced, but a portion of the carpal complex 6 can also be replaced with a selected implant or prosthesis. Therefore, it will be understood that any of the implants discussed above are not limited to either a total or a complete arthroplasty and can be provided in various combinations to allow for hemi-arthroplasty or a total arthroplasty. Further, the various implant portions can be selected to be altered during a revision procedure to allow for an alteration or changing of a hemi-arthroplasty to a total arthroplasty.

Alternatively, the carpal bearing portion 56 can also be provided to interconnect or replace a portion of the carpal complex. For example, the connection portion 2238 can be interconnected with the taper or connection portion 124. The connection portion 2238 can be utilized in either a complete or a hemi wrist arthroplasty. Also, if a radial implant is provided during a hemi-arthroplasty procedure and later a total wrist arthroplasty is selected, the bearing portion 2220 can be selected for implantation. In this manner the kit, such as the kit discussed above, can include both the bearing portion 56 and the bearing portion 2220, and any appropriate bearing member.

The various bearing portions 56, 2220 allow for selection intra-operatively or pre-operatively for performing a procedure. For example, providing both of the bearing components allows for the selection of a soft bearing or articulation surface or a hard articulation or bearing surface. Also, the selection can be made intra-operatively based upon various considerations, such as experience of a surgeon. Also, if a metal or hard radial implant is provided during a first or primary procedure, during a revision procedure (which can occur after the primary procedure is complete) the carpal portion 2220 can be provided to move against the hard radial component.

Figure 62:
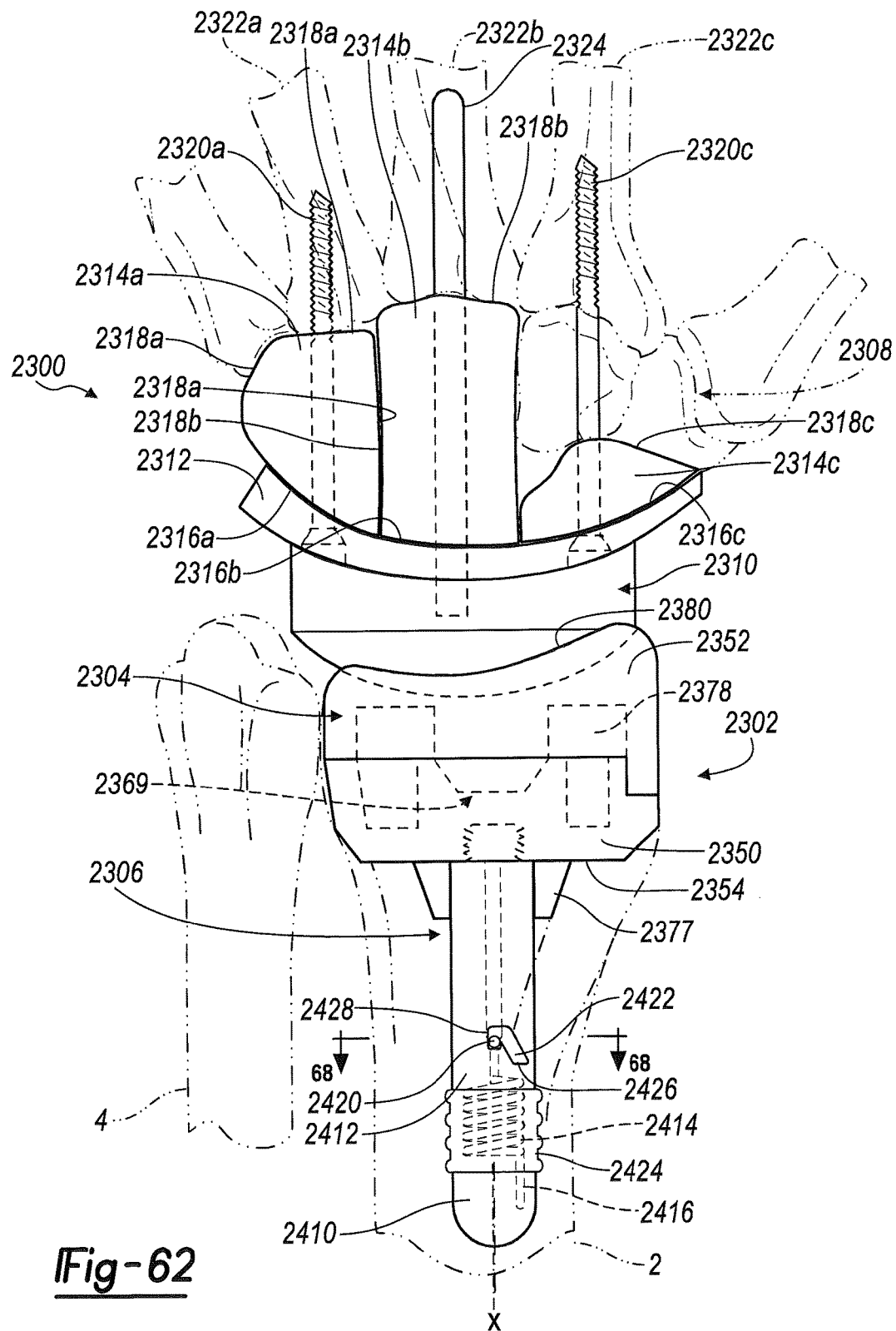
FIG. 62 is a view of the dorsal side of a patient's left hand and wrist illustrating a wrist prosthesis system, according to various embodiments.

Referring now to FIG. 62, an exemplary embodiment of a wrist prosthesis system 2300 is illustrated. As will be discussed, the system 2300 can replace at least a portion of various bones and other tissue within a patient's wrist including the forearm, the wrist joint, and/or the carpal complex as will be discussed in greater detail below. Furthermore, the system 2300 can be configured to replicate natural, anatomical motion of the patient's wrist.

Generally, the system 2300 can include a radial implant 2302 with a bone replacement member 2304 and a stem 2306. The system 2300 can also include a carpal implant 2308 that is operably coupled to the radial implant 2302. More specifically, the carpal implant 2308 can be pivotably coupled to the radial implant 2302 by a dome-shaped wrist bearing component 2310 in some embodiments. It will be appreciated by those of ordinary skill in the art that the components of the system 2300 can include similar features to any one of the embodiments discussed hereinabove, some of which are reiterated hereinbelow. The system 2300 can also have features discussed hereinbelow that are different from the embodiments discussed above.

As shown in FIG. 62, the carpal implant 2308 can include a base 2312. The base 2312 can be a curved plate and can be disposed on a proximal end of the hand similar to the carpal implant 54 shown in FIG. 2 or any other related embodiments described hereinabove.

The carpal implant 2308 can also include a plurality of separately attachable augments 2314a, 2314b, 2314c. The augments 2314a, 2314b, 2314c can be shaped according to one or more carpal bones within the carpal complex 6. As will be discussed, the augments 2314a, 2314b, 2314c each replace at least a portion of a carpal bone within the carpal complex 6. Also, as will be discussed, the augments 2314a, 2314b, 2314c are each removably coupled to the base 2312. As such, the carpal implant 2308 can be modular in nature and can be modified according to the patient's existing anatomy and the like. It will be appreciated that the carpal implant 2308 can include any number of augments without departing from the scope of the present disclosure. Moreover, while three augments 2314a, 2314b, 2314c are illustrated as attached to the base 2312, any number of augments can be separately attached.

More specifically, the augment 2314a can be a solid member and can include a mating face 2316a that abuttingly mates with the base 2312. The augment 2314a can also include a plurality of articulation surfaces 2318a on which adjacent members can articulate. For instance, the surrounding metacarpals can articulate on the articulation surfaces 2318a. Also, in some embodiments, the augment 2314b can articulate on the articulation surface 2318a of the augment 2314a. It will be appreciated, however, that the augment 2314a could be fused (i.e., fixed) to any surrounding members without departing from the scope of the present disclosure. The augment 2314a can also include various features for attaching anatomical tissue and the like. The augment 2314a can replace the lunate, hamate, and triquetrum bones 10, 12 (see FIG. 1) of the patient.

The augment 2314b can also include a mating face 2316b and a plurality of articulation surfaces 2318b. Because of the shape of the augment 2314b, the augment 2314b can replace the capitate bone 20 (see FIG. 1).

Likewise, the augment 2314c can include a mating face 2316c and a plurality of articulation surfaces 2318c. Because of the shape of the augment 2314c, the augment 2314c can replace the scaphoid bone 28 (see FIG. 1).

It will be appreciated that the augments 2314a-c can replace any suitable bone of the carpal complex 6. For instance, in some embodiments, the augments 2314a-c can replace one or more complete bones of the proximal row in the carpal complex 6 (i.e., the scaphoid 8, lunate 10, triquetrum 12, and/or pisiform 14 bones). In other embodiments, the augments 2314a-c can replace one or more complete bones of the distal row in the carpal complex 6 (i.e., the trapezium 16, trapezoid 18, capitate 20, and/or hamate 22 bones). In still other embodiments, the augments 2314a-c can replace complete bones in both the proximal and distal row in the carpal complex 6. The augments 2314a-c can also replace only a portion of a specific bone within the carpal complex 6.

The augments 2314a-c can be removably coupled to the base 2312 in any suitable fashion. For instance, in some embodiments, the carpal implant 2308 includes one or more fasteners 2320a, 2320c for this purpose. More specifically, the carpal implant 2308 can include a fastener 2320a, which extends through the base 2312 and the augment 2314a and also into the fourth metacarpal 2322a. Accordingly, the fastener 2320a can secure the augment 2314a between the base 2312 and the fourth metacarpal 2322a to secure the augment 2314a within the carpal complex 6. Likewise, the carpal implant 2308 can include a fastener 2320c, which extends through the base 2312 and the augment 2314c and also into the second metacarpal 2322c. Accordingly, the fastener 2320c can secure the augment 2314c between the base 2312 and the second metacarpal 2322c to secure the augment 2314c within the carpal complex 6. Furthermore, the carpal implant 2308 can include a stem 2324, which can extend from the base 2312, through the augment 2314b, and into the third metacarpal 2322b. Accordingly, the stem 2324 can secure the augment 2314b between the base 2312 and the third metacarpal 2322b to secure the augment 2314b within the carpal complex 6. It will be appreciated that the length, width, threading, and/or other features of the fasteners 2320a, 2320c and the stem 2324 can be adjusted based upon the patient's anatomy, based on any deterioration of the patient's anatomy, based upon the judgment of the surgeon, etc. for ensuring adequate fixation of the carpal implant 2308.

Figure 70:
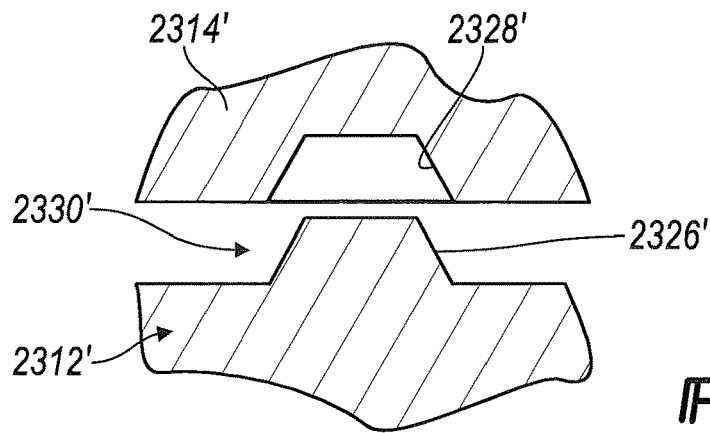
FIG. 70 is an exploded section view of a coupling for the wrist prosthesis system of FIG. 62.

It will be appreciated that the augments 2314a-c can be removably coupled to the base 2312 in any other suitable fashion in addition to or instead of the fasteners 2320a, 2320c and stem 2324. For instance, as shown in FIG. 70, the base 2312' can include a frusto-conical projection 2326', and the augment 2314' can include a frusto-conical recess 2328' that receives the projection 2326'. The projection 2326' and recess 2328' can each be correspondingly tapered such that the projection 2326' and recess 2328' comprise a taper lock coupling 2330' (i.e., Morse taper) for removably coupling the augment 2314' and the base 2312'.

Figure 71:
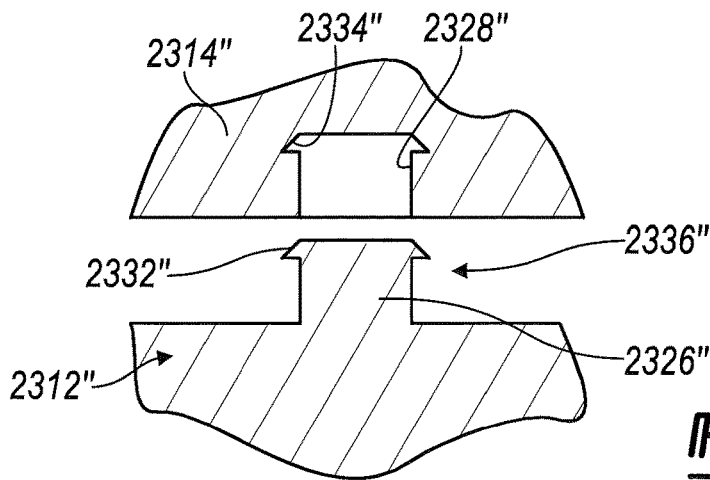
FIG. 71 is an exploded section view of another embodiment of a coupling for the wrist prosthesis system of FIG. 62.

Also, as shown in FIG. 71, the base 2312" can include a cylindrical projection 2326" with an enlarged rim 2332". The augment 2314" can also include a cylindrical recess 2328" that receives the projection 2326", and the recess 2328" can include a pocket 2334" that receives the enlarged rim 2332". Accordingly, the projection 2326" and recess 2328" comprise a dovetail coupling 2336" for removably coupling the augment 2314" and the base 2312".

Figure 72:
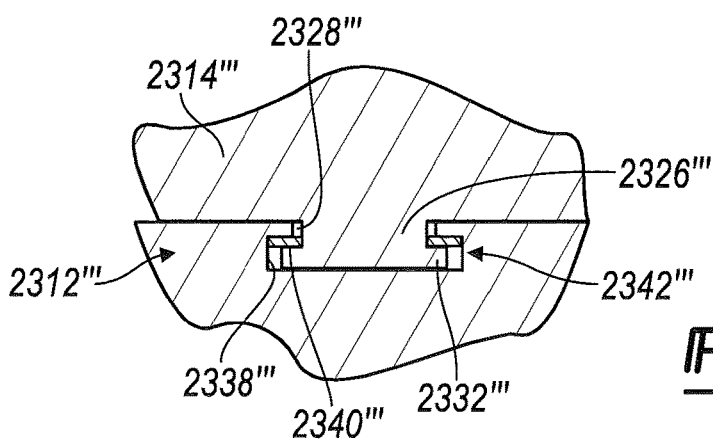
FIG. 72 is an assembled section view of another embodiment of a coupling for the wrist prosthesis system of FIG. 62.

Moreover, as shown in FIG. 72, the augment 2314''' can include a cylindrical projection 2326''' with an enlarged rim 2332m. The base 2312''' can also include a cylindrical recess 2328''' that receives the projection 2326''', and the recess 2328''' can include an undercut portion 2338''' that receives the rim 2332'''. A resilient ring 2340''' can also be included, and the ring 2340''' can surround the projection 2326''' and be disposed in the undercut portion 2338'''. The ring 2340''' can retain the projection 2326''' within the recess 2328'''. Accordingly, the projection 2326''', recess 2328''', and ring 2340''' can comprise a ring lock coupling 2342''' for removably coupling the augment 2314''' and the base 2312m.

Additionally, it will be appreciated that the individual augments 2314a-c can be interconnected together using fasteners, taper lock couplings 2326', dovetail couplings 2336", ring lock couplings 2342''', or any other suitable means without departing from the scope of the present disclosure. Furthermore, it will be appreciated that at least some of the augments 2314a-c can be integrally coupled to the base 2312 and/or the other augments 2314a-c can be removably coupled without departing from the scope of the present disclosure.

The augments 2314a-c and base 2312 can include and be manufactured from any suitable materials. For instance, the augments 2314a-c and the base 2312 can include and be manufactured from cobalt-chromium-molybdenum (Co- CrMo), polyetheretherketone (PEEK), including carbon fiber reinforced PEEK, titanium, stainless steel or other biocompatible material.

Thus, to use the carpal implant 2308 of the wrist prosthesis system 2300 shown in FIG. 62, the surgeon can select the augments 2314a-c for implantation within the patient. More specifically, the surgeon can determine (e.g., by X-ray or other imaging procedures) which bones of the patient's carpal complex 6 need to be replaced. Then, the surgeon can entirely remove those bones from the patient and use the selected augments 2314a-c to replace the removed bones.

Also, a modular kit can be provided having the same augments 2314a-c in a wide variety of sizes, materials, etc. As such, the surgeon can select the augments 2314a-c for implantation to closely match the patient's anatomy, to provide desired material properties, etc. Moreover, the surgeon can select a base 2312 for implantation in a similar fashion. For instance, a modular kit can include a wide variety of bases 2312 that vary in size, materials, etc. Once selected, the base 2312 and augments 2314a-c can be removably coupled as discussed above and implanted. It will be appreciated that the carpal implant 2308 advantageously allows the surgeon to vary the carpal implant 2308 in a number of ways so that the carpal implant 2308 can be tailored to a specific patient. Furthermore, the augments 2314a-c can completely replace a bone within the carpal complex 6, which can be very useful for patients with a high degree of bone degeneration, damage, etc.

Figure 63:
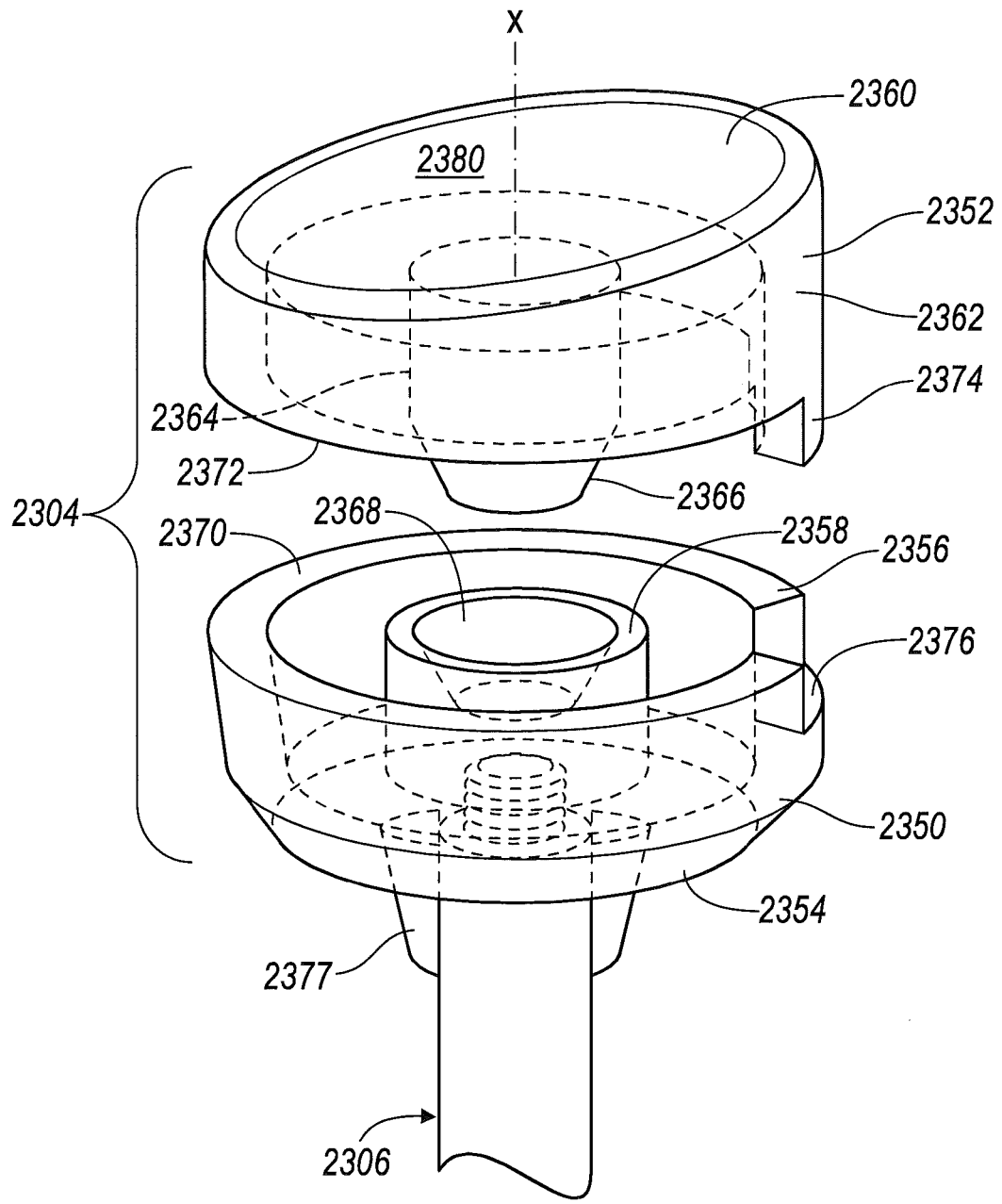
FIG. 63 is an exploded perspective view of a bone replacement member of the wrist prosthesis system of FIG. 62.

Referring now to FIGS. 62 and 63, the bone replacement member 2304 of the radial implant 2302 will now be discussed in greater detail. As shown in FIG. 62, the bone replacement member 2304 can be coupled to a resected, distal end of the radius 2 similar to the embodiments discussed hereinabove.

As shown in FIGS. 62 and 63, the bone replacement member 2304 has an axis X. The bone replacement member 2304 can include a proximal portion 2350 and a distal portion 2352 that is removably coupled to the proximal portion 2350. As shown in FIG. 63, the proximal portion 2350 can include a disc-shaped proximal end 2354, a hollow cylindrical outer wall 2356, and a cylindrical inner projection 2358. The distal portion 2352 can include a distal end 2360, a hollow cylindrical outer wall 2362, and a cylindrical inner projection 2364.

As shown in FIG. 63, the inner projection 2364 of the distal portion 2352 can include a tapered projection 2366. Also, the inner projection 2358 of the proximal portion 2350 can include a tapered recess 2368 that receives the projection 2366 when the proximal and distal portions 2350, 2352 are coupled. As shown in FIG. 62, the projection 2358 and the recess 2368 can be tapered so as to comprise a taper lock coupling 2369 (i.e., Morse taper); however, it will be appreciated that the distal and proximal portions 2352, 2350 can be coupled in any other suitable fashion, such as a dovetail coupling, fasteners, a ring lock coupling, and the like. Furthermore, when the proximal and distal portions 2350, 2352 are coupled, a rim 2370 of the outer wall 2356 can mate against a rim 2372 of the outer wall 2362. Additionally, the distal portion 2352 can include a projection 2374, which projects generally parallel to the axis X away from the rim 2372, and the proximal portion 2350 can include a recess 2376 in the rim 2370 that receives the projection 2374 to limit relative rotation of the proximal and distal portions 2350, 2352 about the axis X.

As shown in FIG. 63, the inner projections 2358, 2364 are spaced apart from the respective outer wall 2356, 2362. Thus, as shown in FIG. 62, the proximal and distal portions 2350, 2352 cooperate to define an annular pocket 2378 encapsulated within the bone replacement member 2304 when the proximal and distal portions 2350, 2352 are removably coupled. It will be appreciated that the pocket 2378 can have any suitable shape. It will also be appreciated that the proximal and distal portions 2350, 2352 can be coupled so as to hermetically seal the pocket 2378. It will also be appreciated that the system 2300 can include a separate sealing member (not shown) for hermetically sealing the pocket 2378.

Accordingly, because the bone replacement member 2304 includes the pocket 2378, the weight of the bone replacement member 2304 can be advantageously reduced. Furthermore, the proximal and distal portions 2350, 2352 can be made of different materials for further weight reduction. For instance, the proximal portion 2350 can be made of titanium while the distal portion 2352 can be made of CoCr.

Furthermore, the system 2300 can include a variety of modular proximal and distal portions 2350, 2352 having different sizes, materials, etc. Accordingly, the bone replacement member 2304 can be highly variable and tailored according to the particular patient. Also, in some embodiments, only one of the proximal and distal portions 2350, 2352 is modular and includes a wide variety of sizes, while the other comes in a single size.

As shown in FIGS. 62 and 63, the proximal end 2354 of the proximal portion 2350 can abut the resected end of the radius 2 of the patient. Also, the proximal end 2354 can include projections 2377 that project in a generally transverse direction away from the axis X. The projections 2377 can extend into the cortical region of the radius 2 for further securement of the bone replacement member 2304 to the radius 2.

Furthermore, as shown in FIG. 63, the distal end 2360 of the distal portion 2352 can include an articulation surface 2380. The bearing component 2310 can articulate on the articulation surface 2380. It will be appreciated that the bone replacement member 2304 can also include an ulna articulation section (not specifically shown) on which the ulna 4 can articulate. The ulna articulation section can be similar to the ulna articulation section 2010, 2058 of the embodiments shown in FIGS. 56-58B. In some embodiments, the bone replacement member 2304 can also include carpal articulation surfaces (not specifically shown) on which bones of the carpal complex 6 or on which the carpal implant 2308 can articulate.

Figure 64:
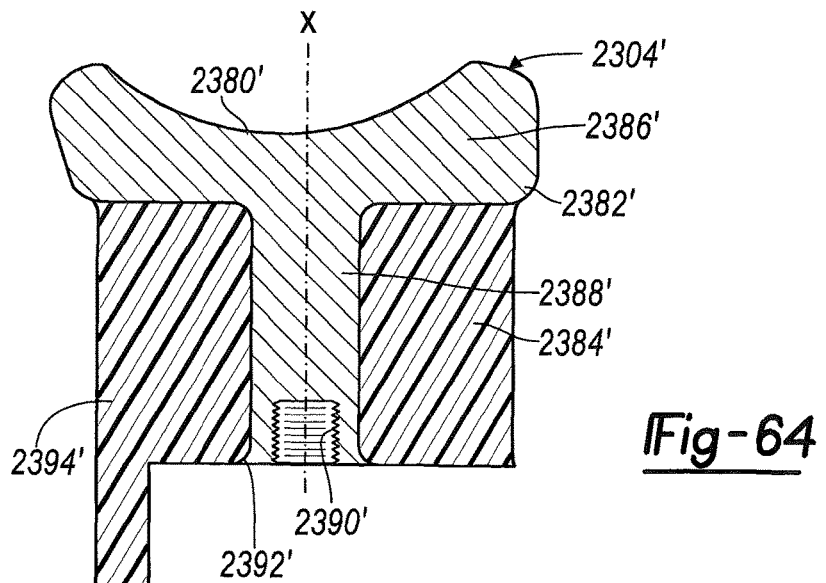
FIG. 64 is a section view of another embodiment of the bone replacement member of the wrist prosthesis system of FIG. 62.

Referring now to FIG. 64, an alternative embodiment of the bone replacement member 2304' will be discussed. As shown, the bone replacement member 2304' includes a first portion 2382' and a second portion 2384'. The first portion 2382' can include a head 2386', which is generally disk shaped. The head 2386' can include the articulation surface 2380'. The first portion 2382' can also include a stem 2388', which is elongate and extends from the head 2386' in a direction generally parallel with the axis X. The stem 2388' can include a threaded bore 2390', which can threadably receive the stem 2306 (FIG. 62). In addition, the stem 2388' can include an enlarged rim 2392' on an end of the stem 2388' opposite from the head 2386'. The rim 2392' extends in a direction generally transverse from the axis X.

Moreover, the second portion 2384' can include a generally cylindrical body 2394' having an axis generally parallel to the axis X and a flange 2396' that is elongate and that extends generally parallel to the axis X. The body 2394' can surround the stem 2388' of the first portion 2382'. The flange 2396' is spaced apart from the axis of the stem 2388'. The flange 2396' can be shaped generally similar to the flanges 2006, 2070, 2070' of the embodiments shown in FIGS. 56, 57, 58A, 58B, 59A, 59B. As such, when the bone replacement member 2304' is coupled to the radius 2, the flange 2396' can be disposed outside of the radius 2 and can inhibit rotation of the bone replacement member 2304' about the axis X.

The first portion 2382' and the second portion 2384' of the bone replacement member 2304' can be made of different materials. For instance, the first portion 2382' can be made out of a first material, such as a metallic material, and the second portion 2384' can be made out of a second material, such as a polymeric material. Further still, the first portion 2382' can be made out of CoCr, and the second portion 2384' can be made out of PEEK, including carbon fiber reinforced PEEK. However, it will be appreciated that the first and second portions 2382', 2384' can be made out of any suitable materials.

In some embodiments, the second portion 2384' can be molded to the first portion 2382' for coupling the first and second portions 2382', 2384'. However, the first and second portions 2382', 2384' can be coupled in any suitable fashion.

Figure 65:
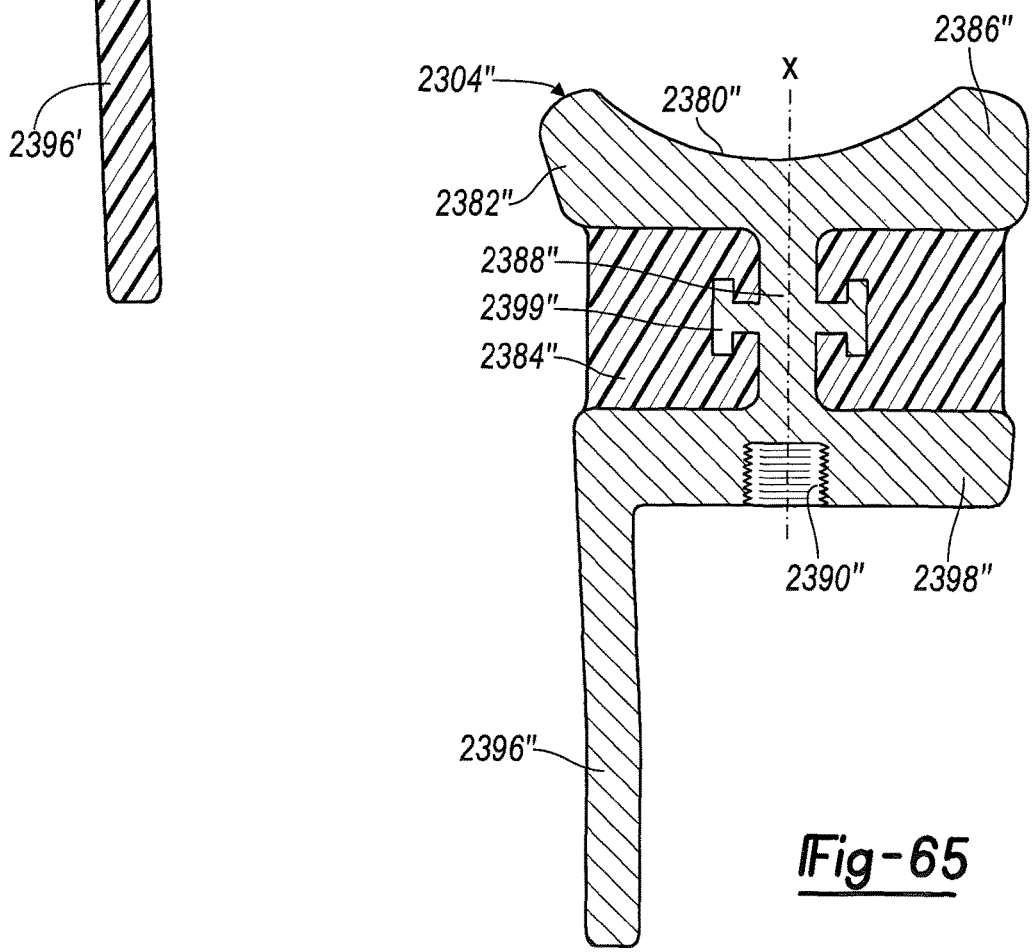
FIG. 65 is a section view of another embodiment of the bone replacement member of the wrist prosthesis system of FIG. 62.

Referring now to FIG. 65, another embodiment of the bone replacement member 2304" will be discussed. Similar to the embodiment of FIG. 64, the bone replacement member 2304" can include a first and second portion 2382", 2384". However, the first portion 2382" can include a head 2386", a stem 2388", as well as an integrally coupled base 2398". The threaded bore 2390" and the flange 2396" can be included on the base 2398". Also, the stem 2388" can include one or more projections 2399" that project transversely away from the axis X. In some embodiments, the projections 2399" have a T-shaped cross-section; however, the projections 2399" can have any suitable shape. The second portion 2384" can surround the stem 2388", and the projections 2399" can increase the surface area of the first portion 2382" to ensure secure bonding of the second portion 2384" to the first portion 2382".

Referring now to FIG. 66, another embodiment of the bone replacement member 2304'" will be discussed. The bone replacement member 2304'" is substantially similar to the embodiment of FIG. 65; however, as shown in FIG. 66 the base 2398'" can be removably coupled to the stem 2388'". For instance, the base 2398'" can include a recess 2402'" that receives the stem 2388'". In some embodiments, the base 2398'" and the stem 2388'" can be threadably attached. Moreover, in the embodiment of FIG. 66, the second portion 2384'" can be removably coupled to the stem 2388'". For instance, the second portion 2384'" can slide over the stem 2388'", and the base 2398'" can then be coupled to the stem 2388'". Accordingly, the second portion 2384'" can be retained on the bone replacement member 2304'" between the head 2382'" and the base 2398'". Furthermore, in some embodiments, the bone replacement member 2304'" can include a fastener 2400'", such as a lock washer, a locking nut, and the like, which further retains the second portion 2384'" on the stem 2388'". Additionally, as shown in FIG. 67, the longitudinal cross-section of the stem 2388'" can have a cross-sectional shape or an inhibiting mechanism that inhibits rotation of the second portion 2384'" about the axis X. For instance, the stem 2388'" can have a rectangular cross-section as shown in FIG. 67. However, the stem 2388'" can have any other suitable shape, such as a star, a cross, and the like to inhibit rotation of the second portion 2384'" about the axis X. In other embodiments, the stem 2388'" can be knurled (not shown) in order to inhibit rotation of the section portion 2384'" about the axis X.

It will be appreciated that the embodiments of the bone replacement member 2304', 2304", 2304'" shown in FIGS. 64-67 can have a reduced weight. This is because a significant portion of the bone replacement member 2304', 2304", 2304'" can be made out of a lightweight polymeric material, such as PEEK including carbon fiber reinforced PEEK. However, the bone replacement member 2304', 2304", 2304'" can still ensure proper articulation and attachment to surrounding members. Additionally, the bone replacement member 2304', 2304", 2304'" can resist excessive wear due to the materials therein. Also, the bone replacement member 2304', 2304", 2304'" can increase manufacturability because only a portion of the bone replacement member 2304', 2304", 2304'" need be machined while other portions can be molded.

Now, referring to FIGS. 62 and 63, the stem 2306 will be discussed in greater detail. As shown in FIG. 62, the stem 2306 can include a proximal portion 2410 and a distal portion 2412. As shown, the distal portion 2412 can be coupled to the bone replacement member 2304, 2304', 2304", 2304'" in any suitable fashion, such as by a threaded joint. The proximal portion 2410 can be fixedly coupled to the radius 2. As will be discussed, the proximal and distal portions 2410, 2412 of the stem 2306 can be movably coupled to each other to bias or pull the bone replacement member 2304 in a proximal direction.

For instance, the proximal and distal portions 2410, 2412 can each be generally elongate and at least partially hollow. The proximal and distal portions 2410, 2412 can be aligned with each other generally parallel to the axis X.

Furthermore, a biasing member 2414, such as a helical, compression spring, a compliant member, or any other suitable biasing member, can be housed within the stem 2306 and coupled between the proximal and distal portions 2410, 2412. For instance, a proximal end 2416 (FIG. 62) of the biasing member 2414 can be fixedly coupled to the interior of the proximal portion 2410. Also, as shown in FIG. 68, a distal end 2418 of the biasing member 2414 can be fixedly coupled to a rod 2420 that is disposed within the distal portion 2410, extending transverse to the axis X. The rod 2420 can received within a slot 2422 defined within the distal portion 2412 of the stem 2306.

In addition, the stem 2306 can include a seal member 2424 (FIG. 62), which extends between and seals any gap between the proximal and distal portions 2410, 2412 of the stem 2306 to limit intrusion of foreign matter within the interior of the stem 2306 through the slot 2422. It will be appreciated that the seal member 2424 can also cover and seal the slot 2422 from outside the stem 2306. The seal member 2424 can be resilient to maintain a seal despite relative movement between the proximal and distal portions 2410, 2412.

Thus, when implanting the stem, the proximal portion 2410 of the stem 2306 can be fixedly coupled to the radius 2 of the patient. The proximal portion 2410 can be fixed via bone cement, fasteners, and the like. Then, a tool (not shown), such as a screwdriver or other suitable tool, can extend along the axis X along the interior of the distal portion 2412 to operably couple to the rod 2420. By rotating the rod 2420 with the tool about the axis X, the rod 2420 can advance within the slot 2422, thereby changing the length and, thus, the spring force of the biasing member 2414. For instance, the slot 2422 can include a first end 2426, which is closer to the distal portion 2410, and a second end 2428 which is further away from the distal portion 2410. Thus, if the rod 2420 is disposed generally toward the first end 2426, the rod 2420 can be rotated about the axis X to move within the slot 2422 toward the second end 2428. By advancing the rod 2420, the rod 2420 lengthens the biasing member 2414 and increases the compressive force supplied thereby. Accordingly, the distal portion 2412 is biased and pulled in a proximal direction toward the proximal portion 2410 of the stem 2306. Accordingly, the stem 2306 can provide a biasing force, which biases the bone replacement member 2304 in a proximal direction to enhance fixation of the bone replacement member 2304 to the radius 2 of the patient and provide loading to the underlying bone.

Referring now to FIG. 69, another embodiment of the stem 2306' is shown. As shown, the distal portion 2412' of the stem 2306 includes an interior channel 2430' that extends generally parallel to the axis X. Also, the proximal portion 2410' includes a threaded bore 2432' that is generally aligned with the channel 2430'. Moreover, the stem 2306' includes a fastener 2434' that extends out of the channel 2430' and into the bore 2432'. The fastener 2434' can be of any suitable type, such as a threaded bolt or screw. Thus, to implant the stem 2306, the proximal portion 2410' of the stem 2306' can be fixedly coupled to the radius 2 of the patient. Then, a tool 2436' can be inserted within the channel 2430' and used to threadably advance the fastener 2434 within the bore 2432' to pull the distal portion 2412' and, thus, the bone replacement member 2304 proximately toward the proximal portion 2410' of the stem 2306. The fastener 2434' can have deformable threads, which deform as the fastener 2434' advances within the bore 2432' to thereby lock the fastener 2434' within the bore 2432'. Also, the distal portion 2412' can have a tapered projection 2438' which is received within a tapered recess 2440 of the proximal portion 2410' to reinforce the joint between the proximal and distal portions 2410', 2412'.

In addition, or alternative to various prosthesis implants discussed above, an ulna prosthesis 2600 can be implanted to replace a portion of the ulna 4. For example, the ulna prosthesis 2600 can be implanted to replace or repair a distal ulna portion 4a. In replacing the distal ulna portion 4a, the ulna prosthesis 2600 can articulate with portions of the carpal complex 6, the radius 2, and/or a prosthesis positioned to replace or repair portions of the carpal complex 6 or the radius 2. For example, a distal radial prosthesis 2602 can be implanted.

With reference to FIGS. 73-76, the distal ulnar prosthesis 2600 can be implanted onto a resected portion of the ulna 4. For example, a distal radial ulnar joint (DRUJ) 2601 can become injured or fractured due to use, injury, or the like. The DRUJ 2601 can be repaired or replaced by resecting the distal ulna 4a either alone, or in combination with, the distal radial portion 2a that articulates with the distal ulna 4a. The distal radial prosthesis 2602 can be implanted into the distal radius 2a to replace only the portion that articulates with the distal ulna 4a or can include a distal radial prosthesis, including those discussed above.

Regardless, the distal ulna prosthesis 2600 can include a distal radial articulating region or portion 2604 and a carpal complex articulating region 2606. The articulating regions 2604, 2606 can be provided in any appropriate shape or configuration for articulating with the distal radius 2a or the carpal complex 6. For example, the carpal complex articulating region 2606 can include peaks or valleys or bulbous portions to articulate with one or more of the carpal bones of the carpal complex 6.

With particular reference to FIG. 74, the distal radial prosthesis 2602 can be provided in any appropriate configuration. For example, the distal radius prosthesis 2602 can include an internal member or portion 2608 that can be formed of a hard or rigid material, such as a metal or metal alloy, over which a second material or bearing member 2610 is molded. The bearing material can include a polymer, such as an ultra high molecular weight polyethylene or other appropriate bearing materials. The inner member 2608 can include a peg or mounting portion 2612 that extends into a bore 2614 formed in the distal radius 2a. The mounting portion 2612 can include a threaded portion, a tapered portion, a bone ingrowth portion, or other appropriate bone fixation mechanism. An appropriate mounting portion 2612 can limit or resist rotation and maintain the position of the distal radial prosthesis 2602. The distal radial prosthesis 2602 can be inserted through an incision 2618 formed near the DRUJ 2601. The incision 2618 can be used to insert both the distal radial prosthesis 2602 and the distal ulna prosthesis 2600.

The distal ulna prosthesis 2600 can be inserted into the distal ulna to replace a resected or damaged portion of the distal ulna. According to various embodiments, the distal ulna prosthesis 2600 can include a stand or stage member 2630 onto which a bearing portion or bearing member 2632 can be positioned or mounted. The stage member 2630 can form a platform for the bearing member. The bearing member 2632 can define a distal radial articulating portion 2604 and a carpal articulating region 2606. The bearing portion 2632 can be formed entirely of a single material, such as polyetheretherketone (PEEK), pyrolytic carbon, polyethylene, ceramic, or other appropriate materials. The stand or stage member 2630 can be formed of appropriate complementary shaped portions of appropriate materials, such as a metal or metal alloys, including titanium, titanium alloys, cobalt chromium alloys, or other appropriate materials.

An ulna mounting region, such as a stem 2634, can extend from a base region 2636 for positioning within an intramedullary canal of the ulna 4. The stem 2634 can be any appropriate stem and can include a non-cylindrical or asymmetrical configuration, such as a T-shape or cruciform configuration. A non-symmetrical configuration can eliminate or reduce rotation of the distal ulnar prosthesis 2600 after implantation.

The stage member 2630 can include a high back or extending member 2638 that can extend from the base 2636 to substantially mimic a natural or anatomical configuration of the distal ulnar 4a. The back 2638 can have a planar surface 2638a that extends at an angle from a stage surface 2636a. The back 2638 and the planar surface 2638a can both be generally parallel with a longitudinal axis of the ulna 4. The stage surface 2636a can be generally perpendicular or at any appropriate angle to the planar surface 2638a. Thus, the stage member 2630 can be generally "L"-shaped in cross section, the back 2638 extending with the ulna 4 and the stage surface generally perpendicular to an axis of the of the ulna 4. The stage member 2630 can extend at any angle less than 180 degrees relative to the back 2638.

The back 2638 can also include soft tissue mounting regions. The soft tissue mounting regions can include a fin 2640. The fin 2640 can be solid or include bores 2642. The soft tissue mounting region can allow for reconnection or connection of soft tissue to the distal ulna prosthesis 2600 after the resection of the distal ulna 4a. The soft tissue, including the Triangular Fibrocartilage Complex, can be disconnected prior to or during the resection of the ulna 4 and retained for re-attachment. Soft tissue attachments to the distal ulna prosthesis 2600 can allow for a substantially natural articulation or operation of the wrist after the implantation of the distal ulna prosthesis 2600.

The bearing member 2632 can also include soft tissue connection regions or portions, such as throughbores 2644 and 2646. It will be understood that any appropriate number of soft tissue connection regions can be defined by the bearing member 2632. The soft tissue connection regions, defined either by the stage member 2630 or the bearing member 2632, can be provided for soft tissue attachment during an implantation procedure. Attachment of soft tissue can be selected by a user, such as a surgeon, and can be connected to any or all of the soft tissue connection portions. Accordingly, a procedure would not require attachment of soft tissue to all soft tissue connection portions. The soft tissue can be attached in any appropriate manner, such as with soft tissue attachment anchors, suture anchors, or passing sutures through the bores 2642-2646, or any other appropriate mechanism using the soft tissue connection regions 2642-2646.

The distal ulna prosthesis 2600 can be implanted, as discussed further herein, with a less invasive or minimally invasive procedure. The multiple portions or modular portions of the distal ulna prosthesis can allow the incision 2618 to be made smaller than the size of the assembled prosthesis 2600. The incision 2618 can be used to implant the portions of the distal ulna prosthesis sequentially, allowing each of the portions to be smaller than the total or whole distal ulnar prosthesis 2600. For example, the bearing member 2632 can be provided separate from the stand member 2630 in order to reduce the invasiveness of the procedure. In addition, each of the multiple components, the bearing member 2632 and the stand member 2630, can be provided individually, yet complementary, so that the surgeon can select from an inventory to create an appropriate configuration for a selected patient without requiring a plurality of complete prostheses. Thus, as discussed herein, each of the distal ulna prosthesis members can be provided in differing and distinct sizes, shapes, etc.

The stand member 2630 can also include a bearing mounting region or member 2650 of any appropriate configuration. The bearing mounting region 2650 can include a rail or T-shaped portion 2652 that extends from the plate or surface 2636a. The bearing mounting member 2650 can accept or cooperate with a stand or stage mounting region or member 2660 defined by the bearing member 2632. On the first side of the ulna bearing member 2632, a complete opening 2660a for the stage mounting region 2660 can be made. The opening 2660a can cooperate with a receiving end 2662 of the rail 2652. The bearing member 2632 can then be pushed over or slide over the bearing mounting member 2650 until an abutment end of the stage mounting region 2660 is engaged or contacted by the bearing mounting member 2650.

A second end 2632b of the bearing member 2632 does not include a complete opening for the stage mounting region 2660. The second end 2632b of the ulna bearing member 2632 can, however, include a passage or throughbore 2664 to receive a locking screw or member 2666. The locking member 2666 can pass through the throughbore 2664 in the ulna bearing member 2632 and engage a locking bore 2668 in the bearing mounting member 2650. It will be understood, however, that a locking member 2666 is not required in an inference fit or inference configuration, such as a bulbous or ratchet interaction can be provided between the bearing mounting member 2650 and the stage mounting region 2660.

Figure 76:
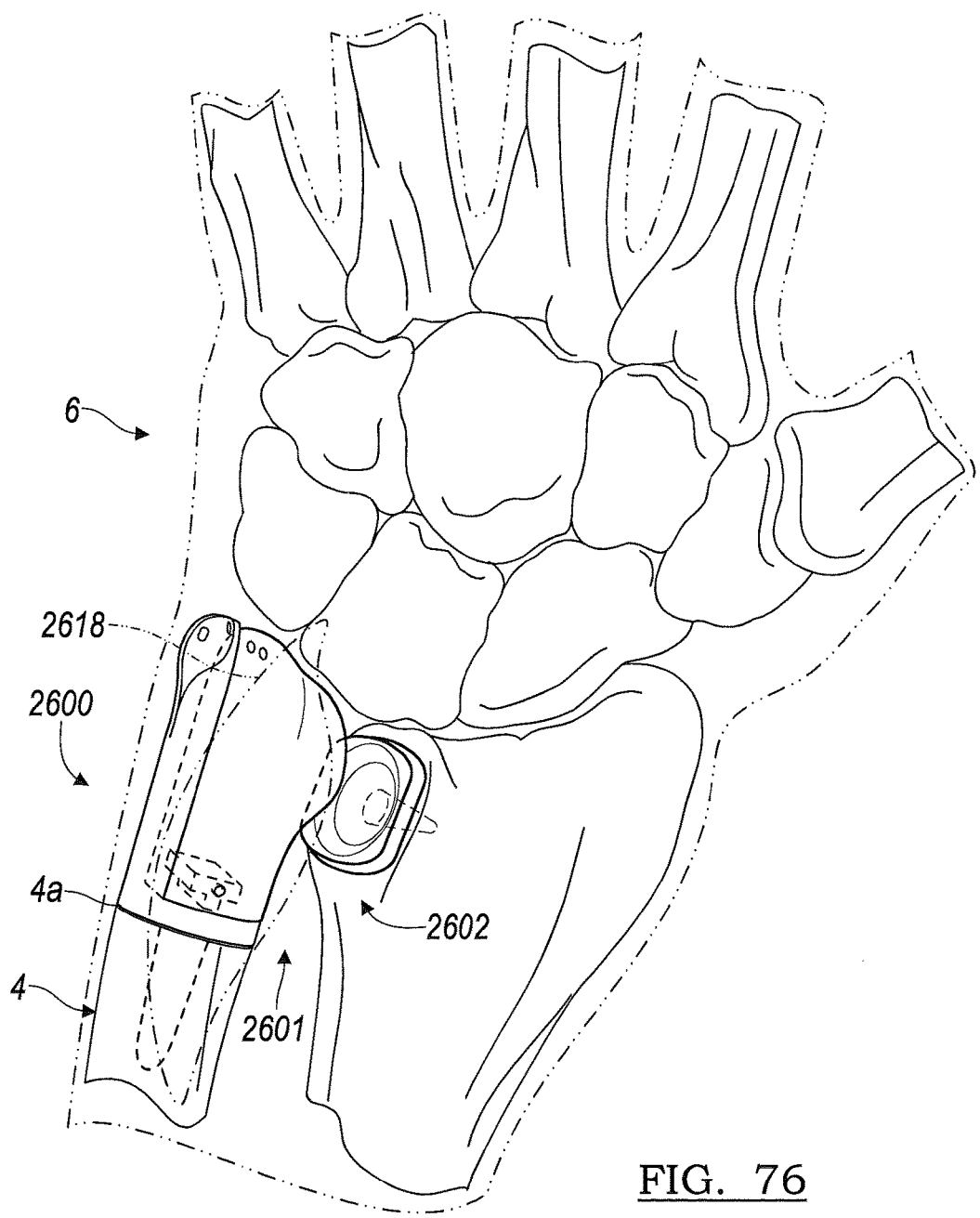
FIG. 76 is a perspective environmental view of a distal ulna and distal radial prosthesis.
Figure 77:
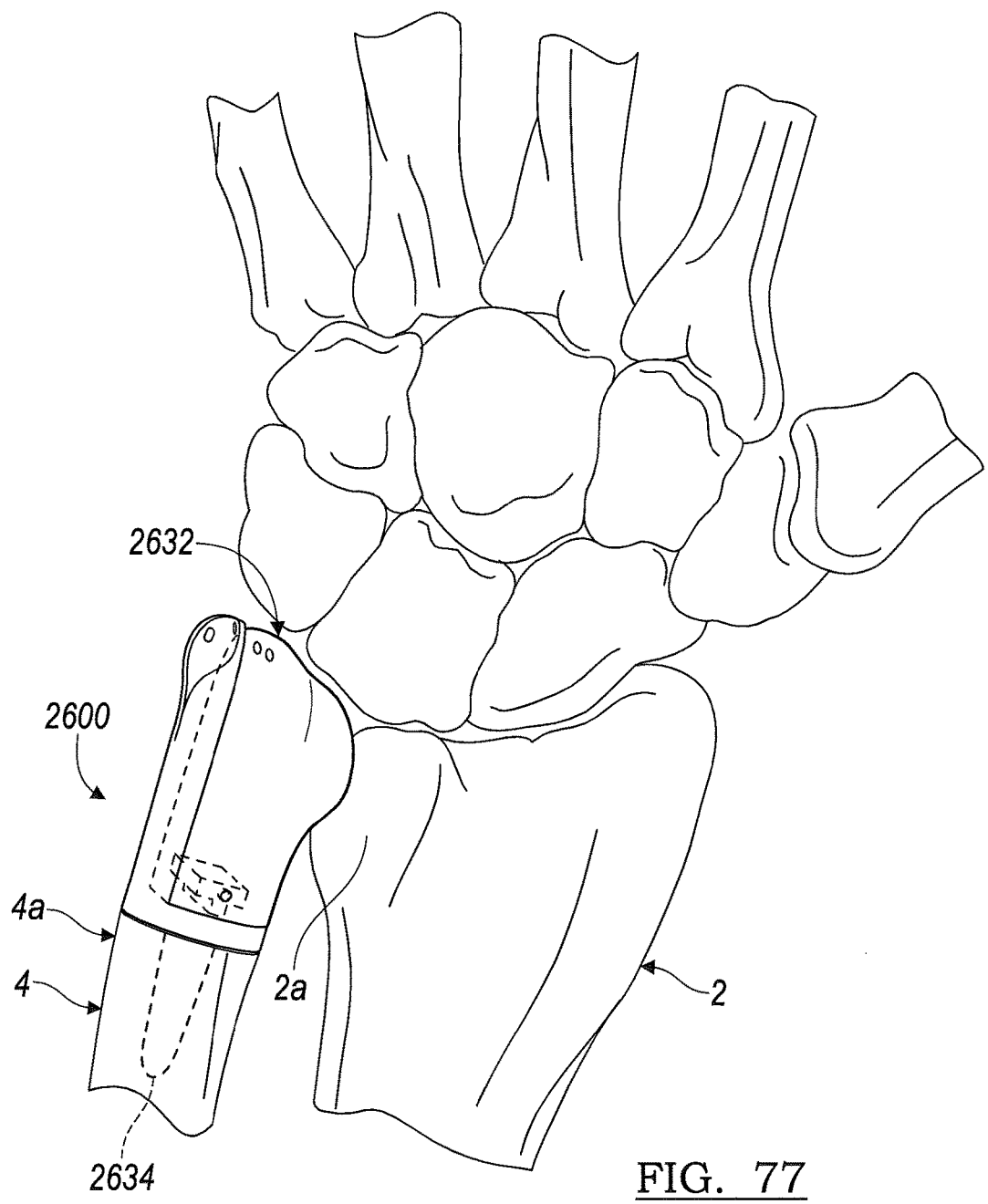
FIG. 77 is a perspective environmental view of a distal ulna and distal radial prosthesis.

With reference to FIG. 77, the distal ulna prosthesis 2600 can be implanted to articulate directly with the distal radius 2a. For example, bearing member 2632 can be formed of a material that can articulate with the distal radius 2a in an appropriate and anatomical manner. For example, various polymers, as discussed above, various metals, or pyrolytic carbon can be used to form the bearing member 2632, or at least an exterior surface of the bearing member 2632, to articulate directly with the distal radius 2a in an anatomical and natural manner. The distal ulna prosthesis 2600, however, can be substantially identical to the distal ulna prosthesis 2600 discussed in relation to FIGS. 73-76.

Figure 78A:
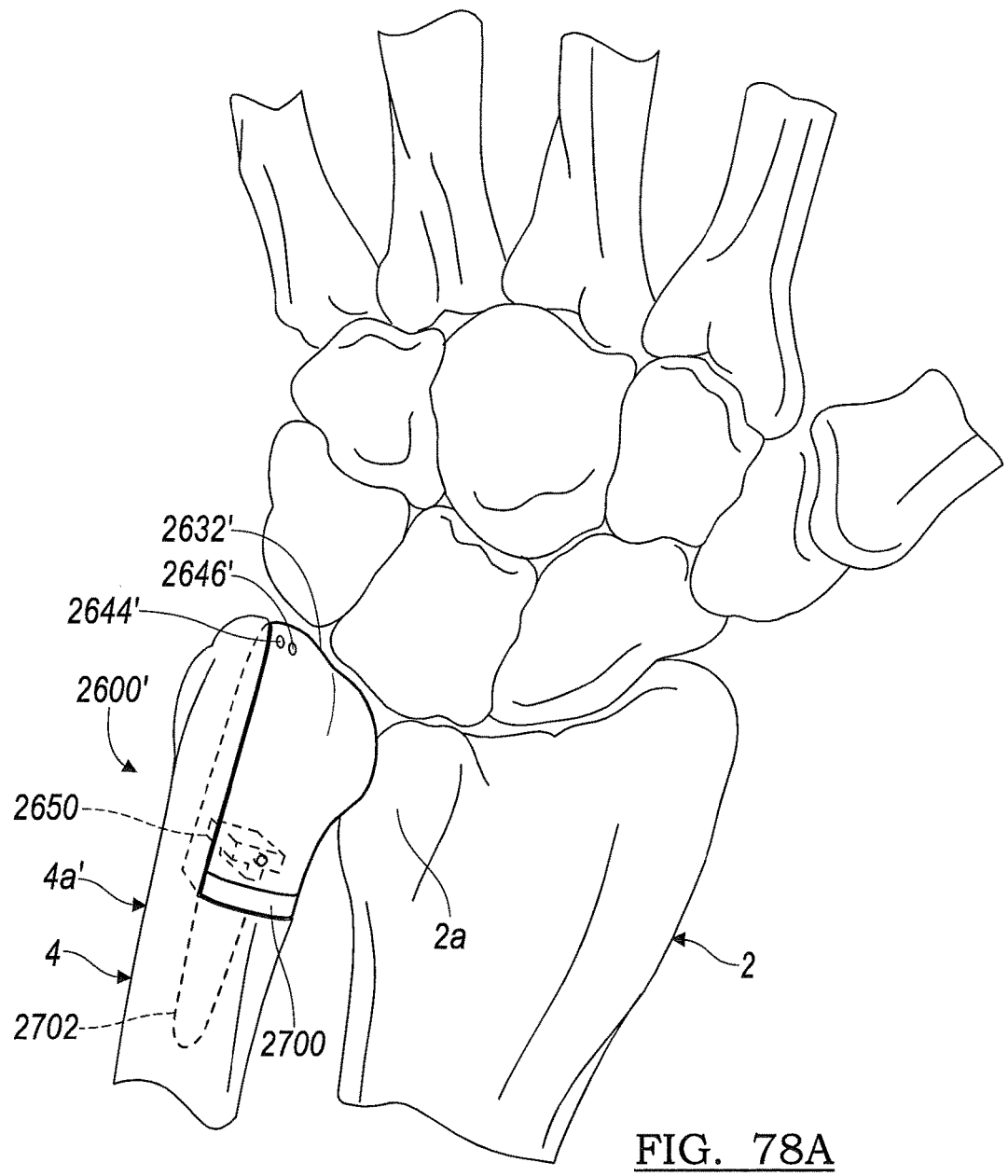
FIG. 78A is a perspective environmental view of a distal ulna and distal radial prosthesis.

With reference to FIGS. 78A and 78B, a distal ulna prosthesis 2600' is illustrated. The distal ulna prosthesis 2600' can be connected with the ulna 4 to replace only a selected portion, such as a medial portion of the distal ulna. Accordingly, a distal lateral ulna portion 4a' may be maintained in the patient. The distal ulna prosthesis 2600' can be provided to articulate with the natural distal radius 2a or with the distal radial implant 2602, discussed above. The distal ulna prosthesis 2600' does not include the high back portion 2638 extending from the stand portion 2636 in the distal ulna prosthesis 2600.

The distal ulna prosthesis 2600' can include a stand portion 2700 from which a stem 2702 can extend into the ulna 4. The stem 2702 can be an ulna mounting or connection portion and can be provided in any appropriate configuration, such as cruciform, asymmetrical, or any other appropriate configuration. As discussed above, the asymmetrical configuration, such as a cruciform configuration, can eliminate or reduce rotation of the distal ulna prosthesis 2600. The stem 2702 can also be modular or separable from the stand portion 2700, as discussed further herein. The modular stem can allow for customization by the user.

The stand portion 2700 can define the bearing attachment or mounting member 2650, which can be substantially identical to the bearing attachment member discussed in relation to the distal ulna prosthesis 2600. Thus, the bearing attachment member 2500 can include the T-shaped rail 2652 and the locking region 2668. The bearing member 2632 can then be connected to the stand portion 2700 in a sliding manner.

The distal ulna prosthesis 2600' can include a bearing member 2632', similar to the bearing member 2632 discussed above. The bearing member 2632', however, can engage or contact a distal and lateral portion of the ulna 4a' rather than the high back portion 2638 of the stand portion 2636. The bearing member 2632', therefore, can include the only soft tissue engagement portions 2644' and 2646' of the distal ulna prosthesis 2600'. The soft tissue engagement portions 2644', 2646' can be substantially identical to the soft tissue engagement portions 2644', 2646' discussed in relation to the bearing member 2632. Soft tissue engagement portions 2644', 2646' can include throughbores defined through the bearing member 2632' for attachment of soft tissue. It can be understood, however, the retention of the lateral distal ulna 4a', can reduce the amount or the number of soft tissue attachment portions needed or selected during a procedure to maintain a natural or selected soft tissue connection with the ulna 4.

The distal bearing 2632' can also include a stage mounting region 2660', substantially similar to or identical to the stage mounting region 2660 discussed above. Similarly, a locking bore or pass bore 2654' can be defined through the bearing member 2632'. Interconnection of the bearing member 2632' to the stand 2700, however, can be substantially identical or similar to that discussed above.

With reference to FIGS. 79A and 78B, the distal ulna prosthesis 2600, 2600' can include a bearing member or portion 2632". The bearing member 2632" can include a compound or two-part member. The bearing member 2632" can include an exterior or first articulating portion 2750 that includes a surface 2752 to articulate with the distal radius 2a or a distal radial implant 2602. The first articulating portion 2750 can be formed of any appropriate materials, including those discussed above such as polyethylene, poly-ethyl-ethyl-ketone (PEEK), pyrolytic carbon, or other appropriate materials. These materials can be provided and used in articulation with the distal radial implant 2602 or with the distal radius 2a.

The compound bearing portion 2632" can include the first portion 2750 molded over or fit over a second portion or member 2760. The second portion 2760 can include a connection region or portion 2762, such as a rib or raised member 2762. The connection region 2762 can allow for connection of the first portion 2750 to the second portion 2760. The second portion 2760 can be formed to connect strongly and securely with the bearing mounting member 2650.

The second portion 2760 can define a stage mounting region 2660", including those discussed above such as a reverse or female T-shape recess. The stage mounting region 2660 can be formed in the material of the second portion 2760. The material of the second portion 2760 can include metal or metal alloys, such as titanium, titanium alloys, cobalt chromium alloys, or any other appropriate alloys. The material of the second portion 2760 can be stiffer or harder than the material of the first portion 2750. Thus, the second portion 2760 can endure greater stresses in use. Therefore, the bearing member 2632" can be formed of two materials to enhance or achieve appropriate results. The distal ulna prosthesis 2600, 2600' can be provided in any appropriate configuration, including configurations for direct articulation with the distal radius 2a or the distal radial implant 2602, and configurations that include a single portion distal ulna bearing member or compound distal ulnar bearing member 2632".

The distal ulna prosthesis 2600, 2600' including an appropriate bearing member 2632, 2632', 2632" with or without the distal radius prosthesis 2602 can be implanted into the wrist of a patient according to the method discussed herein. For the discussion herein, the prosthesis 2600 and the distal radial implant 2602 will be discussed. A method of implanting the distal ulna prosthesis 2600 and the distal radial prosthesis 2602 will be discussed in relation to FIGS. 73-76 and 81.

Figure 81:
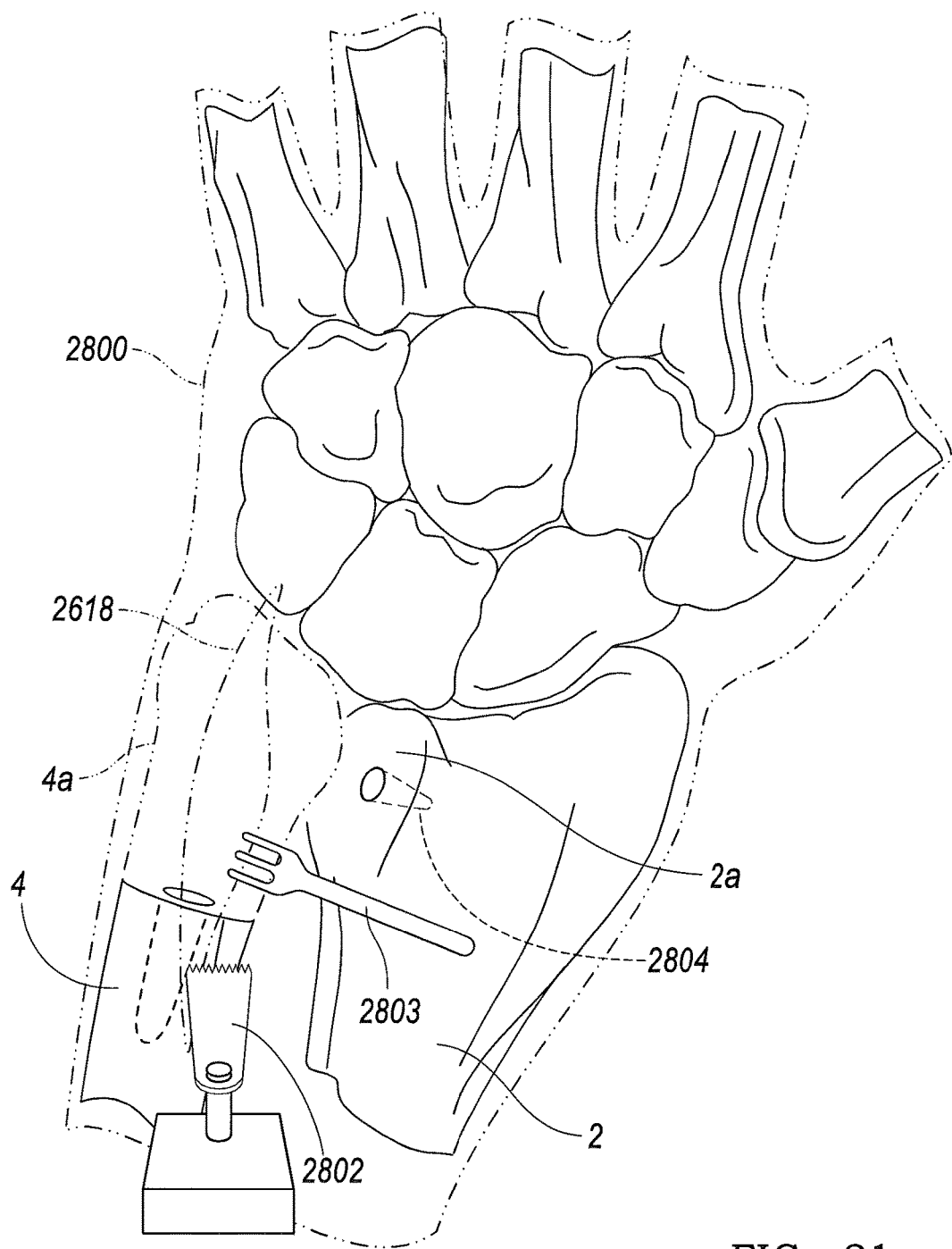
FIG. 81 is an environmental view of a procedure to implant a distal ulna prosthesis.

With reference to FIG. 81, the radius 2 can be positioned relative to the ulnar 4 in a position in preparation for a procedure. For example, as illustrated in FIG. 81, the left hand of the patient can be positioned posterior side up (palm down) prior to performing a procedure. The incision 2618 can be formed in the soft tissue, such as the dermis 2800 of the patient. Once the incision 2618 is formed over the distal ulna 4a, a resection tool, such as a reciprocating saw 2802 can be used to cut or resect the distal ulna 4a. A reaming tool can be used to ream the intramedullary canal of the ulna 4 and a drill can be used to form a distal radius receiving bore 2804. It will be understood that the distal radius 2a can also be completely resected for receiving a distal radial prosthesis. Also, a portion of the carpal complex can be resected.

Figure 73:
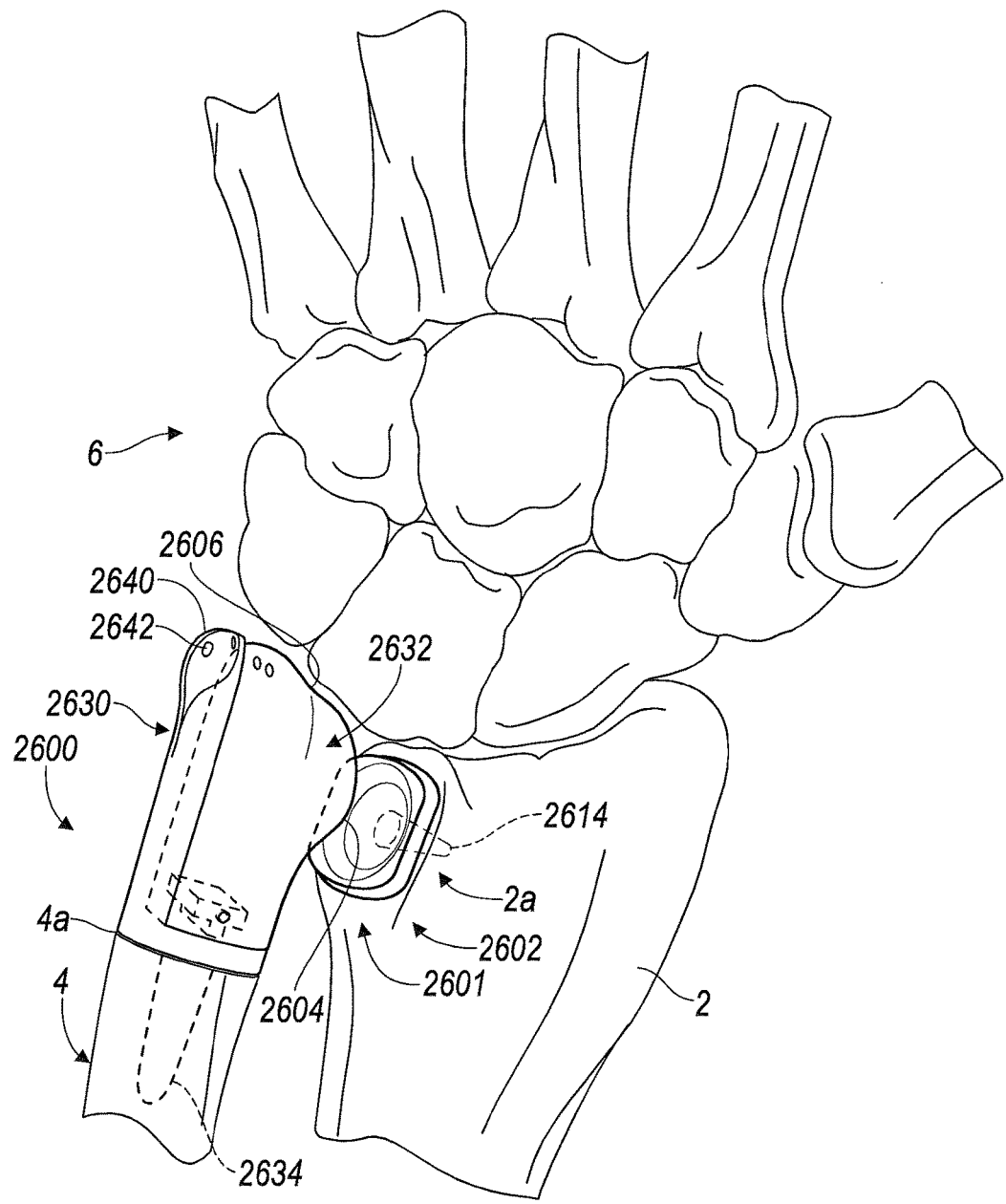
FIG. 73 is a perspective environmental view of a distal ulna and distal radial prosthesis.

After the resections, the distal radial implant 2602 can be positioned relative to the distal radius 2a, as illustrated in FIGS. 73 and 76. The stand member 2630 can then be positioned into the ulna 4 by moving the stem 2634 into the prepared intramedullary canal of the ulna 4. The stand member 2630 can be passed through the incision 2618 that was also used to pass the distal radial implant 2602. Once the stand 2630 is positioned within the ulna 4, the bearing member 2632 can be interconnected with the bearing mounting member 2650 of the stand member 2630. The bearing member 2632 can be passed through the incision 2618 and slid over the bearing connection or mounting member 2650, as illustrated in FIG. 74. By sliding the bearing member 2632 over the bearing mounting member 2650 the interconnection of the bearing member 2632 with the stand member 2630 can be efficient and quick for the surgeon to reduce time of the procedure.

Once the bearing member 2632 is positioned over or onto the stand member 2630, the locking member 2666 can be passed through the throughbore 2664 in the bearing member 2632 to engage the receiving bore 2668. As discussed above, an interference fit may be used in conjunction with or in substitution for the locking member 2666. In this manner, any of the distal ulna prostheses 2600, 2600', can be interconnected with the distal ulna or with the ulna 4.

Soft tissue can further be attached to the selected connection regions of the distal ulna prosthesis 2600. Soft tissue portions can include the Triangular Fibrocartilage Complex that naturally connected to the lateral portion of the distal ulna 4a. The soft tissue portions can be removed prior to or after resection and retained for connection to the prosthesis 2600. The soft tissue can then be connected to sutures, suture anchors, or other appropriate members for connection to the soft tissue connection regions 2642-2646. The connection of the soft tissue can maintain or repair the wrist to a natural configuration.

Figure 80:
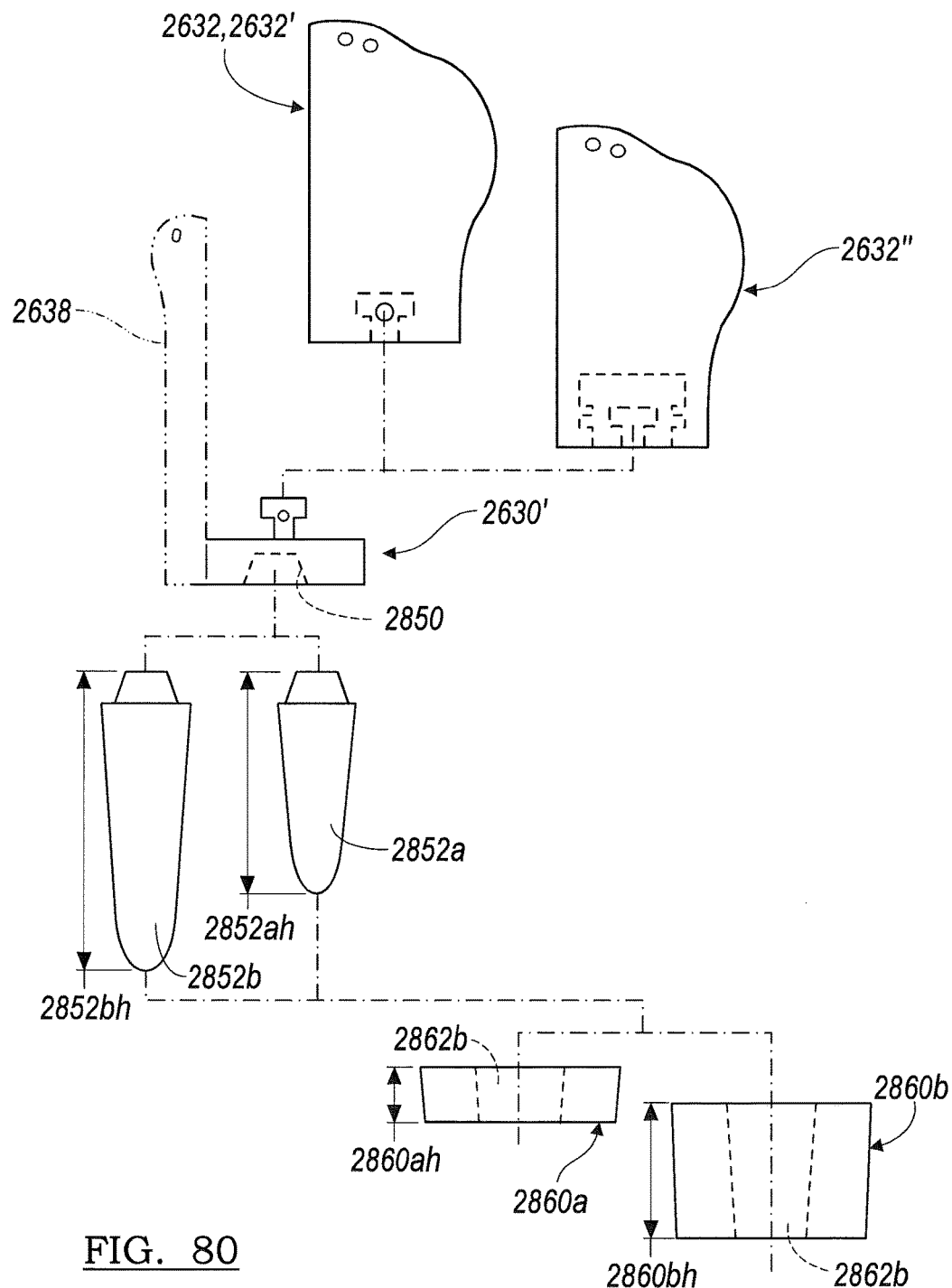
FIG. 80 is a kit view of a of a distal ulna prosthesis.

It will be further understood that the various members or portions of the ulna prostheses 2600, 2600' can be modular. As illustrated in FIG. 80, the stand portion 2630' can include a stem connection region 2850, such as a female taper. One or a plurality of stem members 2852a and 2852b can include male tapers to connect with the stem connection region 2850. Each of the stems 2852a and 2852b can include different heights 2852ah and 2852bh. The alternative heights can be used to interconnect with the ulna 4 in an appropriate manner. A user, such as the surgeon, can select the stem height for connection with the ulna 4 for a selected procedure. Additionally, bone replacement members adapters 2860a and 2860b of differing heights 2860ah and 2860bh can be positioned over the respective stems 2852a and 2852b for replacing a portion of the distal ulna 4a that is resected. Accordingly, the stand portion 2630' can be provided as a single thickness and the bone replacement members or adapters 2860a, 2860b can be provided in a kit or stock area for interconnection with the stand member 2630' for selection by a surgeon based upon an amount of resection. Each of the bone replacement members can include passages 2862a, 2862b that are provided to fit over the respective stems 2852a, 2852b for assembly during an implantation procedure. The bone replacement members 2860a and 2860b can be connected prior to positioning the stand member 2630' into the patient.

Further, the bearing members 2632, 2632', 2632" can be selected to interconnect with the stand member 2630'. The bearing members 2632, 2632', 2632" can be provided in a plurality of bearing heights and bearing widths for selection of an appropriate bearing member for a procedure. Accordingly, as illustrated in FIG. 80, the surgeon can select from a plurality of bearing members during a procedure. Thus, a kit or selection of ulna prosthesis members can be provided to be interconnected into one of a plurality of configurations. Thus, the surgeon can be provided with a plurality of options based on a small number of implant portions or members to fit a wide range of patients.

Figure 82:
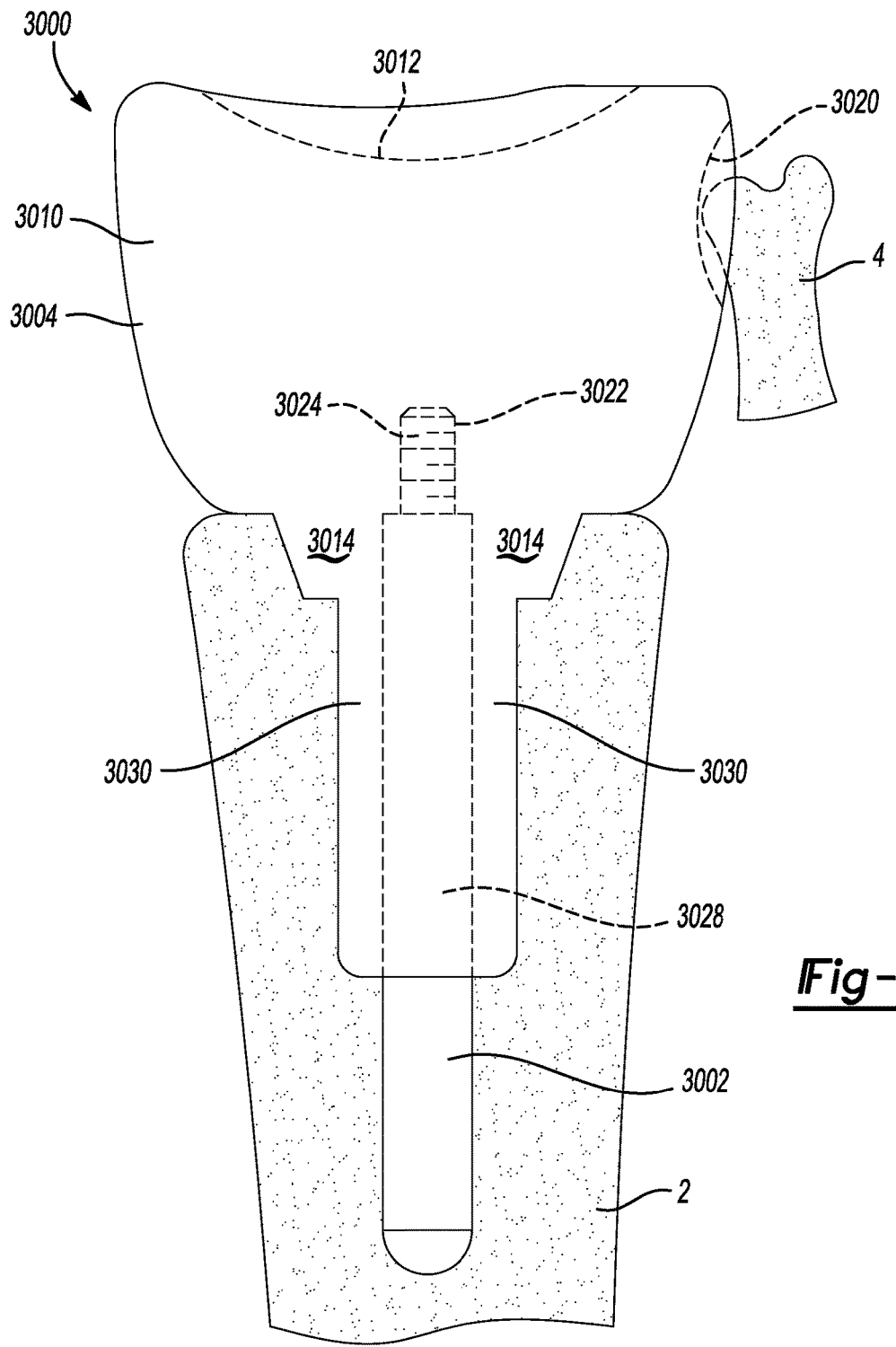
FIG. 82 is an anterior view of an exemplary distal radial implant constructed in accordance to additional features of the present teachings.

With reference to FIG. 82, a distal radial implant 3000 is illustrated according to various embodiments. The distal radial implant 3000 may be provided as a substantially modular implant that includes a stem portion 3002 that is operable to be positioned relative to a selected portion of the radius 2, such as the intramedullary canal. Affixed or interconnected with a selected portion of the stem portion 3002 is a distal radial component 3004. The distal radial component 3004 may be provided to engage the stem portion 3002 to provide a selected orientation, configuration, size and other considerations for the distal radial implant 3000. A carpal implant or portions of the carpal complex 6 (see FIG. 53) may articulate directly with the distal radial component 3004. Nevertheless, the modular distal radial component 3004 may be provided in a manner allowing a user, such as a physician, to select a distal radial implant intraoperatively to substantially match the anatomy of a patient.

The distal radial component 3004 can generally include a body portion 3010 having a superior or articulating portion 3012. The body portion 3010 may be formed in any appropriate manner to engage a selected portion of the anatomy. The body portion 3010 can have anti-rotation projections or teeth 3014 extending from a proximal surface. In another example, the teeth 3014 can be formed as part of the stem portion 3002. The teeth 3014 can engage the host radius 2 to inhibit rotation of the distal radial implant 3000 about a longitudinal axis of the stem portion 3002. The body portion 3010 may include various dimensions for accommodating a specific patient as described herein. In this way, a plurality of distal radial components 3004, each including a unique set of dimensions may be provided. Each may be provided in a large inventory or in a kit similar to the kit 1600 (FIG. 44) for selection by a user substantially intraoperatively or preoperatively. Nonetheless, various sizes or configurations of the distal radial components 3004 may be provided to allow for a substantially customized fit with a selected patient. For example, distal radial components having different heights may be provided for various degrees of bone loss.

The body portion 3010 of the distal radial component 3004 may also include the articulating portion 3012 that may also have a plurality of selected dimensions. For example, the articulating portion 3012 may include a length (medial/lateral direction) and a width (anterior/posterior direction). The articulating portion 3012 may also include an articulation depth that may vary depending upon a selected application. The articulation depth may generally be understood to be the deepest portion of the concave region that defines the articulating surface of the articulating portion 3012. Again, the articulating portion 3012 can have various dimensions that may be unique for a plurality of distal radial components 3004. In some examples, the concave region of the articulation portion 3012 can extend deeper into the body portion 3018 to nestingly receive at least portions of the carpal complex. Therefore, the user may select the distal radial component 3004 according to selected requirements or dimensions of a patient. An ulnar articulating region or sigmoid notch 3020 (shown configured for a right wrist in FIG. 82) can also be formed in the distal radial component 3004 for receiving a portion of an ulna 4.

Defined in the body portion 3010 is a female receiving or interconnection portion or depression 3022. The female interconnection 3022 may include a dimension that allows for substantial interconnection with a male interconnection 3024 of the stem portion 3002. In other configurations, the reception or interconnection portion 3022 may include a deformable member (such as a canted coil spring or screw or other mechanism), which may engage a depression formed in the stem portion 3002. Therefore, the distal radial component 3004 may be interconnected with the stem portion 3002 for an implantation. It will be understood that alternatively, the body portion 3010 may define a male connection and the stem portion 3002 may define a female connection. Thus, the interconnection may be performed in any appropriate manner and these are merely exemplary. In other examples, cooperating Morse connectors can be used.

With continued reference to FIG. 82, the stem portion 3002 includes a body portion 3028 and the male interconnection portion 3024. The male interconnection portion 3024 may include a connection area, such as a male connection post, to engage a respective female connection area, discussed herein in the distal radial component 3004. For example, the male interconnection portion 3024 may include a threaded male member that is operable to mate with a complementary female threaded portion of the distal radial component 3004. Other connections may be used. Nevertheless, the male interconnection portion 3024 may be provided to allow for an interconnection of the stem portion 3002 with the distal radial component 3004. It is appreciated that the male and female connection portions 3024 and 3022 can be formed on opposite components.

The body portion 3028 of the stem portion 3002 may include a selected geometry. For example, the body portion 3028 may be substantially cylindrical or tapered/conical to allow for easy insertion of the stem portion 3002 into the radius 2. The body portion 3028, however, may include a selected geometry to substantially resist rotation of the distal radial implant 3000 after implantation. For example, various extensions or keys, such as a volar flange 3030, may be provided that extend from an exterior of the body portion 3028, such that the volar flange 3030 may engage a selected portion of the bone. While the volar flange 3030 is shown generally having planar members extending medially and laterally from the body portion 3028, they may take other forms and/or extend in other directions such as, but not limited to an anterior and posterior direction. In addition, the body portion 3028 may include a selected irregular geometry or regular geometry that includes portions that may resist the rotation. In another example, the volar flange 3030 can be integrally formed with the body portion 3010 of the distal radial component 3004.

Furthermore, the stem portion 3002 may be provided in a plurality of dimensions, such as a diameter, length, curve radius, cross-section, and combinations thereof. For example, the stem portion 3002 may include a diameter or a cross-sectional size, length or any other selected dimension that may be varied. Therefore, a kit (such as the kit 1600, FIG. 44), or other appropriate selection may be provided, such that one or more stem portions 3002 may be provided with one or more variations in the selected dimensions. For example, a plurality of stem portions 3002 may be provided where each of the stem portions 3002 includes a slightly different length, such as about 4 cm, 6 cm, or about 8 cm. Therefore, during a procedure, such as an implantation of the distal radial implant 3000, a user, such as a physician, may select the appropriate length for the stem portion 3002.

Figure 83:
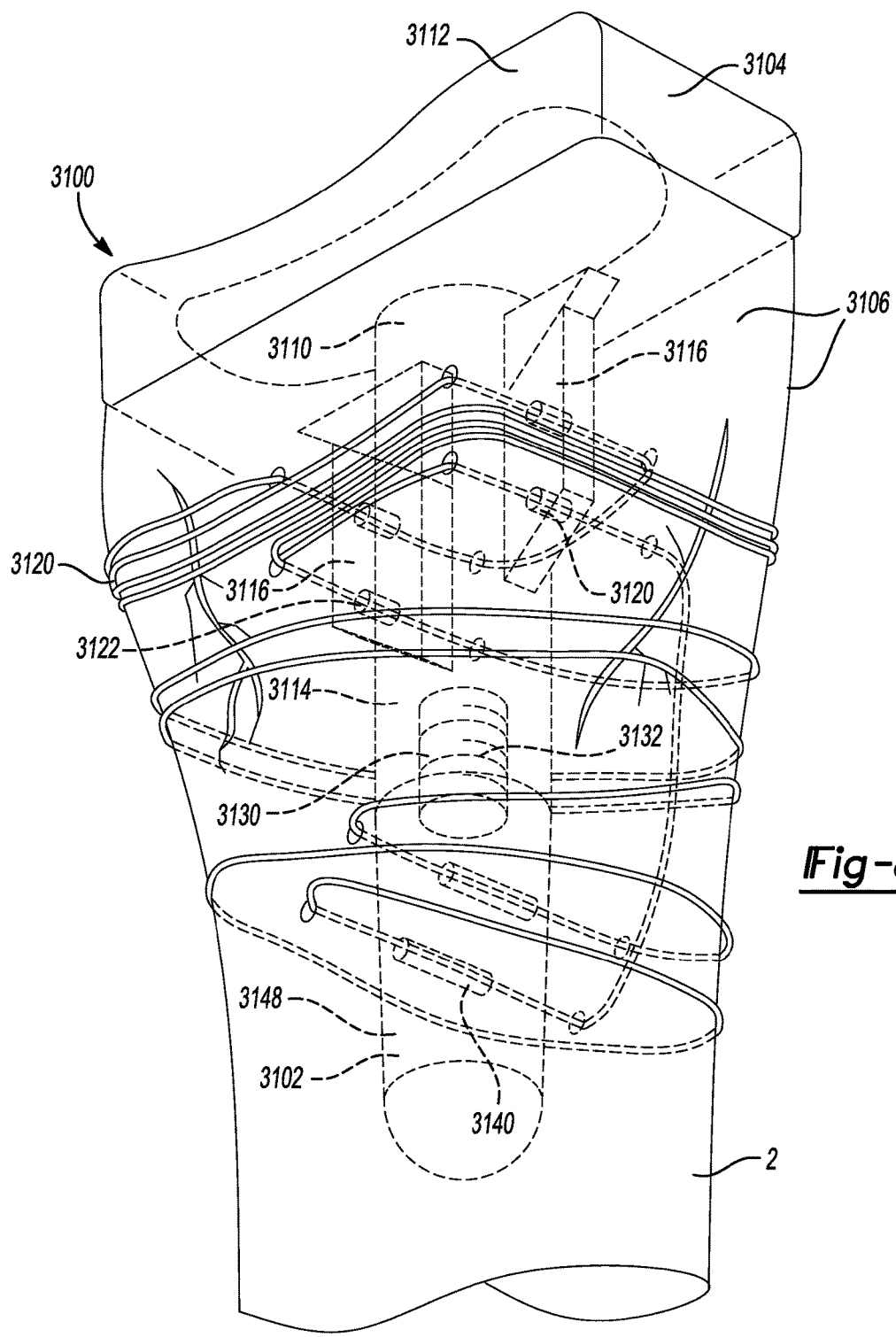
FIG. 83 is an anterior view of another distal radial implant constructed in accordance to additional features of the present teachings.

With reference now to FIG. 83, a distal radial implant 3100 is illustrated according to various embodiments. The distal radial implant 3100 may be provided as a substantially modular implant that includes a stem portion 3102 that is operable to be positioned relative to a selected portion of the radius 2, such as the intramedullary canal. Affixed or interconnected with a selected portion of the stem portion 3102 is a distal radial component 3104. The distal radial component 3104 may be provided to engage the stem portion 3102 to provide a selected orientation, configuration, size or other considerations for the distal radial implant 3100. As will be described, the distal radial implant 3100 can be used to salvage some or all fractured native radial bones 3106 in the host distal radius 2. The fractured native radial bones 3106 can be built up around an extension portion or boss of the distal radial component 3104 and held in position, such as with supplemental fasteners.

The distal radial component 3104 generally includes a body portion 3110 having a superior or articulating portion 3112. The body portion 3110 is generally in the form of a longitudinal boss 3114 having laterally extending fins 3116. While the fins 3116 are shown in the figure as two oppositely extending planar members, they can include one or more than two fins that are arranged at any location and having any shape along the longitudinal boss 3114. The fins 3116 can have apertures 3120 formed therein. The apertures 3120 can accommodate supplemental fasteners, such as flexible members including suture and/or wire and/or mechanical fasteners, etc. The supplemental fasteners, identified in the drawings as suture 3122, can be attached, wrapped around, coupled to, or otherwise engaged with fractured native radial bone 3106. The supplemental suture 3122 can locate the fractured native radial bones 3106 in a substantially fixed location around the longitudinal boss 3114 and generally between the articulating portion 3112 and the undamaged or unfractured portion of the host radius 2. According to some examples, the suture 3122 can be wrapped around, over, through and/or into some or all of the fractural native radial bones 3106 and additionally passed through the apertures 3120. The suture 3122 can be secured at one of or both opposite ends to apertures 3120. The sutures 3122 can additionally or alternatively be secured to the fractured native radial bones 3106.

The body portion 3110 may be formed in any appropriate manner to engage a selected portion of the anatomy. The body portion 3110 may include various dimensions for accommodating a specific patient as described herein. In this way, once the size of the host radius and/or carpal complex has been determined, a distal radial component 3104 having an appropriate size is selected. The longitudinal boss 3114 may include a selected diameter to substantially take up space that may be otherwise unaccommodated by host radial bone. In this way, it may be desirable to keep all or only some of the fractured native radial bones 3106. The available cross-sectional profile space of the host distal radius can be accommodated by the longitudinal boss 3114 and the fractured native radial bones 3106. It may be desirable in some circumstances to additionally or alternatively utilize flowable adhesive, such as bone cement around the fractured native radial bones 3106 and/or the fins 3116 and/or the suture 3122. In this way, a plurality of distal radial components 3104, each including a unique set of dimensions may be provided. A region of the body portion 3110 may also be coated with various materials, such as porous plasma spray and/or hydroxyapatite, to promote bony integration of the bone fragments to the implant. Each may be provided in a large inventory or in a kit similar to the kit 1600, FIG. 44, for selection by a user substantially intraoperatively or preoperatively. Nevertheless, various sizes or configurations of the distal radial implants 3100 may be provided to allow for a substantially customized fit with a selected patient.

The body portion 3110 of the distal radial component 3104 may also include the articulating region or portion 3112 that may also include a plurality of selected dimensions. For example, the articulating region 3112 may include a length (medial/lateral dimension) and width (anterior/posterior direction). The articulating region 3112 may also include an articulation depth that may vary depending upon a selected application. The articulation depth may generally be understood to be the deepest portion of the concave region that defines the articulating surface of the articulating region 3112. Again, the articulating region 3112 can include various dimensions that may be varied and unique for a given patient's circumstances.

Defined in the body portion 3110, is a female receiving or interconnection portion or depression 3130. The female interconnection 3130 may include a dimension that allows for substantial interconnection with a male interconnection 3132 of the stem portion 3102. In other configurations, the reception or interconnection portion 3130 may include a deformable member (such as a canted coil spring or screw or other mechanism), which may engage a depression of the stem portion 3102. In other examples, a Morse taper interconnection can be additionally or alternatively provided. Therefore, the distal radial component 3104 may be interconnected with the stem portion 3102 for an implantation. It will be understood that alternatively, the body portion 3110 may define a male connection and the stem portion 3102 may define a female connection. Thus, the interconnection may be performed in any appropriate manner and these are merely exemplary. In other examples, the distal radial component 3104 and the stem portion 3102 can be a unitary, monolithic component.

With continued reference to FIG. 83, the stem portion 3102 includes a body portion 3138 and the male interconnection portion 3132. The body portion 3138 can include apertures 3140 formed therein. The apertures 3140 can receive the supplemental fasteners (such as suture 3122) to further secure the host fractured native radial bone 3106 to the distal radial implant 3100. The male interconnection portion 3132 may include a connection area, such as a male connection post, to engage a respective female connection area, discussed above, in the distal radial component 3104. For example, the stem connection portion 3132 may include a threaded male member that is operable to mate with a complementary female threaded portion of the distal radial component 3104. Other connections may be used. Nevertheless, the connection member 3132 may be provided to allow for interconnection of the stem portion 3102 with the distal radial component 3104. The body portion 3138 of the stem portion 3102 may include a selected geometry. For example, the body portion 3138 may be substantially cylindrical or tapered/conical to allow for easy insertion of the stem portion 3102 into the radius 2. Again, once the size of the host radius and/or carpal complex has been determined, a stem portion 3102 having an appropriate size is selected and connected to the distal radial component 3104.

With reference now to FIGS. 84 and 85, a pair of distal radial implants 3200, 3200' are illustrated according to various embodiments. The distal radial implant 3200 (3200') may be provided as a substantially modular implant that includes an articulation portion 3202 (3202'), a body portion 3204 (3204'), and a stem portion 3206 (3206'). The stem portion 3206 (3206') is operable to be positioned relative to a selected portion of the radius 2, such as the intramedullary canal. Affixed or interconnected with a selected portion of the stem portion 3206 (3206') is the articulation portion 3202 (3202'). The articulation portion 3202 (3202') may be provided to engage the stem portion 3206 (3206') to provide a selected orientation, configuration, size or other considerations for the distal radial implant 3200.

The body portion 3204 (3204') can be generally in the form of an elliptical member having a central passage 3208 (3208'). The body portion 3204 (3204') can be made in multiple sizes and heights to connect between the articulation portion 3202 (3202') and the stem portion 3206 (3206') as needed. The body portion 3204 (3204') has proximally extending tabs 3210 (3210') that can locate into host radial bone 2. In the example shown in FIG. 84, host radial bone 2 can extend distally relative to the stem portion 3206.

The body portion 3204 (3204') may be formed in any appropriate manner to engage and/or take up space of a selected portion of the anatomy. The body portion 3204 (3204') may include various dimensions for accommodating a specific patient as described herein. In this way, a plurality of articulation portions 3202 (3202') having longitudinal bosses 3214 (3214') each including a unique set of dimensions may be provided for cooperating with various body portions 3204 (3204'). Each may be provided in a large inventory or in a kit similar to the kit 1600, FIG. 44, for selection by a user substantially intraoperatively or preoperatively. Nevertheless, various sizes or configurations of the distal radial implants 3200 (3200') may be provided to allow for a substantially customized fit with a selected patient.

The articulation portion 3202 (3202') may include a length (medial/lateral dimension) and a width (anterior/posterior direction). The articulation portion 3202 (3202') may also include an articulation depth that has a concave depression generally along the anterior/posterior direction and medial/lateral direction and may vary depending upon a selected application. Defined in the longitudinal boss 3214 (3214') of the articulation portion 3202 (3202') is a female receiving or interconnection portion or depression 3220 (3220'). The female interconnection portion 3220 (3220') may include a dimension that allows for substantial interconnection with a male interconnection portion 3222 (3222') of the stem portion 3206 (3206'). In other configurations, the reception or interconnection portion 3220 (3220') may include a deformable member, which may engage a depression of the stem portion 3206 (3206'). The female and male interconnection portions 3222 (3222'), 3220 (3220') can additionally or alternatively include Morse taper connections. Therefore, the distal radial implant 3200 (3200') may be interconnected with the stem portion 3206 (3206') for an implantation. It will be understood that alternatively, the longitudinal boss 3214 (3214') may define a male connection and the stem portion 3206 (3206') may define a female connection. Thus, the interconnection may be performed in any appropriate manner and these are merely exemplary.

With continued reference to FIGS. 84 and 85, the stem portion 3206 (3206') includes a stem body portion 3226 (3226') and the male interconnection portion 3222 (3222'). The male interconnection portion 3222 (3222') may include a connection area, such as a male connection posed to engage a respective female connection area, discussed above, in the articulation portion 3202 (3202'). For example, the stem connection portion 3222 (3222') may include a threaded male member that is operable to mate with a complementary female threaded portion of the longitudinal boss 3214 (3214') of the articulation portion 3202 (3202'). Other connections may be used. Nevertheless, the connection member 3222 (3222') may be provided to allow for interconnection of the stem portion 3206 (3206') with the longitudinal boss 3214 (3214') of the articulation portion 3202 (3202'). The stem body portion 3226 (3226') of the stem portion 3206 (3206') may include a selected geometry. For example, the stem body portion 3226 (3226') may be substantially cylindrical or tapered/conical to allow for easy insertion of the stem portion 3206 (3206') into the radius 2. Various stems having different heights may be provided.

Figure 86:
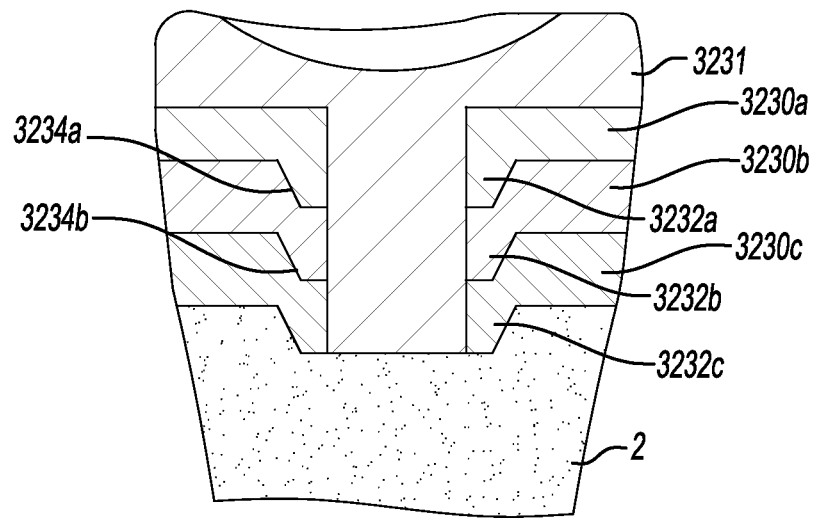
FIG. 86 is an anterior view of an exemplary articulation portion having a series of stackable body portions stacked thereon.

In another example shown in FIG. 86, a series of stackable body portions 3230a, 3230b and 3230c are provided for accommodating a desired height on an exemplary radial implant 3231 to account for various bone loss as needed for a particular patient. Each body portion 3230a, 3230b and 3230c can have proximally extending tabs 3232a, 3232b and 3232c that can locate into complementary recesses 3234a, 3234b formed on distal surfaces of both of the body portions 3230a and 3230b, respectively. The tabs 3232c can locate into host radial bone 2. Any or all of the body portions disclosed herein can be formed of PEEK to reduce implant weight. While not specifically shown, a stem portion may additionally be provided.

Figure 87:
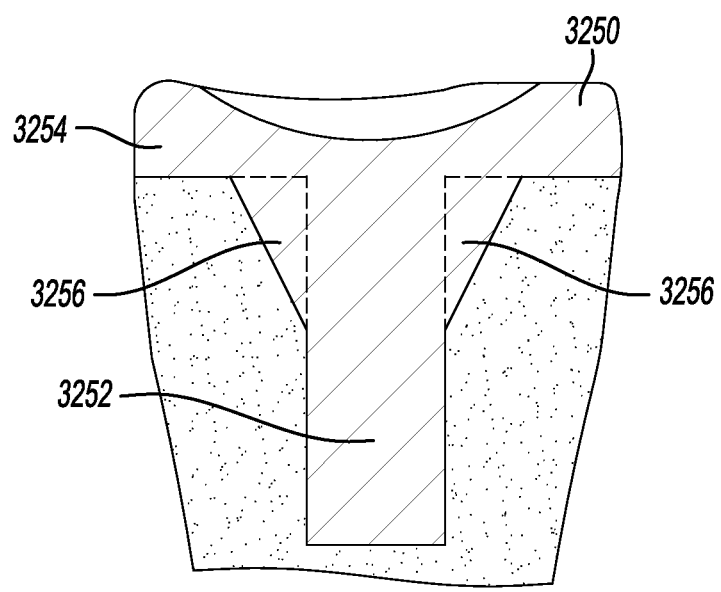
FIG. 87 is an anterior view of another distal radial implant constructed in accordance with additional features of the present teachings.

Turning now to FIG. 87, a distal radial implant 3250 is illustrated according to various embodiments. The distal radial implant 3250 may be included as a unitary component having an integrally formed stem portion 3252 that extends proximally from an articulation portion 3254. Fins 3256 can be formed between the stem portion 3252 and the articulation portion 3254. The distal radial implant 3250 can be implanted into the distal radius for providing an articulation surface on a distal surface thereof. In another example, the stem portion 3252 can also be extended with a longer stem portion, such as 3206 where additional fixation is required.

Figure 88:
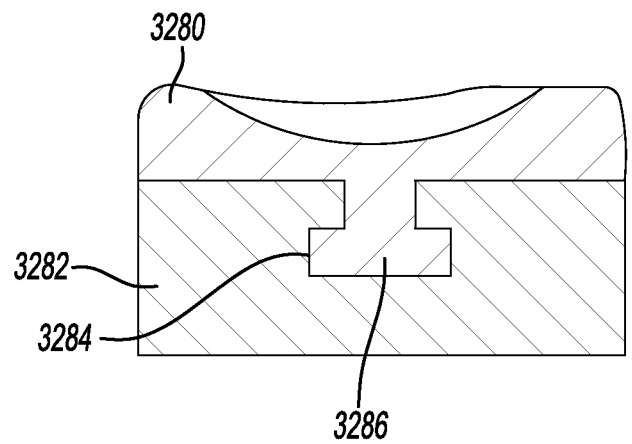
FIG. 88 is an anterior view of an exemplary interconnection feature used between exemplary articulation portions and body portions of the present teachings.

With reference now to FIG. 88, an exemplary interconnection between a body portion 3280 and an articulation portion 3282 is shown according to one example. The interconnection can be in the form of cooperating T-shaped protrusions and complementary slots 3284, 3286, respectively. In this exemplary connection, the T-shaped protrusion 3284 can slidably locate within the complementary female T-shaped slot 3286 to connect the body portion 3280 and the articulation portion 3282. While the T-shaped interconnection portions are shown with respect to interconnecting the body portion 3280 and the articulation portion 3282, the T-shaped protrusion and slot 3284, 3286 may be formed on other components (such as a stem) for interconnecting to each other). Other connection geometries may include Morse taper, locking rings, fasteners, including screws, rails and slots, friction fits, or any other suitable connection methods.

Figure 89:
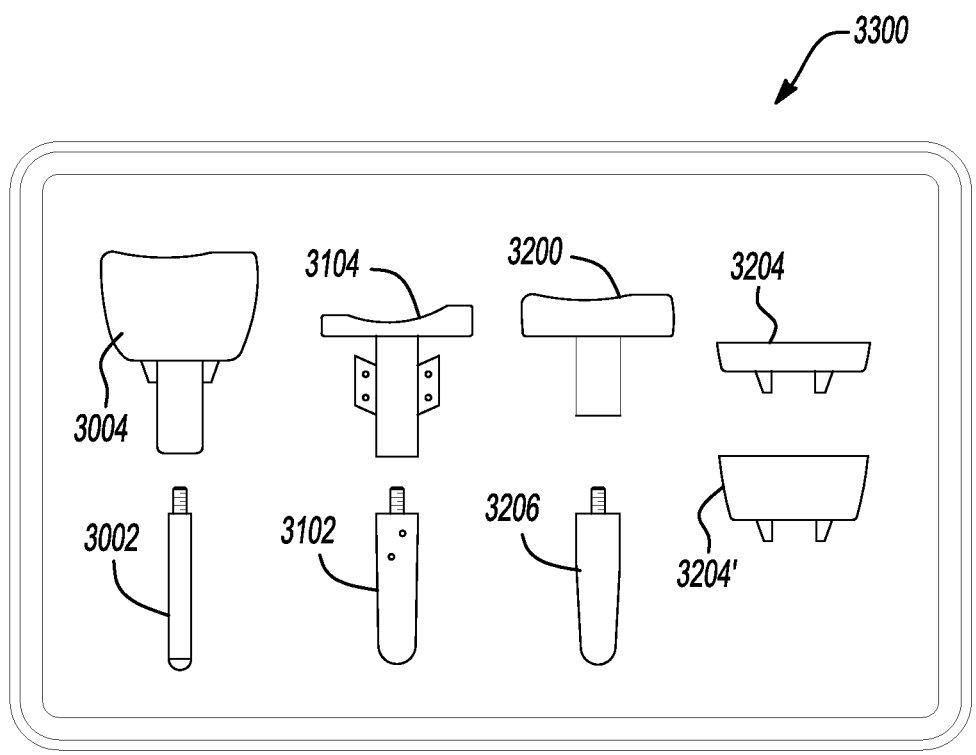
FIG. 89 is an exemplary kit having various radial implant components according to various examples.

With reference to FIG. 89, an exemplary kit 3300 that can include various distal radial components 3004, 3104, 3200; body portions 3204, 3204'; and stem portions 3002, 3102, 3206. According to one example, a surgeon can initially examine the fracture in a given radius. If it is determined that the fractured bone cannot be saved, the surgeon can resect a portion of the distal radius and use combinations of the distal radial components 3004, 3104, 3200; body portions 3204, 3204'; and stem portions 3002, 3102, 3206 as desired. If it is determined that some or all portions of fractured radial bone are to be saved, the surgeon can select the distal radial component 3100 and optionally a suitable stem portion 3002, 3102, 3206. The fractured radial bones will be secured as discussed above rather than utilizing a body portion 3204, 3204'. In some examples, a body portion having a relatively narrow height can be used in conjunction with the distal radial component 3104 while still securing some fractured host radial bone.

Accordingly, while the description includes various embodiments as illustrated in the drawings, it will be understood by those skilled in the art that various changes may be made and equivalents may be substituted for elements thereof without departing from the scope of the description or the appended claims. In addition, many modifications can be made to adapt a particular situation or material to the teachings without departing from the scope thereof. Therefore, it is intended that the teachings are not limited to any various embodiment illustrated in the drawings and described in the specification as the best mode presently contemplated for carrying out the teachings herein, but that the teachings will include any various embodiments falling within the foregoing teachings and the appended claims.

What is claimed is:

1. A method of implanting a wrist prosthesis in a distal portion of an ulna for articulation at least near a radius and a carpal complex of a wrist joint, comprising:
    forming an incision near a distal portion of the radius and ulna joint;
    resecting a distal portion of the ulna;
    positioning a stage member in a fixed position relative to the ulna;
    sliding a bearing member perpendicularly relative to a longitudinal length of the stage member to hold the bearing member relative to the stage member and the distal ulna such that an inner end surface of a stage mounting region of the bearing member abuts, in a directional perpendicular to the longitudinal length of the stage member and in the direction the bearing member is being slid, an end surface of a bearing mounting member extending from a surface of the stage member, and wherein the bearing member has an exposed bearing surface facing towards and configured to articulate with a natural distal radius or a distal radial implant;
    fixing the bearing member to the bearing mounting member extending from the stage member; and
    attaching soft tissue to at least one of the bearing member and the stage member.

2. The method of claim 1, wherein forming the incision near the distal portion of the radius and the ulna joint includes forming the incision only on one of an anterior side of the wrist at the distal portion of the radius and ulna joint or on a posterior side of the wrist at the distal portion of the radius and ulna joint.

3. The method of claim 1, wherein fixing the bearing member includes passing a locking member through the bearing member to connect with a portion of the stage member to fix the bearing member to the stage member and relative to the ulna.

4. The method of claim 1, further comprising:
    selecting the bearing member from a plurality of bearing members;
    selecting the stage member from a plurality of stage members;
    wherein each of the plurality of bearing members includes a distinct height, width, articulation surface configuration, or combinations thereof; and
    wherein each of the stage members includes a stem portion extending from a stage member having a distinct length.

5. The method of claim 1, wherein attaching soft tissue includes:
    passing an anchor member through a bore defined by the stage member or the bearing member that is connected with the soft tissue.

6. The method of claim 5, wherein the soft tissue includes a Triangular fibrocartilage complex.

7. The method of claim 1, further comprising:
    selecting a bone replacement portion having a height operable to replace the resected distal portion of the ulna when combined and implanted with the stage member and the bearing member; and
    positioning the bone replacement member between the stage member and a distal portion of the resected portion of the ulna.

8. The method of claim 1, further comprising resecting a portion of the carpal complex.

9. The method of claim 1, wherein sliding the bearing member relative to the stage member includes sliding the bearing member in a first direction, and wherein fixing the bearing member to the bearing mounting member includes passing an anchor member in the first direction through a bore defined by the stage member or the bearing member.

10. The method of claim 1, wherein positioning a stage member in a fixed position relative to the ulna includes positioning a stem portion within an intramedullary canal of the ulna.

11. The method of claim 1, further comprising positioning a radial implant in a fixed position relative to the radius.

12. The method of claim 11, wherein positioning the radial implant in a fixed position relative to the radius includes forming a bore in the radius and positioning a stem portion of the radial implant within the bore.

13. The method of claim 1, wherein the bearing member includes a first member and a second member, the method further comprising sliding the first member relative to the second member to hold the first member relative to the second member, and wherein sliding the bearing member relative to the stage member includes sliding the first and second members relative to the stage members.

14. A method of implanting a wrist prosthesis in a distal portion of an ulna for articulation at least near a radius and a carpal complex of a wrist joint, comprising:
    forming an incision near the wrist joint;
    resecting a distal portion of the ulna;
    positioning a stage member in a fixed position relative to the ulna, including passing a stem portion of the stage member in a first direction within an intramedullary canal of the ulna, the stage member including a bearing mounting portion extending above a surface of the stage member;
    sliding a bearing member in a second direction, substantially perpendicular to the first direction, relative to the stage member to hold the bearing member relative to the stage member and the distal ulna, the bearing member including a stage mounting portion complementary to the bearing mounting portion of the stage member to receive the bearing mounting portion of the stage member as the bearing member is slid in place, wherein the stage mounting portion of the bearing member does not extend through the bearing member such that an inner end surface of the stage mounting portion of the bearing member abuts, in a directional perpendicular to the longitudinal length of the stage member and in the direction the bearing member is being slid, an end surface of the bearing mounting portion of the stage member, and wherein the bearing member has an exposed bearing surface facing towards and configured to articulate with a natural distal radius or a distal radial implant; and
    attaching soft tissue to at least one of the bearing member and the stage member.

15. The method of claim 14, further comprising fixing the bearing member to the bearing mounting portion of the stage member extending from the stage member.

16. The method of claim 14, wherein fixing the bearing member includes passing a locking member in the first direction and through the bearing member to connect with a portion of the stage member.

17. The method of claim 14, further comprising:
selecting the bearing member from a plurality of bearing members;
selecting the stage member from a plurality of stage members;
wherein each of the plurality of bearing members includes a distinct height, width, articulation surface configuration, or combinations thereof; and
wherein the stem portion of each of the plurality of stage members extends a distinct length from the stage member.

18. The method of claim 14, wherein attaching soft tissue includes:
passing an anchor member through a bore defined by the stage member or the bearing member that is connected with the soft tissue.

19. The method of claim 18, wherein the soft tissue includes a Triangular fibrocartilage complex.

20. The method of claim 14, further comprising:
selecting a bone replacement portion having a height operable to replace the resected distal portion of the ulna when combined and implanted with the stage member and the bearing member; and
positioning the bone replacement member between the stage member and a distal portion of the resected portion of the ulna.

\* \* \* \* \*